US011146680B2

(12) United States Patent
Leavitt et al.

(10) Patent No.: US 11,146,680 B2
(45) Date of Patent: Oct. 12, 2021

(54) SYSTEMS AND METHODS FOR EMERGENCY DATA INTEGRATION

(71) Applicant: RapidSOS, Inc., New York, NY (US)

(72) Inventors: Lucas Richard Eager Leavitt, Forest Hill, NY (US); Gabriel Mahoney, Brooklyn, NY (US); Zvika Ferentz, Rye Brook, NY (US); William Pellegrini, Graham, WA (US)

(73) Assignee: RAPIDSOS, INC., New York, NY (US)

(*) Notice: Subject to any disclaimer, the term of this patent is extended or adjusted under 35 U.S.C. 154(b) by 0 days.

(21) Appl. No.: 16/834,914

(22) Filed: Mar. 30, 2020

(65) Prior Publication Data

US 2020/0314240 A1    Oct. 1, 2020

Related U.S. Application Data

(60) Provisional application No. 62/826,680, filed on Mar. 29, 2019.

(51) Int. Cl.
*H04M 3/51* (2006.01)
*H04L 29/08* (2006.01)
*G16H 40/67* (2018.01)

(52) U.S. Cl.
CPC .......... *H04M 3/5116* (2013.01); *G16H 40/67* (2018.01); *H04L 67/02* (2013.01); *H04L 67/20* (2013.01); *H04M 3/5133* (2013.01); *H04M 2201/42* (2013.01); *H04M 2242/04* (2013.01); *H04M 2242/30* (2013.01)

(58) Field of Classification Search
None
See application file for complete search history.

(56) References Cited

U.S. PATENT DOCUMENTS

| 5,379,337 A | 1/1995 | Castillo et al. |
| 5,479,482 A | 12/1995 | Grimes |
| 5,563,931 A | 10/1996 | Bishop et al. |
| 5,596,625 A | 1/1997 | Leblanc |
| 5,710,803 A | 1/1998 | Kowal et al. |

(Continued)

FOREIGN PATENT DOCUMENTS

| CA | 2662606 A1 | 10/2009 |
| CA | 2697986 A1 | 9/2010 |

(Continued)

OTHER PUBLICATIONS

Abel et al. Semantics+Filtering+Search=Twitcident exploring information in social web streams. HT'12—Proceedings of 23rd ACM Conference on Hypertext and Social Media (10 pgs) (Jun. 25-28, 2012).

(Continued)

*Primary Examiner* — Quoc D Tran
(74) *Attorney, Agent, or Firm* — Wilson Sonsini Goodrich & Rosati

(57) ABSTRACT

Described herein are systems, devices, methods, and media providing emergency data to emergency service providers (ESP; e.g., public safety answering points (PSAPs)). Also provided are systems, methods, and media for utilizing location data and geofences to provide emergency data to ESPs and interactive graphical displays to efficiently display relevant emergency data.

20 Claims, 24 Drawing Sheets

(56) References Cited

U.S. PATENT DOCUMENTS

| | | | |
|---|---|---|---|
| 5,742,666 | A | 4/1998 | Alpert |
| 6,014,555 | A | 1/2000 | Tendler |
| 6,133,853 | A | 10/2000 | Obradovich et al. |
| 6,249,674 | B1 | 6/2001 | Verdonk |
| 6,252,943 | B1 | 6/2001 | Johnson et al. |
| 6,256,489 | B1 | 7/2001 | Lichter et al. |
| 6,363,138 | B1 | 3/2002 | Aprile |
| 6,459,782 | B1 | 10/2002 | Bedrosian et al. |
| 6,477,362 | B1 | 11/2002 | Raith et al. |
| 6,502,030 | B2 | 12/2002 | Hilleary |
| 6,510,315 | B1 | 1/2003 | Arnson |
| 6,556,816 | B1 | 4/2003 | Gafrick et al. |
| 6,571,092 | B2 | 5/2003 | Faccin et al. |
| 6,574,323 | B1 | 6/2003 | Manuel et al. |
| 6,587,545 | B1 | 7/2003 | Antonucci et al. |
| 6,594,666 | B1 | 7/2003 | Biswas et al. |
| 6,600,812 | B1 | 7/2003 | Gentillin et al. |
| 6,628,933 | B1 | 9/2003 | Humes |
| 6,680,998 | B1 | 1/2004 | Bell et al. |
| 6,707,421 | B1 | 3/2004 | Drury et al. |
| 6,731,610 | B2 | 5/2004 | Sajikawa et al. |
| 6,993,118 | B2 | 1/2006 | Antonucci et al. |
| 7,054,611 | B2 | 5/2006 | Eisner et al. |
| 7,058,385 | B2 | 6/2006 | Lauper |
| 7,084,775 | B1 | 8/2006 | Smith |
| 7,177,400 | B2 | 2/2007 | Eisner et al. |
| 7,224,773 | B2 | 5/2007 | Croak et al. |
| 7,271,704 | B2 | 9/2007 | McSheffrey et al. |
| 7,313,402 | B1 | 12/2007 | Rahman |
| 7,324,801 | B2 | 1/2008 | Droste et al. |
| 7,349,706 | B2 | 3/2008 | Kim et al. |
| 7,409,044 | B2 | 8/2008 | Leduc |
| 7,436,938 | B2 | 10/2008 | Savaglio et al. |
| 7,437,143 | B1 | 10/2008 | Williams |
| 7,469,138 | B2 | 12/2008 | Dayar et al. |
| 7,483,519 | B2 | 1/2009 | Binning |
| 7,519,351 | B2 | 4/2009 | Malone, III et al. |
| 7,519,372 | B2 | 4/2009 | MacDonald et al. |
| 7,548,158 | B2 | 6/2009 | Titus et al. |
| 7,565,131 | B2 | 7/2009 | Rollender |
| 7,646,854 | B2 | 1/2010 | Anderson |
| 7,676,215 | B2 | 3/2010 | Chin et al. |
| 7,684,782 | B2 | 3/2010 | Ashley, Jr. et al. |
| 7,848,733 | B2 | 12/2010 | Bull et al. |
| 7,937,067 | B2 | 5/2011 | Maier et al. |
| 7,949,326 | B2 | 5/2011 | Gallagher et al. |
| 8,009,810 | B2 | 8/2011 | Seidberg et al. |
| 8,041,335 | B2 | 10/2011 | Khetawat et al. |
| 8,041,341 | B1 | 10/2011 | Malackowski et al. |
| 8,045,954 | B2 | 10/2011 | Barbeau et al. |
| 8,068,881 | B2 | 11/2011 | Schrager |
| 8,102,972 | B2 | 1/2012 | Poremba |
| 8,126,424 | B2 | 2/2012 | Piett et al. |
| 8,150,367 | B1 | 4/2012 | Malladi et al. |
| 8,165,560 | B2 | 4/2012 | Stenquist |
| 8,165,562 | B2 | 4/2012 | Piett et al. |
| 8,185,087 | B2 | 5/2012 | Mitchell, Jr. et al. |
| 8,195,121 | B2 | 6/2012 | Dunn et al. |
| 8,219,135 | B2 | 7/2012 | De et al. |
| 8,244,205 | B2 | 8/2012 | Wu |
| 8,249,546 | B1 | 8/2012 | Shah et al. |
| 8,249,547 | B1 | 8/2012 | Fellner |
| 8,289,953 | B2 | 10/2012 | Ray et al. |
| 8,306,501 | B2 | 11/2012 | Moodbidri et al. |
| 8,326,260 | B1 | 12/2012 | Bradish et al. |
| 8,369,488 | B2 | 2/2013 | Sennett et al. |
| 8,396,970 | B2 | 3/2013 | Black et al. |
| 8,401,565 | B2 | 3/2013 | Sandberg et al. |
| 8,417,090 | B2 | 4/2013 | Fleming |
| 8,417,212 | B2 | 4/2013 | Cepuran et al. |
| 8,442,481 | B2 | 5/2013 | Maier et al. |
| 8,442,482 | B2 | 5/2013 | Maier et al. |
| 8,472,973 | B2 | 6/2013 | Lin et al. |
| 8,484,352 | B2 | 7/2013 | Piett et al. |
| 8,489,062 | B2 | 7/2013 | Ray et al. |
| 8,494,868 | B2 | 7/2013 | Saalsaa |
| 8,509,729 | B2 | 8/2013 | Shaw |
| 8,516,122 | B2 | 8/2013 | Piett et al. |
| 8,538,370 | B2 | 9/2013 | Ray et al. |
| 8,538,468 | B2 | 9/2013 | Daly |
| 8,594,015 | B2 | 11/2013 | Dunn et al. |
| 8,606,218 | B2 | 12/2013 | Ray et al. |
| 8,625,578 | B2 | 1/2014 | Roy et al. |
| 8,626,112 | B2 | 1/2014 | Ray et al. |
| 8,630,609 | B2 | 1/2014 | Ray et al. |
| 8,644,301 | B2 | 2/2014 | Tamhankar et al. |
| 8,682,279 | B2 | 3/2014 | Rudolf et al. |
| 8,682,281 | B2 | 3/2014 | Dunn et al. |
| 8,682,286 | B2 | 3/2014 | Dickinson et al. |
| 8,712,366 | B2 | 4/2014 | Greene et al. |
| 8,747,336 | B2 | 6/2014 | Tran |
| 8,751,265 | B2 | 6/2014 | Piett et al. |
| 8,755,767 | B2 | 6/2014 | Maier et al. |
| 8,760,290 | B2 * | 6/2014 | Piett ............... G06Q 30/02 340/540 |
| 8,811,935 | B2 | 8/2014 | Faccin et al. |
| 8,825,687 | B2 | 9/2014 | Marceau et al. |
| 8,848,877 | B2 | 9/2014 | Seidberg et al. |
| 8,866,606 | B1 | 10/2014 | Will et al. |
| 8,868,028 | B1 | 10/2014 | Kaltsukis |
| 8,880,021 | B2 | 11/2014 | Hawkins |
| 8,890,685 | B1 | 11/2014 | Sookman et al. |
| 8,918,075 | B2 | 12/2014 | Maier et al. |
| 8,948,732 | B1 | 2/2015 | Negahban et al. |
| 8,971,839 | B2 | 3/2015 | Hong |
| 8,984,143 | B2 | 3/2015 | Serra et al. |
| 9,008,078 | B2 | 4/2015 | Kamdar et al. |
| 9,014,657 | B2 | 4/2015 | Rohde et al. |
| 9,019,870 | B2 | 4/2015 | Khan et al. |
| 9,071,643 | B2 | 6/2015 | Saito et al. |
| 9,077,676 | B2 | 7/2015 | Price et al. |
| 9,078,092 | B2 | 7/2015 | Piett et al. |
| 9,094,816 | B2 | 7/2015 | Maier et al. |
| 9,167,379 | B1 | 10/2015 | Hamilton et al. |
| 9,244,922 | B2 | 1/2016 | Marceau et al. |
| 9,258,680 | B2 | 2/2016 | Drucker |
| 9,277,389 | B2 | 3/2016 | Saito et al. |
| 9,351,142 | B2 | 5/2016 | Basore et al. |
| 9,369,847 | B2 | 6/2016 | Borghei |
| 9,384,491 | B1 | 7/2016 | Briggs et al. |
| 9,402,159 | B1 | 7/2016 | Self et al. |
| 9,408,051 | B2 | 8/2016 | Finney et al. |
| 9,420,099 | B1 | 8/2016 | Krishnan et al. |
| 9,497,585 | B1 | 11/2016 | Cooley et al. |
| 9,503,876 | B2 | 11/2016 | Saito et al. |
| 9,544,750 | B1 | 1/2017 | Self et al. |
| 9,591,467 | B2 | 3/2017 | Piett et al. |
| 9,629,185 | B2 | 4/2017 | Gluckman et al. |
| 9,635,534 | B2 | 4/2017 | Maier et al. |
| 9,659,484 | B1 | 5/2017 | Mehta et al. |
| 9,693,213 | B2 | 6/2017 | Self et al. |
| 9,734,721 | B2 | 8/2017 | Stenneth et al. |
| 9,736,670 | B2 | 8/2017 | Mehta et al. |
| 9,756,169 | B2 | 9/2017 | Mehta et al. |
| 9,805,430 | B2 | 10/2017 | Miasnik et al. |
| 9,838,858 | B2 | 12/2017 | Anand et al. |
| 9,924,043 | B2 | 3/2018 | Mehta et al. |
| 9,942,739 | B2 | 4/2018 | Bozik et al. |
| 9,986,404 | B2 | 5/2018 | Mehta et al. |
| 9,992,655 | B2 | 6/2018 | Anand et al. |
| 9,998,507 | B2 | 6/2018 | Mehta et al. |
| 10,002,375 | B1 | 6/2018 | Scythes et al. |
| 10,136,294 | B2 | 11/2018 | Mehta et al. |
| 10,140,482 | B2 | 11/2018 | Mehta et al. |
| 10,140,842 | B2 | 11/2018 | Mehta et al. |
| 10,142,213 | B1 | 11/2018 | Hart et al. |
| 10,142,469 | B2 | 11/2018 | Klaban |
| 10,165,431 | B2 | 12/2018 | Bozik et al. |
| 10,375,558 | B2 | 8/2019 | Katz et al. |
| 10,419,915 | B2 | 9/2019 | Mehta et al. |
| 10,425,799 | B2 | 9/2019 | Anand et al. |
| 10,447,865 | B2 | 10/2019 | Mehta et al. |
| 2001/0051849 | A1 | 12/2001 | Boone |
| 2002/0001367 | A1 | 1/2002 | Lee |

(56) References Cited

U.S. PATENT DOCUMENTS

| | | |
|---|---|---|
| 2002/0027975 A1 | 3/2002 | Oxley |
| 2002/0057678 A1 | 5/2002 | Jiang et al. |
| 2002/0120698 A1 | 8/2002 | Tamargo |
| 2003/0069035 A1 | 4/2003 | Shurvinton |
| 2003/0109245 A1 | 6/2003 | McCalmont et al. |
| 2004/0203572 A1 | 10/2004 | Aerrabotu et al. |
| 2004/0229620 A1 | 11/2004 | Zhao et al. |
| 2004/0266390 A1 | 12/2004 | Faucher et al. |
| 2005/0085215 A1 | 4/2005 | Kokko et al. |
| 2005/0104745 A1 | 5/2005 | Bachelder et al. |
| 2005/0151642 A1 | 7/2005 | Tupler et al. |
| 2005/0190892 A1 | 9/2005 | Dawson et al. |
| 2005/0285181 A1 | 12/2005 | Yasui et al. |
| 2006/0085275 A1 | 4/2006 | Stokes et al. |
| 2006/0109960 A1 | 5/2006 | D'Evelyn et al. |
| 2006/0293024 A1 | 12/2006 | Benco et al. |
| 2007/0003024 A1 | 1/2007 | Olivier et al. |
| 2007/0030144 A1 | 2/2007 | Titus et al. |
| 2007/0030146 A1 | 2/2007 | Shepherd |
| 2007/0033095 A1 | 2/2007 | Hodgin et al. |
| 2007/0049287 A1 | 3/2007 | Dunn |
| 2007/0053308 A1 | 3/2007 | Dumas et al. |
| 2007/0058528 A1 | 3/2007 | Massa et al. |
| 2007/0060097 A1 | 3/2007 | Edge et al. |
| 2007/0161383 A1 | 7/2007 | Caci |
| 2007/0164872 A1 | 7/2007 | Monroe |
| 2007/0171854 A1 | 7/2007 | Chen et al. |
| 2007/0218895 A1 | 9/2007 | Saito et al. |
| 2008/0019268 A1 | 1/2008 | Rollins |
| 2008/0063153 A1 | 3/2008 | Krivorot et al. |
| 2008/0081646 A1 | 4/2008 | Morin et al. |
| 2008/0166990 A1 | 7/2008 | Toiv |
| 2008/0194238 A1 | 8/2008 | Kwon |
| 2008/0253535 A1 | 10/2008 | Sherry et al. |
| 2008/0294058 A1 | 11/2008 | Shklarski |
| 2009/0097474 A1* | 4/2009 | Ray .................... H04M 3/5116 370/352 |
| 2009/0134982 A1 | 5/2009 | Robertson et al. |
| 2009/0186596 A1 | 7/2009 | Kaltsukis |
| 2009/0214000 A1 | 8/2009 | Patel et al. |
| 2009/0257345 A1 | 10/2009 | King |
| 2009/0322513 A1 | 12/2009 | Hwang et al. |
| 2010/0002846 A1 | 1/2010 | Ray et al. |
| 2010/0003964 A1 | 1/2010 | Khare et al. |
| 2010/0093305 A1 | 4/2010 | Reich et al. |
| 2010/0156626 A1 | 6/2010 | Story |
| 2010/0159976 A1 | 6/2010 | Marocchi et al. |
| 2010/0166153 A1 | 7/2010 | Guleria et al. |
| 2010/0202368 A1 | 8/2010 | Hans |
| 2010/0238018 A1 | 9/2010 | Kelly |
| 2010/0261448 A1 | 10/2010 | Peters |
| 2010/0262668 A1 | 10/2010 | Piett et al. |
| 2011/0009086 A1 | 1/2011 | Poremba et al. |
| 2011/0029600 A1 | 2/2011 | Theimer |
| 2011/0071880 A1 | 3/2011 | Spector |
| 2011/0086607 A1 | 4/2011 | Wang et al. |
| 2011/0103266 A1 | 5/2011 | Andreasen et al. |
| 2011/0134897 A1 | 6/2011 | Montemurro et al. |
| 2011/0153368 A1 | 6/2011 | Pierre et al. |
| 2011/0201357 A1 | 8/2011 | Garrett et al. |
| 2011/0263219 A1 | 10/2011 | Hasenfang et al. |
| 2012/0002792 A1 | 1/2012 | Chang |
| 2012/0028599 A1 | 2/2012 | Hatton et al. |
| 2012/0029970 A1 | 2/2012 | Stiles et al. |
| 2012/0040636 A1 | 2/2012 | Kazmi |
| 2012/0092161 A1 | 4/2012 | West |
| 2012/0144019 A1 | 6/2012 | Zhu |
| 2012/0196557 A1 | 8/2012 | Reich et al. |
| 2012/0196558 A1 | 8/2012 | Reich et al. |
| 2012/0202428 A1 | 8/2012 | Mirbaha et al. |
| 2012/0210325 A1 | 8/2012 | De Lind Van Wijngaarden et al. |
| 2012/0218102 A1 | 8/2012 | Bivens et al. |
| 2012/0256745 A1 | 10/2012 | Piett et al. |
| 2012/0257729 A1 | 10/2012 | Piett et al. |
| 2012/0258680 A1 | 10/2012 | Piett et al. |
| 2012/0289243 A1 | 11/2012 | Tarlow et al. |
| 2012/0295575 A1 | 11/2012 | Nam |
| 2012/0309341 A1 | 12/2012 | Ward |
| 2013/0005295 A1 | 1/2013 | Park et al. |
| 2013/0030825 A1 | 1/2013 | Bagwandeen et al. |
| 2013/0036175 A1 | 2/2013 | Lau |
| 2013/0052983 A1 | 2/2013 | Fletcher et al. |
| 2013/0065569 A1 | 3/2013 | Leipzig et al. |
| 2013/0072144 A1 | 3/2013 | Berger et al. |
| 2013/0084824 A1 | 4/2013 | Hursey |
| 2013/0102351 A1 | 4/2013 | Mo |
| 2013/0122932 A1 | 5/2013 | Patel et al. |
| 2013/0138791 A1 | 5/2013 | Thomas et al. |
| 2013/0183924 A1 | 7/2013 | Saigh et al. |
| 2013/0185368 A1 | 7/2013 | Nordstrom et al. |
| 2013/0203373 A1 | 8/2013 | Edge |
| 2013/0203376 A1 | 8/2013 | Maier et al. |
| 2013/0226369 A1 | 8/2013 | Yorio et al. |
| 2013/0237175 A1 | 9/2013 | Piett |
| 2013/0237181 A1 | 9/2013 | Ray |
| 2013/0260710 A1 | 10/2013 | Hr |
| 2013/0309994 A1 | 11/2013 | Hellwig et al. |
| 2013/0331055 A1 | 12/2013 | McKown et al. |
| 2014/0051379 A1 | 2/2014 | Ganesh et al. |
| 2014/0086108 A1 | 3/2014 | Dunn et al. |
| 2014/0087680 A1 | 3/2014 | Luukkala et al. |
| 2014/0095425 A1 | 4/2014 | Sipple |
| 2014/0113606 A1 | 4/2014 | Morken et al. |
| 2014/0126356 A1 | 5/2014 | Lee et al. |
| 2014/0142979 A1 | 5/2014 | Mitsunaga |
| 2014/0148120 A1 | 5/2014 | Buck |
| 2014/0155017 A1 | 6/2014 | Fan et al. |
| 2014/0155018 A1 | 6/2014 | Fan et al. |
| 2014/0164505 A1 | 6/2014 | Daly et al. |
| 2014/0199959 A1 | 7/2014 | Hassan et al. |
| 2014/0222462 A1 | 8/2014 | Shakil et al. |
| 2014/0248848 A1 | 9/2014 | Mufti et al. |
| 2014/0302810 A1 | 10/2014 | Inha et al. |
| 2014/0324351 A1 | 10/2014 | Dannevik et al. |
| 2014/0359008 A1 | 12/2014 | Finney et al. |
| 2014/0370836 A1 | 12/2014 | Gladstone |
| 2015/0029836 A1 | 1/2015 | Hans et al. |
| 2015/0055453 A1 | 2/2015 | Chaki et al. |
| 2015/0065082 A1 | 3/2015 | Sehgal |
| 2015/0081209 A1 | 3/2015 | Yeh et al. |
| 2015/0085997 A1 | 3/2015 | Biage et al. |
| 2015/0099481 A1 | 4/2015 | Maitre et al. |
| 2015/0109125 A1 | 4/2015 | Kaib et al. |
| 2015/0111524 A1 | 4/2015 | South et al. |
| 2015/0137972 A1 | 5/2015 | Nepo et al. |
| 2015/0172897 A1 | 6/2015 | Mariathasan et al. |
| 2015/0181401 A1 | 6/2015 | Dhandu et al. |
| 2015/0289121 A1 | 10/2015 | Lesage et al. |
| 2015/0304827 A1 | 10/2015 | Price et al. |
| 2015/0317392 A1 | 11/2015 | Fernandez |
| 2015/0350262 A1 | 12/2015 | Rainisto et al. |
| 2015/0358794 A1 | 12/2015 | Nokhoudian et al. |
| 2015/0365319 A1 | 12/2015 | Finn et al. |
| 2016/0004224 A1 | 1/2016 | Pi |
| 2016/0026768 A1 | 1/2016 | Singh et al. |
| 2016/0034961 A1 | 2/2016 | May et al. |
| 2016/0057595 A1 | 2/2016 | Ahmed et al. |
| 2016/0142894 A1 | 5/2016 | Papakonstantinou et al. |
| 2016/0173689 A1 | 6/2016 | Klaban |
| 2016/0210581 A1 | 7/2016 | Braun |
| 2016/0219084 A1 | 7/2016 | Abiezzi |
| 2016/0219397 A1 | 7/2016 | Mayor et al. |
| 2016/0227589 A1 | 8/2016 | Marshall et al. |
| 2016/0269535 A1 | 9/2016 | Balabhadruni et al. |
| 2016/0307436 A1 | 10/2016 | Nixon |
| 2016/0315923 A1 | 10/2016 | Riscombe-Burton et al. |
| 2016/0316493 A1 | 10/2016 | Davis et al. |
| 2016/0337828 A1* | 11/2016 | Michaelis ............ G06N 5/045 |
| 2016/0337831 A1 | 11/2016 | Piett et al. |
| 2016/0345171 A1 | 11/2016 | Kulkarni et al. |
| 2016/0353262 A1 | 12/2016 | Acevedo et al. |
| 2016/0353266 A1* | 12/2016 | Winkler ................ H04W 4/90 |
| 2016/0363931 A1 | 12/2016 | Yang et al. |
| 2017/0004427 A1 | 1/2017 | Bruchal et al. |

(56) References Cited

U.S. PATENT DOCUMENTS

| | | |
|---|---|---|
| 2017/0012815 A1 | 1/2017 | Nekrestyanov et al. |
| 2017/0046216 A1 | 2/2017 | Stenneth et al. |
| 2017/0075407 A1 | 3/2017 | Kritt et al. |
| 2017/0099579 A1 | 4/2017 | Ryan et al. |
| 2017/0124670 A1 | 5/2017 | Becker et al. |
| 2017/0124852 A1 | 5/2017 | Pauws et al. |
| 2017/0140637 A1 | 5/2017 | Thurlow et al. |
| 2017/0142568 A1 | 5/2017 | Saito et al. |
| 2017/0150335 A1* | 5/2017 | Self .................. H04M 3/42357 |
| 2017/0161614 A1 | 6/2017 | Mehta et al. |
| 2017/0180963 A1 | 6/2017 | Cavendish et al. |
| 2017/0180964 A1* | 6/2017 | Mehta .................. H04W 64/00 |
| 2017/0180966 A1 | 6/2017 | Piett et al. |
| 2017/0213251 A1 | 7/2017 | Nunally et al. |
| 2017/0238129 A1 | 8/2017 | Maier et al. |
| 2017/0238136 A1 | 8/2017 | Smith |
| 2017/0245113 A1 | 8/2017 | Hooker |
| 2017/0287085 A1 | 10/2017 | Smith et al. |
| 2017/0310827 A1 | 10/2017 | Mehta et al. |
| 2017/0316698 A1 | 11/2017 | Stenneth et al. |
| 2017/0323209 A1 | 11/2017 | Rinzler et al. |
| 2017/0325056 A1 | 11/2017 | Mehta et al. |
| 2017/0359712 A1 | 12/2017 | Meredith et al. |
| 2018/0020091 A1 | 1/2018 | Self et al. |
| 2018/0039737 A1 | 2/2018 | Dempers et al. |
| 2018/0053401 A1 | 2/2018 | Martin et al. |
| 2018/0077282 A1 | 3/2018 | Herron et al. |
| 2018/0077553 A1 | 3/2018 | Gideon, III |
| 2018/0160267 A1 | 6/2018 | Immendorf et al. |
| 2018/0262544 A1 | 9/2018 | Mehta et al. |
| 2018/0352408 A1 | 12/2018 | Baer et al. |
| 2019/0020993 A1 | 1/2019 | Nguyen |
| 2019/0073894 A1 | 3/2019 | Mehta et al. |
| 2019/0104395 A1 | 4/2019 | Mehta et al. |
| 2019/0130719 A1 | 5/2019 | D'Amico |
| 2019/0166480 A1 | 5/2019 | Rauner |
| 2019/0174288 A1 | 6/2019 | Bozik et al. |
| 2019/0174289 A1 | 6/2019 | Martin et al. |
| 2019/0253861 A1 | 8/2019 | Horelik et al. |
| 2019/0306664 A1 | 10/2019 | Mehta et al. |
| 2019/0320310 A1 | 10/2019 | Horelik et al. |
| 2019/0380020 A1 | 12/2019 | Pellegrini et al. |
| 2020/0100084 A1 | 3/2020 | Martin et al. |
| 2020/0126174 A1 | 4/2020 | Halse et al. |
| 2020/0314623 A1 | 10/2020 | Pellegrini et al. |
| 2021/0006961 A1 | 1/2021 | King-Berkman et al. |
| 2021/0037368 A1 | 2/2021 | Leavitt et al. |

FOREIGN PATENT DOCUMENTS

| | | |
|---|---|---|
| CA | 2773749 A1 | 10/2012 |
| CA | 2773881 A1 | 10/2012 |
| CA | 2790501 A1 | 3/2013 |
| CA | 2809421 A1 | 9/2013 |
| CA | 2646607 C | 9/2016 |
| CA | 2886535 A1 | 10/2016 |
| CA | 2697986 C | 5/2018 |
| CN | 106021508 A | 10/2016 |
| JP | 2012222443 A | 11/2012 |
| KR | 20090019606 A | 2/2009 |
| KR | 20090092900 A | 9/2009 |
| KR | 20100055746 A | 5/2010 |
| KR | 101305286 B1 | 9/2013 |
| KR | 20140052780 A | 5/2014 |
| KR | 20140093568 A | 7/2014 |
| KR | 20150097031 A | 8/2015 |
| KR | 101602482 B1 | 3/2016 |
| KR | 101612423 B1 | 4/2016 |
| KR | 20160097933 A | 8/2016 |
| KR | 20170100422 A | 9/2017 |
| WO | WO-0022593 A1 | 4/2000 |
| WO | WO-0167419 A2 | 9/2001 |
| WO | WO-2007109599 A2 | 12/2007 |
| WO | WO-2012129561 A1 | 9/2012 |
| WO | WO-2014025563 A1 | 2/2014 |
| WO | WO-2014063121 A1 | 4/2014 |
| WO | WO-2014074420 A1 | 5/2014 |
| WO | WO-2014176646 A1 | 11/2014 |
| WO | WO-2015127867 A1 | 9/2015 |
| WO | WO-2015196155 A1 | 12/2015 |
| WO | WO-2016044540 A1 | 3/2016 |
| WO | WO-2017079354 A1 | 5/2017 |
| WO | WO-2017083571 A1 | 5/2017 |
| WO | WO-2017100220 A1 | 6/2017 |
| WO | WO-2017106775 A1 | 6/2017 |
| WO | WO-2017112820 A1 | 6/2017 |
| WO | WO-2017189610 A2 | 11/2017 |
| WO | WO-2017196753 A1 | 11/2017 |
| WO | WO-2018039142 A1 | 3/2018 |
| WO | WO-2019113129 A1 | 6/2019 |
| WO | WO-2020205033 A1 | 10/2020 |

OTHER PUBLICATIONS

Chohlaswood et al. Mining 911 Calls in New York City: Temporal Patterns, Detection and Forecasting. AAAI Conference on Artificial Intelligence Workshop (Apr. 2015).

Chowdhury et al. Tweet4act: Using incident-specific profiles for classifying crisis-related messages. Proceedings of the 10th International ISCRAM Conference (pp. 834-839) (2013).

Hodgkiss et al. Spatiotemporal Analysis of 911 Call Stream Data. Proceedings of the 2005 national conference on Digital government research (2005).

Homeland Security Science and Technology. Using Social Media for Enhanced Situational Awareness and Decision Support. Virtual Social Medial Working Group and DHS First Responders Group. (44 pgs.) (Jun. 2014).

Jasso et al. Prediction of 911 Call Volumes For Emergency Event Detection. Proceedings of the 8th Annual International Digital Government Research Conference (2007).

Marcus et al. TwitInfo: Aggregating and Visualizing Microblogs for Event Exploration. ACM CHI Conference 2011 May 7-12, 2011 (10 pgs).

Meier. MatchApp: Next Generation Disaster Response App? iRevolution (12 pgs.) (Feb. 27, 2013).

National Emergency No. Association (NENA). Social Networking in 9-1-1 PSAPs Information Document. Available at https://c.ymcdn.com/sites/www.nena.org/resource/resmgr/Standards/NENA-INF-001.1.1-2012_Social (18 pgs) (May 8, 2012).

PCT/US2017/029465 International Search Report and Written Opinion dated Aug. 9, 2017.

PCT/US2018/063935 International Search Report and Written Opinion dated Mar. 22, 2019.

PCT/US2019/027538 International Search Report and Written Opinion dated Aug. 2, 2019.

U.S. Appl. No. 16/209,892 Office Action dated Feb. 8, 2019.
U.S. Appl. No. 16/271,634 Office Action dated Dec. 16, 2019.
U.S. Appl. No. 16/271,634 Office Action dated Jun. 13, 2019.
U.S. Appl. No. 16/384,600 Office Action dated Apr. 2, 2020.
U.S. Appl. No. 16/421,355 Office Action dated Feb. 4, 2020.
U.S. Appl. No. 16/436,810 Office Action dated Aug. 9, 2019.
U.S. Appl. No. 16/436,810 Office Action dated Dec. 17, 2019.
U.S. Appl. No. 16/526,195 Office Action dated Dec. 27, 2019.
U.S. Appl. No. 16/740,207 Office Action dated Mar. 11, 2020.

PCT/US2020/013176 International Search Report and Written Opinion dated May 8, 2020.

Song. Next Generation Emergency Call System with Enhanced Indoor Positioning, Columbia University. Thesis [online] [retrieved Apr. 20, 2020 from<url:https://scholar.google.co.kr/citations/?user=h_4uUqAAAAAJ&hl=ko (156 pgs) (2014)</url:<a>.

U.S. Appl. No. 16/384,600 Office Action dated Oct. 2, 2020.
U.S. Appl. No. 16/740,207 Office Action dated Aug. 17, 2020.

PCT/US2019/036403 International Search Report and Written Opinion dated Oct. 4, 2019.

(56) References Cited

OTHER PUBLICATIONS

U.S. Appl. No. 16/378,363 Office Action dated Feb. 17, 2021.
U.S. Appl. No. 16/684,366 Office Action dated Dec. 23, 2020.
U.S. Appl. No. 17/115,098 Office Action dated Mar. 9, 2021.

* cited by examiner

SYSTEMS AND METHODS FOR EMERGENCY DATA INTEGRATION

CROSS-REFERENCE

The present application claims priority to U.S. Provisional Patent Application No. 62/826,680, filed Mar. 29, 2019, entitled "SYSTEMS AND USER INTERFACES FOR EMERGENCY DATA INTEGRATION", which is hereby incorporated by reference herein in its entirety.

BACKGROUND OF THE INVENTION

A person in an emergency situation may request help using a mobile communication device such as a cell phone to dial a designated emergency number like 9-1-1 or a direct access phone number for the local emergency service provider (e.g., a public safety answering point (PSAP), or an emergency dispatch center). This call is assigned to one or more first responders by the emergency service provider. However, these communications are typically limited to audio calls with narrow functionality because most emergency service providers that receive emergency calls currently lack the capacity for more sophisticated communications. In some instances, location determination is possible with the use of adjacent cellular towers, however, the determination often lacks the precision required to enable a rapid emergency response. Accordingly, emergency service providers are typically limited to verbally receiving emergency locations from the person in the emergency during the emergency call. Unfortunately, there are a great many instances in which a person in an emergency does not know or is otherwise incapable of articulating their location.

SUMMARY OF THE INVENTION

One advantage provided by the systems, servers, devices, methods, and media of the instant application is the ability to gather and deliver device-based hybrid locations (hereinafter, "enhanced locations") and additional data that may be pertinent to emergency situations to emergency service providers (ESPs; e.g., public safety answering points, fire departments, police departments, paramedics, police officers, etc.). In some embodiments, an emergency management system (EMS) includes a clearinghouse (also referred to as an "Emergency Clearinghouse") that functions to receive enhanced locations (e.g., global positioning systems location data, map data) and additional data (e.g., medical history, video feeds, emergency reports, media reports) from various sources (e.g., medical databases, mobile devices of public or first responders, public cameras, police systems, media outlets) and at various times before, during, or after emergency situations and distribute enhanced locations and additional data to ESPs to aid the ESPs in responding to live emergency situations. In some embodiments, the enhanced locations and additional data are delivered by the EMS to a public safety answering point (PSAP). In some embodiments, the enhanced locations and additional data are displayed within a preexisting PSAP system, such as an Automatic Location Identification (ALI) display. In some embodiments, the enhanced locations and additional data are displayed through a graphical user interface provided by an emergency response application separate from the preexisting ESP system (e.g., PSAP system).

The benefits of the systems, applications, servers, devices, methods, and media of the instant application are numerous. Firstly, the emergency response application provides the PSAP with critical information to aid in the response to a given emergency. In the case of location data, the PSAP is enabled to verify the location of the emergency with the caller, rather than relying on the distressed caller to generate the location data. Thus, the PSAP can initiate a response before the user provides the location data, saving seconds or minutes on response time. Secondly, there is currently no mechanism for communicating third party enhanced location data and/or additional data to a PSAP with speed and efficiency. The systems, applications, servers, devices, methods, and media of the instant application allow for the communication of enhanced location data and additional data to the PSAP through a standalone emergency response application accessible by PSAP personnel, or as a software integration of the data pipeline with preexisting ESP systems. Disclosed herein are systems, applications, servers, devices, methods, and media that automatically push data to the PSAP, which is particularly beneficial because it streamlines the emergency response without requiring active input from the PSAP personnel.

Another advantage provided by the systems, servers, devices, methods, and media of the instant application is the ability to access an emergency response application provided to authorized emergency service providers (e.g., PSAPs) for receiving and displaying emergency data, such as enhanced locations. In some embodiments, the emergency response application functions to verify emergency service providers, generate emergency data requests, and display emergency data received from the Emergency Clearinghouse, as described below. In some embodiments, the emergency response application provides a graphical user interface to a computing device that is accessible by members of emergency service providers. In some embodiments, the emergency response application integrates with one or more preexisting ESP systems to provide a seamless and comprehensive emergency data delivery system.

Yet another advantage provided by the systems, servers, devices, methods and media of the instant application is the ability to protect potentially sensitive emergency data using geospatial analysis. In some embodiments, the Emergency Clearinghouse and the emergency response application use geofences to limit the delivery of emergency data to geographically appropriate recipients. In some embodiments, geofences are received from PSAP administrators through the emergency response application, such as by a PSAP administrator defining a jurisdiction of a particular PSAP within a map displayed within a graphical user interface provided by the emergency response application, as described below. In some embodiments, geofences received from PSAP administrators must be verified by public safety officials before the geofences are applied within the Emergency Clearinghouse and emergency response application.

An additional advantage provided by the systems, applications, servers, devices, methods, and media of the instant application is the ability to access a jurisdictional awareness view within the emergency response application. In some embodiments, the jurisdictional awareness view enables an ESP (e.g., a PSAP) to view ongoing and optionally recently received emergency alerts within one or more geofenced jurisdictions. In some embodiments, the jurisdictional awareness view displays an incident queue (also referred to as a "list of incidents") with numerous incidents associated with a device identifier and a location for each emergency alert. In some embodiments, the location associated with an incident is updated in real time. In some embodiments, the jurisdictional awareness view displays the location of available emergency services within a variable proximity to a location associated with an incident. In some embodiments, the ESP is enabled to coordinate the dispatch of emergency responders to emergency callers, so as to reduce response times and improve the allocation of resources.

Disclosed herein, in one aspect, is an emergency management system (EMS) configured for providing emergency data to an emergency service provider (ESP), the EMS comprising a memory, a network component, and at least one processor operatively coupled to the network component, the at least one processor operative to: a) detect an active communication link established between the EMS and a first ESP through an emergency response application executed on a computing device at the first ESP; b) transmit a third-party query comprising an identifier of the first ESP to a third-party server; c) receive emergency data tagged with the identifier of the first ESP from the third-party server, wherein the emergency data comprises a device identifier and an emergency location associated with the device identifier; d) in response to detecting the active communication link between the EMS and the first ESP and receiving the emergency data tagged with the identifier of the first ESP, transmit the emergency data comprising the device identifier and the emergency location to the first ESP for display within the emergency response application. In some embodiments, the emergency response application comprises a graphical user interface (GUI) displaying an interactive map and wherein the emergency location is displayed within the interactive map. In some embodiments, the emergency data tagged with the identifier of the first ESP further comprises medical data. In some embodiments, the emergency data tagged with the identifier of the first ESP further comprises sensor data. In some embodiments, the emergency location was received by the third-party server within an emergency alert and wherein the emergency data tagged with the identifier of the first ESP further comprises emergency data associated with a plurality of emergency alerts. In some embodiments, the at least one processor is operative to transmit the third-party query comprising the identifier of the first ESP to the third-party server in response to detecting the active communication link established between the EMS and the emergency response application. In some embodiments, the at least one processor is further operative to periodically transmit subsequent third-party queries comprising the identifier of the first ESP to the third-party server. In some embodiments, the at least one processor is further operative to periodically transmit the subsequent third-party queries to the third-party server for the duration of the active communication link established between the EMS and the first ESP through the emergency response application. In some embodiments, the computing device comprises a memory, a user interface, a network component, a display, and at least one processor operatively coupled to the network component, the at least one processor operative to: a) provide the emergency response application, the emergency response application comprising a graphical user interface (GUI) displaying an interactive map; b) receive the emergency location tagged with the identifier of the first ESP; and c) display the emergency location within the interactive map of the emergency response application. In some embodiments, the emergency response application is a web application accessed through a web browser installed on the computing device at the first ESP. In some embodiments, the emergency response application is a software application installed on the computing device at the first ESP. In some embodiments, the at least one processor is further operative to: a) detect a second active communication link established between the EMS and a second ESP through an emergency response application executed on a computing device at the second ESP; b) transmit a third-party query comprising an identifier of the second ESP to a third-party server; c) receive emergency data tagged with the identifier of the second ESP from the third-party server, wherein the emergency data comprises a device identifier and an emergency location associated with the device identifier; d) in response to detecting the second active communication link between the EMS and the second ESP and receiving the emergency data tagged with the identifier of the second ESP, transmit the emergency data comprising the device identifier and the emergency location to the second ESP for display within the emergency response application executed on the computing device at the second ESP.

Disclosed herein, in one aspect, is non-transitory, non-volatile, computer readable storage media encoded with instructions executable by at least one processor, that when executed cause the processor to: a) detect an active communication link established between the EMS and a first ESP through an emergency response application executed on a computing device at the first ESP; b) transmit a third-party query comprising an identifier of the first ESP to a third-party server; c) receive emergency data tagged with the identifier of the first ESP from the third-party server, wherein the emergency data comprises a device identifier and an emergency location associated with the device identifier; d) in response to detecting the active communication link between the EMS and the first ESP and receiving the emergency data tagged with the identifier of the first ESP, transmit the emergency data comprising the device identifier and the emergency location to the first ESP for display within the emergency response application. In some embodiments, the emergency response application comprises a graphical user interface (GUI) displaying an interactive map and wherein the emergency location is displayed within the interactive map. In some embodiments, the emergency data tagged with the identifier of the first ESP further comprises medical data. In some embodiments, the emergency data tagged with the identifier of the first ESP further comprises sensor data. In some embodiments, the emergency location was received by the third-party server within an emergency alert and wherein the emergency data tagged with the identifier of the first ESP further comprises emergency data associated with a plurality of emergency alerts. In some embodiments, the at least one processor is operative to transmit the third-party query comprising the identifier of the first ESP to the third-party server in response to detecting the active communication link established between the EMS and the emergency response application. In some embodiments, the at least one processor is further operative to periodically transmit subsequent third-party queries comprising the identifier of the first ESP to the third-party server. In some embodiments, the at least one processor is further operative to periodically transmit the subsequent third-party queries to the third-party server for the duration of the active communication link established between the EMS and the first ESP through the emergency response application. In some embodiments, the computing device comprises a memory, a user interface, a network component, a display, and at least one processor operatively coupled to the network component, the at least one processor operative to: a) provide the emergency response application, the emergency response application comprising a graphical user interface (GUI) displaying an interactive map; b) receive the emergency location tagged with the identifier of the first ESP; and c) display the emergency location within the interactive map of the emergency response application. In some embodiments, the emergency response application is a web application accessed through a web browser installed on the computing device at the first ESP. In some embodiments, the emergency response application is a software application installed on the computing device at the first ESP. In some embodiments, the at least one processor is further operative to: a) detect a second active communication link established between the EMS and a second ESP through an emergency response application executed on a computing device at the second ESP; b) transmit a third-party query comprising an identifier of the second ESP to a third-party server; c) receive emergency data tagged with the identifier of the second ESP from the third-party server, wherein the emergency data comprises a device identifier and an emergency location associated with the device identifier; d) in response to detecting the second active communication link between the EMS and the second ESP and receiving the emergency data tagged with the identifier of the second ESP, transmit the emergency data comprising the device identifier and the emergency location to the second ESP for display within the emergency response application executed on the computing device at the second ESP.

Disclosed herein, in one aspect, is a computer-implemented method comprising: a) detecting an active communication link established between the EMS and a first ESP through an emergency response application executed on a computing device at the first ESP; b) transmitting a third-party query comprising an identifier of the first ESP to a third-party server; c) receiving emergency data tagged with the identifier of the first ESP from the third-party server, wherein the emergency data comprises a device identifier and an emergency location associated with the device identifier; d) in response to detecting the active communication link between the EMS and the first ESP and receiving the emergency data tagged with the identifier of the first ESP, transmitting the emergency data comprising the device identifier and the emergency location to the first ESP for display within the emergency response application. In some embodiments, the emergency response application comprises a graphical user interface (GUI) displaying an interactive map and wherein the emergency location is displayed within the interactive map. In some embodiments, the emergency data tagged with the identifier of the first ESP further comprises medical data. In some embodiments, the emergency data tagged with the identifier of the first ESP further comprises sensor data. In some embodiments, the emergency location was received by the third-party server within an emergency alert and wherein the emergency data tagged with the identifier of the first ESP further comprises emergency data associated with a plurality of emergency alerts. In some embodiments, the method comprises transmitting the third-party query comprising the identifier of the first ESP to the third-party server in response to detecting the active communication link established between the EMS and the emergency response application. In some embodiments, the method comprises periodically transmitting subsequent third-party queries comprising the identifier of the first ESP to the third-party server. In some embodiments, the method comprises periodically transmitting the subsequent third-party queries to the third-party server for the duration of the active communication link established between the EMS and the first ESP through the emergency response application. In some embodiments, the computing device comprises a memory, a user interface, a network component, a display, and at least one processor operatively coupled to the network component, the at least one processor operative to: a) provide the emergency response application, the emergency response application comprising a graphical user interface (GUI) displaying an interactive map; b) receive the emergency location tagged with the identifier of the first ESP; and c) display the emergency location within the interactive map of the emergency response application. In some embodiments, the emergency response application is a web application accessed through a web browser installed on the computing device at the first ESP. In some embodiments, the emergency response application is a software application installed on the computing device at the first ESP. In some embodiments, the method comprises: a) detecting a second active communication link established between the EMS and a second ESP through an emergency response application executed on a computing device at the second ESP; b) transmitting a third-party query comprising an identifier of the second ESP to a third-party server; c) receiving emergency data tagged with the identifier of the second ESP from the third-party server, wherein the emergency data comprises a device identifier and an emergency location associated with the device identifier; d) in response to detecting the second active communication link between the EMS and the second ESP and receiving the emergency data tagged with the identifier of the second ESP, transmitting the emergency data comprising the device identifier and the emergency location to the second ESP for display within the emergency response application executed on the computing device at the second ESP.

Disclosed herein, in another aspect, is an emergency management system (EMS) configured for providing emergency data to requesting parties, the EMS comprising a memory a network component, and at least one processor operatively coupled to the network component, the at least one processor operative to: a) receive an emergency alert comprising a device identifier and an emergency location associated with the device identifier from an electronic device; b) access one or more geofences associated with one or more emergency service providers (ESPs) from a plurality of geofences, the one or more geofences comprising a first geofence associated with a first ESP; c) determine that the emergency location is within the first geofence associated with the first ESP; d) in response to determining that the emergency location is within the first geofence associated with the first ESP, tag emergency data comprising the device identifier and emergency location with an identifier of the first ESP; e) receive an emergency data request comprising the identifier of the first ESP from a third-party emergency management system (EMS), wherein the third party EMS is communicatively coupled to the first ESP; and f) transmit the emergency data comprising the device identifier and the emergency location tagged with the identifier of the first ESP to the third party EMS for transmission to the first ESP. In some embodiments, the third party EMS is communicatively coupled to the first ESP through an emergency response application executed on a computing device at the first ESP. In some embodiments, the emergency response application comprises a graphical user interface (GUI) displaying an interactive map. In some embodiments, the emergency location is displayed within the interactive map. In some embodiments, the emergency data tagged with the identifier of the first ESP further comprises medical data. In some embodiments, the emergency data tagged with the identifier of the first ESP further comprises sensor data. In some embodiments, the emergency data tagged with the identifier of the first ESP comprises additional data from the emergency alert. In some embodiments, the emergency data tagged with the identifier of the first ESP further comprises emergency data associated with a plurality of emergency alerts. In some embodiments, the emergency data request further comprises an emergency data type indicating the type of emergency data being requested. In some embodiments, the at least one processor is further configured to: a) receive a second emergency data request comprising the identifier of the first ESP from the third party EMS; b) retrieve updated emergency data tagged with the identifier of the first ESP; and c) transmit the updated emergency data tagged with the identifier of the first ESP to the third party EMS for transmission to the first ESP. In some embodiments, the at least one processor is further configured to: a) receive a second emergency alert comprising a second device identifier and a second emergency location associated with the second device identifier from a second electronic device; b) access one or more geofences associated with one or more emergency service providers (ESPs) from the plurality of geofences, the one or more geofences comprising a second geofence associated with a second ESP; c) determine that the second emergency location is within the second geofence associated with the second ESP; d) in response to determining that the second emergency location is within the second geofence associated with the second ESP, tag emergency data comprising the second device identifier and second emergency location with an identifier of the second ESP; e) receive a second emergency data request comprising the second identifier of the second ESP from the third-party emergency management system (EMS), wherein the third-party EMS is communicatively coupled to the second ESP; and f) transmit the emergency data comprising the second device identifier and the second emergency location tagged with the identifier of the second ESP to the third-party EMS for transmission to the second ESP. In some embodiments, the third-party EMS is communicatively coupled to a plurality of emergency service providers (ESPs) comprising the first ESP. In some embodiments, the EMS is communicatively coupled to a second third-party emergency management system (EMS). In some embodiments, the second third-party EMS is communicatively coupled to a plurality of ESPs.

Disclosed herein, in one aspect, is non-transitory, non-volatile, computer readable storage media encoded with instructions executable by at least one processor, that when executed cause the processor to: a) receive an emergency alert comprising a device identifier and an emergency location associated with the device identifier from an electronic device; b) access one or more geofences associated with one or more emergency service providers (ESPs) from a plurality of geofences, the one or more geofences comprising a first geofence associated with a first ESP; c) determine that the emergency location is within the first geofence associated with the first ESP; d) in response to determining that the emergency location is within the first geofence associated with the first ESP, tag emergency data comprising the device identifier and emergency location with an identifier of the first ESP; e) receive an emergency data request comprising the identifier of the first ESP from a third-party emergency management system (EMS), wherein the third party EMS is communicatively coupled to the first ESP; and f) transmit the emergency data comprising the device identifier and the emergency location tagged with the identifier of the first ESP to the third party EMS for transmission to the first ESP. In some embodiments, the third party EMS is communicatively coupled to the first ESP through an emergency response application executed on a computing device at the first ESP. In some embodiments, the emergency response application comprises a graphical user interface (GUI) displaying an interactive map. In some embodiments, the emergency location is displayed within the interactive map. In some embodiments, the emergency data tagged with the identifier of the first ESP further comprises medical data. In some embodiments, the emergency data tagged with the identifier of the first ESP further comprises sensor data. In some embodiments, the emergency data tagged with the identifier of the first ESP comprises additional data from the emergency alert. In some embodiments, the emergency data tagged with the identifier of the first ESP further comprises emergency data associated with a plurality of emergency alerts. In some embodiments, the emergency data request further comprises an emergency data type indicating the type of emergency data being requested. In some embodiments, the at least one processor is further configured to: a) receive a second emergency data request comprising the identifier of the first ESP from the third party EMS; b) retrieve updated emergency data tagged with the identifier of the first ESP; and c) transmit the updated emergency data tagged with the identifier of the first ESP to the third party EMS for transmission to the first ESP. In some embodiments, the instructions further cause the processor to: a) receive a second emergency alert comprising a second device identifier and a second emergency location associated with the second device identifier from a second electronic device; b) access one or more geofences associated with one or more emergency service providers (ESPs) from the plurality of geofences, the one or more geofences comprising a second geofence associated with a second ESP; c) determine that the second emergency location is within the second geofence associated with the second ESP; d) in response to determining that the second emergency location is within the second geofence associated with the second ESP, tag emergency data comprising the second device identifier and second emergency location with an identifier of the second ESP; e) receive a second emergency data request comprising the second identifier of the second ESP from the third-party emergency management system (EMS), wherein the third-party EMS is communicatively coupled to the second ESP; and f) transmit the emergency data comprising the second device identifier and the second emergency location tagged with the identifier of the second ESP to the third-party EMS for transmission to the second ESP. In some embodiments, the third-party EMS is communicatively coupled to a plurality of emergency service providers (ESPs) comprising the first ESP. In some embodiments, the EMS is communicatively coupled to a second third-party emergency management system (EMS). In some embodiments, the second third-party EMS is communicatively coupled to a plurality of ESPs.

Disclosed herein, in another aspect, is a computer-implemented method comprising: a) receiving an emergency alert comprising a device identifier and an emergency location associated with the device identifier from an electronic device; b) accessing one or more geofences associated with one or more emergency service providers (ESPs) from a plurality of geofences, the one or more geofences comprising a first geofence associated with a first ESP; c) determining that the emergency location is within the first geofence associated with the first ESP; d) in response to determining that the emergency location is within the first geofence associated with the first ESP, tagging emergency data comprising the device identifier and emergency location with an identifier of the first ESP; e) receive an emergency data request comprising the identifier of the first ESP from a third-party emergency management system (EMS), wherein the third party EMS is communicatively coupled to the first ESP; and f) transmitting the emergency data comprising the device identifier and the emergency location tagged with the identifier of the first ESP to the third party EMS for transmission to the first ESP. In some embodiments, the third party EMS is communicatively coupled to the first ESP through an emergency response application executed on a computing device at the first ESP. In some embodiments, the emergency response application comprises a graphical user interface (GUI) displaying an interactive map. In some embodiments, the emergency location is displayed within the interactive map. In some embodiments, the emergency data tagged with the identifier of the first ESP further comprises medical data. In some embodiments, the emergency data tagged with the identifier of the first ESP further comprises sensor data. In some embodiments, the emergency data tagged with the identifier of the first ESP comprises additional data from the emergency alert. In some embodiments, the emergency data tagged with the identifier of the first ESP further comprises emergency data associated with a plurality of emergency alerts. In some embodiments, the emergency data request further comprises an emergency data type indicating the type of emergency data being requested. In some embodiments, the method further comprises: a) receiving a second emergency data request comprising the identifier of the first ESP from the third party EMS; b) retrieving updated emergency data tagged with the identifier of the first ESP; and c) transmitting the updated emergency data tagged with the identifier of the first ESP to the third party EMS for transmission to the first ESP. In some embodiments, the method further comprises: a) receiving a second emergency alert comprising a second device identifier and a second emergency location associated with the second device identifier from a second electronic device; b) accessing one or more geofences associated with one or more emergency service providers (ESPs) from the plurality of geofences, the one or more geofences comprising a second geofence associated with a second ESP; c) determining that the second emergency location is within the second geofence associated with the second ESP; d) in response to determining that the second emergency location is within the second geofence associated with the second ESP, tagging emergency data comprising the second device identifier and second emergency location with an identifier of the second ESP; e) receiving a second emergency data request comprising the second identifier of the second ESP from the third-party emergency management system (EMS), wherein the third-party EMS is communicatively coupled to the second ESP; and f) transmitting the emergency data comprising the second device identifier and the second emergency location tagged with the identifier of the second ESP to the third-party EMS for transmission to the second ESP. In some embodiments, the third-party EMS is communicatively coupled to a plurality of emergency service providers (ESPs) comprising the first ESP. In some embodiments, the EMS is communicatively coupled to a second third-party emergency management system (EMS). In some embodiments, the second third-party EMS is communicatively coupled to a plurality of ESPs.

Disclosed herein, in another aspect, is a system comprising: a) a first emergency management system (EMS) configured for providing emergency data to requesting parties, the first EMS comprising a memory, a network component, and at least one processor operatively coupled to the network component, the at least one processor operative to: i) receive an emergency alert comprising an emergency location from an electronic device; ii) automatically access one or more geofences associated with one or more emergency service providers (ESPs) from a geofence database, the one or more geofences comprising a first geofence associated with a first ESP; iii) determine that the emergency location is within the first geofence associated with the first ESP; iv) in response to determining that the emergency location is within the first geofence associated with the first ESP, tag the location with an identifier of the first ESP; v) receive an emergency data request comprising the identifier of the first ESP from a second emergency management system (EMS), wherein the second EMS is communicatively coupled to the first ESP; vi) retrieve a first set of emergency data tagged with the identifier of the first ESP, wherein the first set of emergency data tagged with the identifier of the first ESP comprises the emergency location; and vii) transmit the first set of emergency data tagged with the identifier of the first ESP to the third party EMS for transmission to the first ESP; b) the second emergency management system (EMS), the second EMS comprising a memory, a network component, and at least one processor operatively coupled to the network component, the at least one processor operative to: i) detect an active communication link established between the second EMS and the first ESP through an emergency response application executed on a computing device at the first ESP; ii) transmit the emergency data request comprising the identifier of the first ESP to the first EMS; iii) receive the first set of emergency data tagged with the identifier of the first ESP from the first EMS; and iv) transmit the first set of emergency data tagged with the identifier of the first ESP to the first ESP for display within a graphical user interface (GUI) of the emergency response application. In some embodiments, the first set of emergency data tagged with the identifier of the first ESP further comprises medical data. In some embodiments, the first set of emergency data tagged with the identifier of the first ESP further comprises an environmental or physiological parameter. In some embodiments, the at least one processor of the second EMS is operative to transmit the emergency data request comprising the identifier of the first ESP to the first EMS in response to detecting the active communication link established between the second EMS and the first ESP through the emergency response application. In some embodiments, the at least one processor of the second EMS is further operative to periodically transmit subsequent emergency data requests comprising the identifier of the first ESP to the first EMS. In some embodiments, the at least one processor of the second EMS is further operative to periodically transmit the subsequent emergency data requests to the first EMS for the duration of the active communication session established between the second EMS and the first ESP through the emergency response application. In some embodiments, the second EMS is communicatively coupled to a plurality of emergency service providers (ESPs) comprising the first ESP. In some embodiments, the first EMS is communicatively coupled to a third emergency management system (EMS). In some embodiments, the third EMS is communicatively coupled to a plurality of ESPs. In some embodiments, the second EMS is communicatively coupled a third EMS communicatively coupled to one or more emergency service providers (ESPs); and the at least one processor of the second EMS is further operative to: i) receive a second emergency data request comprising a device or user identifier from the third EMS; ii) retrieve a second set of emergency data associated with the device or user identifier; and iii) transmit the second set of emergency data associated with the device or user identifier for transmission to a second ESP comprised within the one or more ESPs.

Disclosed herein, in another aspect, is an emergency management system (EMS) comprising a memory, a network component, and at least one processor operatively coupled to the network component, the at least one processor operative to: a) determine an active communication link is established with a computing device providing an emergency response application at a first ESP; b) query a database comprising a plurality of identifiers associated with a plurality of emergency service providers (ESPs) to obtain an identifier associated with the first ESP; c) transmit a third-party query comprising the identifier associated with the first ESP to a third-party server; d) receive emergency data tagged with the identifier of the first ESP from the third-party server, wherein the emergency data comprises a device identifier and an emergency location associated with the device identifier; and e) transmit the emergency data comprising the device identifier and the emergency location to the first ESP through the active communication link with the computing device providing the emergency response application at the first ESP. In some embodiments, the emergency response application comprises a graphical user interface (GUI) displaying an interactive map comprising a visual indicator of the emergency location. In some embodiments, the emergency data tagged with the identifier of the first ESP further comprises medical data. In some embodiments, the emergency data tagged with the identifier of the first ESP further comprises sensor data. In some embodiments, the emergency data tagged with the identifier of the first ESP comprises information associated with a plurality of emergency alerts. In some embodiments, the at least one processor is further operative to periodically transmit subsequent third-party queries comprising the identifier of the first ESP to the third-party server. In some embodiments, the at least one processor is further operative to periodically transmit the subsequent third-party queries to the third-party server for the duration of the active communication link established between the EMS and the first ESP through the emergency response application. In some embodiments, the emergency response application is a web application accessed through a web browser installed on the computing device at the first ESP. In some embodiments, the emergency response application is a software application installed on the computing device at the first ESP. In some embodiments, the at least one processor is further operative to: a) detect an active communication link established with a second ESP through an emergency response application executed on a computing device at the second ESP; b) transmit a third-party query comprising an identifier of the second ESP to a third-party server; c) receive emergency data tagged with the identifier of the second ESP from the third-party server, wherein the emergency data comprises a device identifier and an emergency location associated with the device identifier; d) in response to detecting the active communication link between the EMS and the second ESP and receiving the emergency data tagged with the identifier of the second ESP, transmit the emergency data comprising the device identifier and the emergency location to the second ESP for display within the emergency response application executed on the computing device at the second ESP.

Disclosed herein, in another aspect, is non-transitory, non-volatile, computer readable storage media encoded with instructions executable by at least one processor, that when executed cause the processor to: a) determine an active communication link is established with a computing device providing an emergency response application at a first ESP; b) query a database comprising a plurality of identifiers associated with a plurality of emergency service providers (ESPs) to obtain an identifier associated with the first ESP; c) transmit a third-party query comprising the identifier associated with the first ESP to a third-party server; d) receive emergency data tagged with the identifier of the first ESP from the third-party server, wherein the emergency data comprises a device identifier and an emergency location associated with the device identifier; and e) transmit the emergency data comprising the device identifier and the emergency location to the first ESP through the active communication link with the computing device providing the emergency response application at the first ESP. In some embodiments, the emergency response application comprises a graphical user interface (GUI) displaying an interactive map comprising a visual indicator of the emergency location. In some embodiments, the emergency data tagged with the identifier of the first ESP further comprises medical data. In some embodiments, the emergency data tagged with the identifier of the first ESP further comprises sensor data. In some embodiments, the emergency data tagged with the identifier of the first ESP comprises information associated with a plurality of emergency alerts. In some embodiments, the instructions further cause the processor to periodically transmit subsequent third-party queries comprising the identifier of the first ESP to the third-party server. In some embodiments, the instructions further cause the processor to periodically transmit the subsequent third-party queries to the third-party server for the duration of the active communication link established between the EMS and the first ESP through the emergency response application. In some embodiments, the emergency response application is a web application accessed through a web browser installed on the computing device at the first ESP. In some embodiments, the emergency response application is a software application installed on the computing device at the first ESP. In some embodiments, the instructions further cause the processor to: a) detect an active communication link established with a second ESP through an emergency response application executed on a computing device at the second ESP; b) transmit a third-party query comprising an identifier of the second ESP to a third-party server; c) receive emergency data tagged with the identifier of the second ESP from the third-party server, wherein the emergency data comprises a device identifier and an emergency location associated with the device identifier; d) in response to detecting the active communication link between the EMS and the second ESP and receiving the emergency data tagged with the identifier of the second ESP, transmit the emergency data comprising the device identifier and the emergency location to the second ESP for display within the emergency response application executed on the computing device at the second ESP.

Disclosed herein, in another aspect, is a computer-implemented method comprising: a) determining an active communication link is established with a computing device providing an emergency response application at a first ESP; b) querying a database comprising a plurality of identifiers associated with a plurality of emergency service providers (ESPs) to obtain an identifier associated with the first ESP; c) transmitting a third-party query comprising the identifier associated with the first ESP to a third-party server; d) receiving emergency data tagged with the identifier of the first ESP from the third-party server, wherein the emergency data comprises a device identifier and an emergency location associated with the device identifier; and e) transmitting the emergency data comprising the device identifier and the emergency location to the first ESP through the active communication link with the computing device providing the emergency response application at the first ESP. In some embodiments, the emergency response application comprises a graphical user interface (GUI) displaying an interactive map comprising a visual indicator of the emergency location. In some embodiments, the emergency data tagged with the identifier of the first ESP further comprises medical data. In some embodiments, the emergency data tagged with the identifier of the first ESP further comprises sensor data. In some embodiments, the emergency data tagged with the identifier of the first ESP comprises information associated with a plurality of emergency alerts. In some embodiments, the method comprises periodically transmitting subsequent third-party queries comprising the identifier of the first ESP to the third-party server. In some embodiments, the method comprises periodically transmitting the subsequent third-party queries to the third-party server for the duration of the active communication link established between the EMS and the first ESP through the emergency response application. In some embodiments, the emergency response application is a web application accessed through a web browser installed on the computing device at the first ESP. In some embodiments, the emergency response application is a software application installed on the computing device at the first ESP. In some embodiments, the method further comprises: a) detecting an active communication link established with a second ESP through an emergency response application executed on a computing device at the second ESP; b) transmitting a third-party query comprising an identifier of the second ESP to a third-party server; c) receiving emergency data tagged with the identifier of the second ESP from the third-party server, wherein the emergency data comprises a device identifier and an emergency location associated with the device identifier; d) in response to detecting the active communication link between the EMS and the second ESP and receiving the emergency data tagged with the identifier of the second ESP, transmitting the emergency data comprising the device identifier and the emergency location to the second ESP for display within the emergency response application executed on the computing device at the second ESP.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10 illustrates a graphical user interface for verifying an ESP log-in, in accordance with certain embodiments;

FIG. 15 illustrates additional emergency data displayed within the emergency response application, in accordance with certain embodiments;

DETAILED DESCRIPTION

Electronic Device, Emergency Management System, And Emergency Service Provider

Figure 1A:
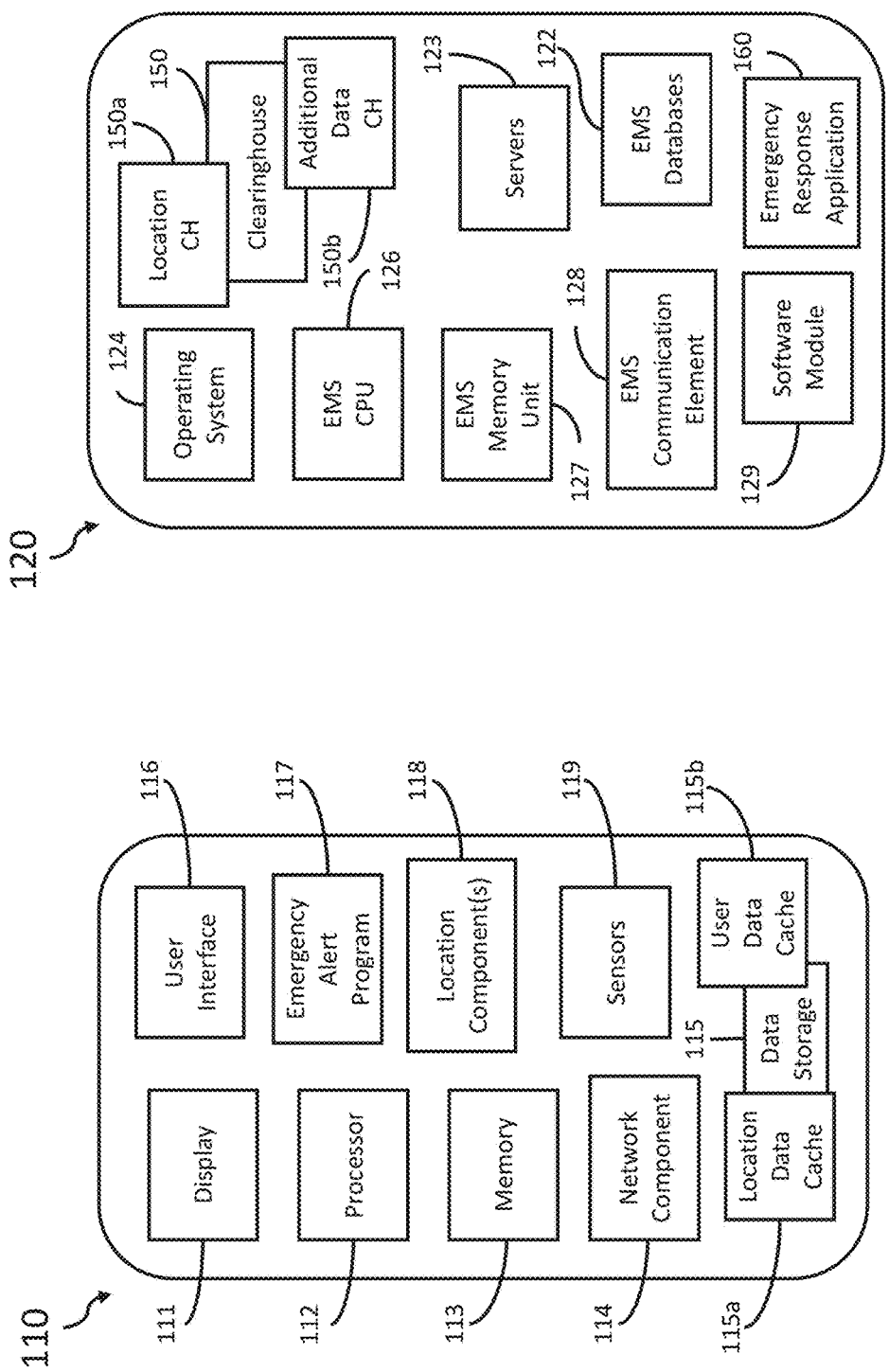
FIG. 1A depicts diagrams of an electronic device and an emergency management system (EMS)

In certain embodiments, disclosed herein are devices, systems, and methods for managing emergency data for emergency response. FIG. 1A depicts diagrams of (i) an electronic device 110 and (ii) an emergency management system (EMS) 120. In some embodiments, the electronic device 110 is a digital processing device such as a communication device (e.g., mobile or cellular phone, computer, laptop, etc.). In some embodiments, the electronic device is a wearable device (e.g., a smartwatch). In some embodiments, the electronic device is an Internet of Things (IoT) device, such as a home assistant (e.g., an Amazon Echo) or a connected smoke detector (e.g., a Nest Protect smoke and carbon monoxide alarm). In some embodiments, the electronic device is a walkie-talkie or two-way radio.

In some embodiments, the electronic device 110 includes a display 111, a processor 112, a memory 113 (e.g., an EPROM memory, a RAM, or a solid-state memory), and several optional components such as one or more network component(s) 114 (e.g., an antenna and associated components, Wi-Fi adapters, Bluetooth adapters, etc.), a data storage 115, a user interface 116, a computer program 117, one or more location components 118, and one or more sensors 119. In some embodiments, the processor 112 is implemented as one or more microprocessors, microcomputers, microcontrollers, digital signal processors, central processing units, state machines, logic circuitries, and/or devices that manipulate signals based on operational instructions. Among other capabilities, the processor 112 is configured to fetch and execute computer-readable instructions stored in the memory 113.

In some embodiments, the display 111 is part of the user interface 116 (e.g., a touchscreen is both a display and a user interface in that it provides an interface to receive user input or user interactions). In some embodiments, the user interface 116 includes physical buttons such as an on/off button or volume buttons. In some embodiments, the display 111 and/or the user interface 116 comprises a touchscreen (e.g., a capacitive touchscreen), which is capable of displaying information and receiving user input. In some embodiments, the user interface 116 does not include a touchscreen, but comprises one or more physical buttons and/or a microphone. In some embodiments, the display 111 does not include a touchscreen, but comprises one or more lights, indicators, and/or lighted buttons.

In some embodiments, the electronic device 110 includes various accessories that allow for additional functionality. In some embodiments, these accessories (not shown) include one or more of the following: a microphone, a camera, speaker, a fingerprint scanner/reader, health or environmental sensors, a USB or micro-USB port, a headphone jack, a card reader, a SIM card slot, or any combination thereof. In some embodiments, the one or more sensors include, but are not limited to: a gyroscope, an accelerometer, a thermometer, a heart rate sensor, a barometer, or a hematology analyzer. In some embodiments, the data storage 115 includes a location data cache 115A and a user data cache 115B. In some embodiments, the location data cache 115A is configured to store locations generated by the one or more location components 118.

In some embodiments, the computer program 117 is an emergency response application or emergency response mobile application. In some embodiments, the computer program 117 is configured to record user data, such as a name, address, or medical data of a user associated with the electronic device 110. In some embodiments, the computer program 117 is an emergency alert program configured to detect an emergency from the electronic device 110 (e.g., when a user 100 (not shown) uses the electronic device 110 to make an emergency call).

It is contemplated that the electronic device may be a triggering device where the emergency alert is triggered by a user input or sensor readings. In some embodiments, the user 100 initiates the emergency alert by interacting with the user interface 116. In some embodiments, the emergency is detected by one or more sensors (built in or peripheral to the device 110). In some embodiments, in response to detecting an emergency request for assistance (e.g., a native dial 9-1-1 call) generated or sent by the electronic device 110, the computer program is configured to deliver an emergency notification to the EMS 120.

In some embodiments, the emergency notification is an HTTP post or another type of Internet-based message containing information regarding the emergency request. In some embodiments, the emergency notification is an SMS message (data or text), a multimedia message, etc. In some embodiments, the emergency notification includes a location (e.g., a device-based hybrid location) generated by or for the electronic device 110, which may be current or historical location. In some embodiments, in response to detecting an emergency request generated or sent by the electronic device 110, the computer program is configured to deliver user data to the emergency management system (EMS) 120. In some embodiments, the current location is not more than 30 minutes, 1 hour, 2 hours or 24 hours old.

In some embodiments, as depicted in FIG. 1A, the emergency management system (EMS) 120 includes an EMS operating system 124, an EMS CPU 126, an EMS memory unit 127, an EMS communication element 128, and one or more software modules 129. In some embodiments, the EMS CPU 126 is implemented as one or more microprocessors, microcomputers, microcontrollers, digital signal processors, central processing units, state machines, logic circuitries, and/or devices that manipulate signals based on operational instructions. Among other capabilities, the EMS CPU 126 is configured to fetch and execute computer-readable instructions stored in the EMS memory unit 127. The EMS memory unit 127 optionally includes any computer-readable medium known in the art including, for example, volatile memory, such as static random-access memory (SRAM) and dynamic random-access memory (DRAM), and/or non-volatile memory, such as read-only memory (ROM), erasable programmable ROM, flash memories, hard disks, optical disks, and magnetic tapes. The EMS memory unit 127 optionally includes modules, routines, programs, objects, components, data structures, etc., which perform particular tasks or implement particular abstract data types.

In some embodiments, the EMS 120 includes one or more EMS databases 122, one or more servers 123, and a clearinghouse 150. In some embodiments, the clearinghouse 150, as described in further detail below, is an input/output (I/O) interface configured to manage communications and data transfers to and from the EMS 120 and external systems and devices. In some embodiments, the clearinghouse 150 includes a variety of software and hardware interfaces, for example, a web interface, a graphical user interface (GUI), and the like. The clearinghouse 150 optionally enables the EMS 120 to communicate with other computing devices, such as web servers and external data servers (not shown). In some embodiments, the clearinghouse 150 facilitates multiple communications within a wide variety of networks and protocol types, including wired networks, for example, LAN, cable, etc., and wireless networks, such as WLAN, cellular, or satellite. In some embodiments, the clearinghouse 150 includes one or more ports for connecting a number of devices to one another or to another server. In some embodiments, the clearinghouse 150 includes one or more sub-clearinghouses, such as location clearinghouse 150A and additional data clearinghouse 150B, configured to manage the transfer of locations and additional data, respectively.

Figure 1B:
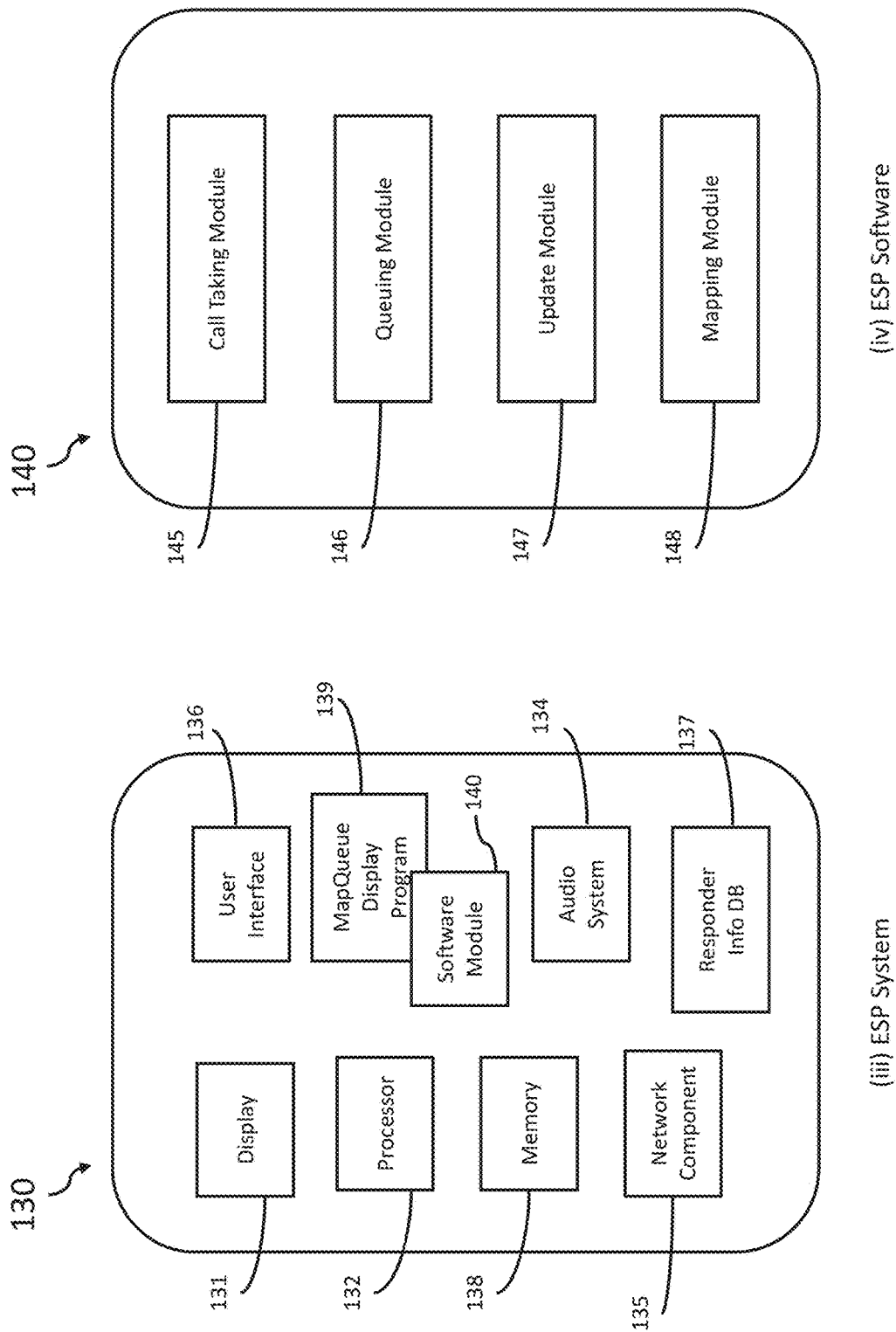
FIG. 1B depicts diagrams of a public safety answering point (PSAP) system and PSAP software.

In some embodiments, as depicted in FIG. 1B, an ESP system 130 includes one or more of a display 131 (e.g., a primary screen and supplemental screens), a user interface 136, at least one central processing unit or processor 132, a network component 135, an audio system 134 (e.g., microphone, speaker and/or a call-taking headset), and a computer program such as a ESP application or ESP program 139. In some embodiments, the ESP application or program 139 (e.g., a MapQueue application) comprises one or more software modules 140. In some embodiments, the ESP system 130 comprises a database of emergency responders (not shown), such as medical assets, police assets, fire response assets, rescue assets, safety assets, etc.

It is contemplated that responder devices may include a version of MapQueue application for displaying an interactive map of incidents. In some embodiments, responder devices are designed to display incidents within authoritative, administrative or assigned jurisdiction of the specific responder. The credentials of the responders may be matched to one or more geofence and incidents with current location within the geofences are displayed.

In some embodiments, responder devices display incidents based on a proximity radius on the interactive map.

For example, a proximity radius may be within 10 meters to 5 kms, between 50 meters to 1000 meters, preferably 500 meters. As the responder moves towards an area, new incidents within the proximity radius may be "unlocked" and viewed.

In some embodiments, as depicted in FIG. 1B, the ESP application or program 139 installed on a ESP system 130 comprising a software module 140 is a call taking module 145 (for receiving and disconnecting with callers), a queueing module 146 (for queuing emergency alerts in the jurisdiction), an update module 147 (once subscribed, the ESP may get updated emergency data such as location), a mapping module 148 (for displaying an interactive map) or a combination thereof. In some embodiments, the ESP application 139 displays the information on a map (e.g., on the display 131). In some embodiments, the mapping module 148 is configured to provide feedback from the ESP 130 to the EMS, as described below. It is contemplated that responder devices have optionally installed a responder device program (not shown) similar to the mapping module 148. In some embodiments, the responder device program displays the emergency location (e.g., current location) on a map.

Emergency Clearinghouse

In some embodiments, as described above, the emergency management system (EMS) 120 includes a clearinghouse 150 (also referred to as an "Emergency Clearinghouse") for storing and retrieving emergency data. In some embodiments, the clearinghouse 150 includes a location clearinghouse 150A and an additional data clearinghouse 150B. In some embodiments, the location clearinghouse 150A includes a location ingestion module and a location retrieval module, as described below with respect to FIG. 2. In some embodiments, the additional data clearinghouse 150B includes an additional data ingestion module and an additional data retrieval module, as described below with respect to FIG. 2. In other embodiments, additional data and location data (hereinafter, "emergency data") are stored in one or more databases in a distributed manner. In some embodiments, the emergency data is stored in an external or third-party server that is accessible to the EMS 120. The clearinghouse 150 optionally functions as an interface that receives and stores emergency data from electronic or communication devices that are then retrieved, transmitted, and/or distributed to recipients (e.g., emergency personnel) before, during, or after emergencies. As described above, the clearinghouse optionally receives emergency data from electronic or communication devices such as mobile phones, wearable devices, laptop or desktop computers, personal assistants, intelligent vehicle systems, home security systems, IoT devices, camera feeds, and other sources. As described above and below, emergency data optionally includes locations or additional data such as medical history, personal information, or contact information. In some embodiments, during an emergency, the clearinghouse 150 detects the emergency and/or otherwise identifies the need to provide emergency data pertaining to the emergency. The clearinghouse 150 then identifies any emergency data pertaining to the emergency stored within the clearinghouse 150 and transmits the pertinent emergency data to the requesting ESP. Accordingly, in some embodiments, the clearinghouse 150 acts as a data pipeline that automatically pushes emergency data to the ESP that would otherwise be without access to emergency data that is critical to most effectively and efficiently responding to an emergency. Accordingly, location data stored within the clearinghouse 150 allows emergency responders to arrive at the scene of an emergency faster, and additional data stored within the clearinghouse 150 allows emergency responders to be better prepared for the emergencies they face.

For example, in one embodiment, an emergency alert is triggered by an electronic device 110 (e.g., by pressing a soft button, a physical button, voice command, or gesture) or autonomously based on sensor data (e.g., smoke alarms). In this example, the user then confirms the emergency and/or provides authorization for sending the emergency alert. Emergency data, such as an enhanced location and additional data regarding the user (e.g., the user's medical history) is delivered by the electronic device 110 to the EMS 120 and stored in the clearinghouse 150 (e.g., in the location clearinghouse 150A and the additional data clearinghouse 150B). In some embodiments, the EMS 120 or clearinghouse 150 formats the emergency data into a format that is compatible with industry standards for storing and sharing emergency data. For example, the emergency data is formatted to be compatible with National Emergency Number Association (NENA) standards. In some embodiments, the EMS 120 or clearinghouse 150 transmits the emergency data to a receiving party in response to receiving a query (e.g., an emergency data request) from the receiving party, as described below. In some embodiments, the EMS 120 or clearinghouse 150 automatically pushes the emergency data to a receiving party such as the PSAP. For example, in some embodiments, the emergency management system automatically pushes the emergency data to a receiving party using a subscription system, as described below.

In some embodiments, as mentioned above, a requesting party (such as a PSAP responding to an emergency alert or a second emergency management system, as described below) queries the clearinghouse 150 with an emergency data request (such as a HTTP GET request). In some embodiments, the emergency data request is in the form of the Location Information Server (LIS) protocol. In response to receiving the emergency data request, the EMS 120 or clearinghouse 150 sends an appropriate response including relevant emergency data to the requesting party via an encrypted pathway. In some embodiments, the emergency data request is in the form of HTTP-Enabled Location Delivery (HELD) and the response from the EMS 120 or clearinghouse 150 is in the form of Presence Information Data Format Location Object (PIDF-LO). In some embodiments, the emergency data request includes an authorization code (e.g., an "authorization token" or "temporary access token") in the body, header, or metadata of the request, and the EMS 120 checks that the authorization code is active before providing a response to the requesting party. In some embodiments, authorization is provided in the "Authorization" header of the emergency data request using HTTP Basic Authentication. For example, in some embodiments, authorization is base64-encoded username and password for an account associated with the requesting party. In some embodiments, emergency data requests are sent over public networks using API access keys or credentials. In some embodiments, Transport Layer Security (TLS) is used in the requests and responses from the EMS 120 for encryption security. In some embodiments, the call taking module 145 includes a call-handling application, which is provided by a third-party vendor. In some embodiments, an ESP personnel interacts with the call-handling application to send an emergency data request to the EMS 120. In some embodiments, the response from the EMS 120 is displayed at the ESP display 131.

In some embodiments, as described above, emergency data includes locations and additional data. In some embodiments, emergency data includes one or more emergency data categories (also referred to as "data categories"). In some embodiments, the emergency data categories include: service data reference, full name, email, emergency contacts, addresses, language, occupation, phone numbers, websites, gender, height, weight, ethnicity, profile picture, allergies, medical conditions, medications, disabilities, blood type, medical notes, birthday, and additional comments. In some embodiments, emergency data categories are tagged with tags for specific types of data such as "demographics" or "medical data." For example, in some embodiments, gender, height, weight, ethnicity, profile picture (image-url) are tagged as demographic data. In some embodiments, medical data protected under HIPAA and other laws are tagged as "HIPAA" or "private." In some embodiments, medical data includes information on one or more of allergies, medical condition(s) or illness(es), medication(s), disabilities, blood type, medical note(s), and other medical information. In some embodiments, medical information protected under HIPAA are encrypted and/or anonymized. In some embodiments, some data are tagged as "general" or another similar tag, wherein access is not specifically restricted.

An example of an additional data communication from the EMS 120 in a standard format compatible with industry standards, PIDF-LO, is shown below.

HTTP/1.1 200 OK
Date: Tue, 1 Dec. 2016 23:27:30 GMT
Content-Length: 489
Content-Type: application/EmergencyCallData.DeviceInfo+xml
<dev:EmergencyCallData.DeviceInfo
xmlns:dev="urn:ietf:params:xml:ns:EmergencyCallData:DeviceInfo">
<dev:DataProviderReference>d4b3072df.201409182208075@example.org In some embodiments, when the emergency data is stored at a third-party server and receives a request for emergency data from the EMS 120, as a database query, the third-party server formats the requested emergency data and stores this information in an alternate database, and forwards either a response or a reference to the alternate database for accessing the emergency data requested by the EMS 120, which is provided to the ESP 130 over a hybrid analog and/or a data communication channel, depending on the capabilities of ESP 130. In some embodiments, the third-party server stores the emergency data, requested by the EMS 120 or directly by the ESP 130, in the alternate database for a certain period of time after receiving the request for the emergency data regarding a user and any electronic devices 110. In some embodiments, this period of time is a timer value (e.g., a timer countdown or a set time point) defined by the EMS 120 and the third-party server in conjunction with each other prior to the addition of the requested emergency data to the alternate database at the third-party server. In some embodiments, once the timer value has passed and no new requests for the emergency data pertaining to the particular user and the electronic device 110, or other devices associated with the user, are received by the third-party server, then the third-party server marks the particular alternate database entries to be deleted and waits for another, different, time-out interval. In some embodiments, once this particular second time-out interval has also been completed and no new requests for location data for the particular user or associated electronic devices 110 are received by the third-party server, the third-party server removes the specific marked entries from the alternate database in the next cycle of updates for the alternate database. In some embodiments, after adding the emergency data in the alternate database by the third-party server, the third-party server keeps updating the emergency data in the alternate database on a periodic, or as-needed basis, for the purpose of keeping the emergency data about the user or electronic device 110 current for providing the most recent and accurate emergency data to the EMS 120 and the ESP 130 for the purposes of responding to a request for emergency assistance. In some embodiments, the third-party server is updated by the EMS 120 for all the emergency data pertaining to all users and their associated electronic devices 110 that are served by the EMS 120 at any current time.

In some non-emergency situations, there is a need to access location data, user data, emergency data or sensor data. For example, in some embodiments, a user of an electronic device 110 grants authorization to family members to access location data for the user. Accordingly, when a family member requests location data for a user, access is granted if there is proper authorization. As another example, in some embodiments, a taxi operations company requests and obtains location data of one or more fleet members to keep track of its vehicles (e.g., via onboard vehicle console or terminal).

Various embodiments and applications of the clearinghouse 150 are described in detail herein. However, the embodiments and applications described herein should not be considered exhaustive or limiting in any way.

Figure 2:
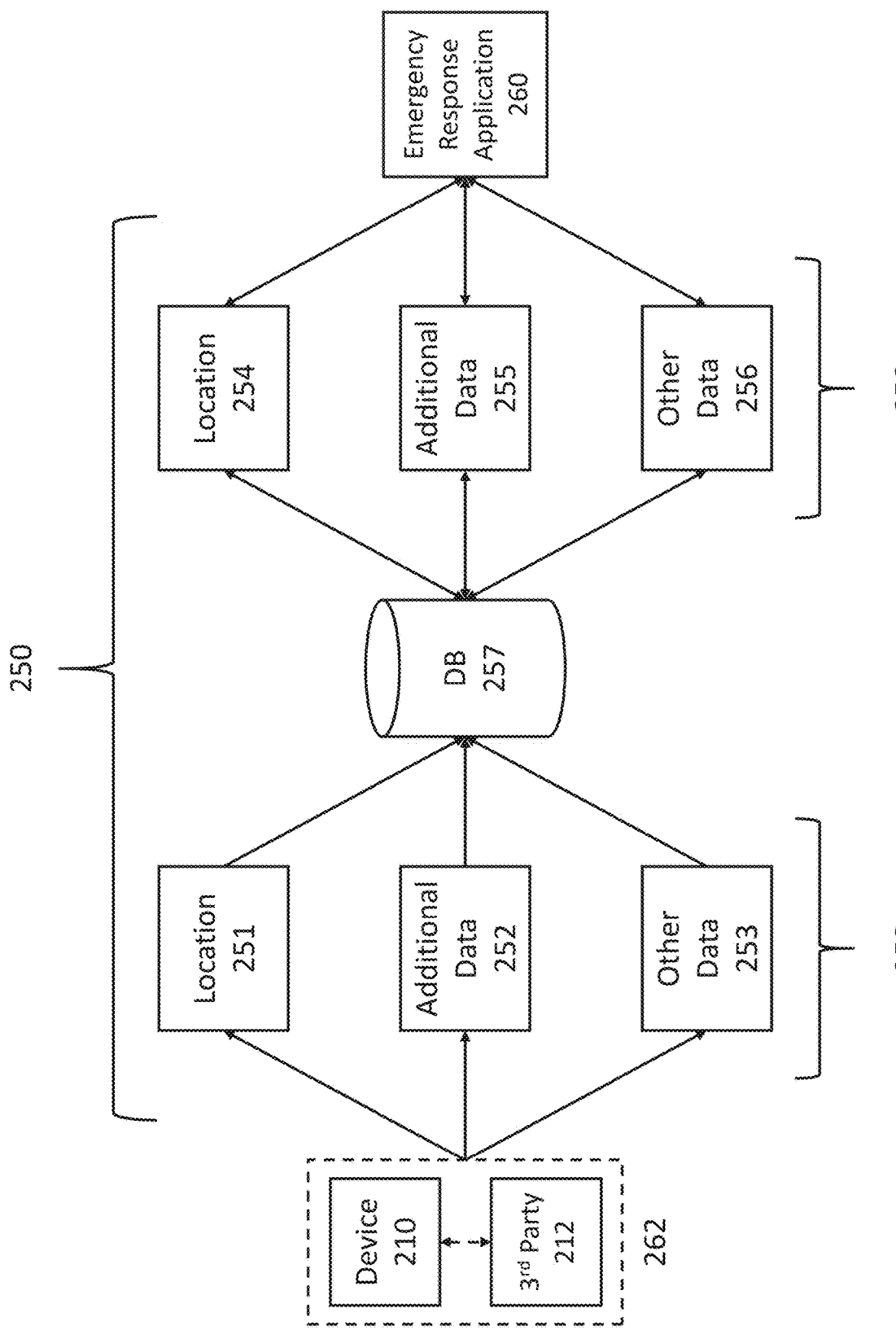
FIG. 2 depicts a diagram of a clearinghouse for emergency data.

FIG. 2 depicts an embodiment of an Emergency Clearinghouse 250 for storing and retrieving emergency data. In some embodiments, the clearinghouse 250 includes a set of ingestion modules 258 (also referred to as "ingestion modules") and a set of retrieval modules 259 (also referred to as "retrieval modules"). The set of ingestion modules 258 is configured to receive various forms of emergency data from various emergency data sources 262, such as an electronic device 210 or a third-party server system 212 (hereinafter, "third-party server"). In some embodiments, an electronic device 210 is a communication device (e.g., a mobile phone), a wearable device (e.g., a smartwatch), or an internet of things (IoT) device (e.g., a smart speaker) that can communicate with one or more of the ingestion modules within the set of ingestion modules 258. In some embodiments, a third-party server 212 receives and stores data generated by or stored within an electronic device 210. For example, in some embodiments, when an emergency alert is generated by an electronic device 210, the electronic device 210 transmits emergency data (e.g., an enhanced location or additional data) to a third-party server 212 to which the electronic device 210 is communicatively coupled to. The third-party server 212 can then transmit the emergency data received from the electronic device 210 to an emergency management system 120, such as through the clearinghouse 250. In some embodiments, a third-party server 212 stores data that is not generated by or stored within an electronic device. For example, in some embodiments, a third-party server 212 includes a database of static medical information that can be sent to the clearinghouse during an emergency. In some embodiments, when the emergency management system 120 detects an emergency (e.g., when a person calls 9-1-1), the clearinghouse can query an emergency data source 262 for emergency data regarding the emergency. For example, in some embodiments, in response to detecting a 9-1-1 call made from a mobile phone, the additional data ingestion module 252 (as described below) sends a query including the phone number of the mobile phone to a third-party server 212 that stores static medical information. The third-party server 212 can then return any available medical information associated with the phone number of the mobile phone to the additional data ingestion module. In some embodiments, multiple ingestion modules within the set of ingestion modules can receive emergency data for a single emergency. For example, in some embodiments, when a person calls 9-1-1 from a mobile phone, the mobile phone can send a device-based hybrid location to the location ingestion module 251 (as described below) and demographic data (as described above) to the additional data ingestion module 252. In some embodiments, the clearinghouse can receive emergency data from multiple emergency data sources 262 for a single emergency. For example, in some embodiments, when a person calls 9-1-1 from a mobile phone, the clearinghouse can receive a location from the mobile phone (such as through the location ingestion module 251) and a heartrate from a smartwatch that the person is wearing (such as through additional data ingestion module 252). Or for example, in some embodiments, when a person calls 9-1-1 from a mobile phone, the clearinghouse can receive a location from the mobile phone and medical information associated with the person from a third-party server 212.

The set of ingestion modules 258 optionally include a location ingestion module 251, an additional data ingestion module 252, and one or more other data ingestion modules 253. In some embodiments, the location ingestion module 251 is an emergency location service ingestion interface for posting or receiving emergency locations. In some embodiments, the location ingestion module 251 is a REST API that receives an HTTP POST including location data when an emergency alert is generated (e.g., when an emergency call is made from a cell phone). The location data includes a location generated concurrently or in response to the generation of the emergency alert. In some embodiments, the location data includes a location generated before the emergency alert. For example, when an emergency call is made from a cell phone, thereby generating an emergency alert, the location ingestion module 251 receives a location recently generated by the phone but before the emergency alert was generated, ensuring that a location for the emergency is available as quickly as possible. In some embodiments, the location data includes a device-based hybrid location generated by an electronic device 210 that generated the emergency alert. In some embodiments, the location data includes a location generated by a second electronic device communicatively coupled to the electronic device that generated the emergency alert. The location ingestion module 251 is integrated into an electronic device 210 through a mobile application installed on the device 210 or integrated into the firmware or operating system of the electronic device 210.

In some embodiments, the location data is generated by the electronic device 210 before the emergency and is accessible to a PSAP during an emergency. For example, a taxi company may have software that transmits the location of its cars or assets to the emergency clearinghouse 250 preemptively. Thus, when an emergency arises, the location of the affected taxi can be made accessible quicker to send help. In some embodiments, the location data is generated by the electronic device 210 after the emergency has commenced and is made accessible to a PSAP during the on-going emergency. For example, updated location data of a hijacked taxi is also periodically transmitted to the emergency clearinghouse 250 and made accessible to a PSAP.

In some embodiments, the additional data ingestion module 252 is an interface for posting or receiving static or dynamic emergency profile data (hereinafter, "additional data" or "additional information"). In some embodiments, additional data comprises medical data, personal data, demographic data, health data, or any combination thereof. Examples of medical data include information relating to a person's medical history, such as past surgeries or preexisting conditions. Examples of personal data include a person's name, date of birth, height, weight, occupation, address(es) (e.g., home address, work address, etc.), spoken languages, and other personal information. Examples of demographic data include a person's gender, ethnicity, age, etc. Examples of health data include information such as a person's blood type or heartrate. In some embodiments, additional data comprises data received from connected devices such as vehicles, IoT devices, and wearable devices. For example, some intelligent vehicle systems generate and send data regarding a crash, such as the speed at which the vehicle was moving just before the collision, where the vehicle was struck, the number of occupants, etc. In some embodiments, the additional data ingestion module 252 is a REST API (e.g., a JSON (JavaScript Object Notation) REST API). For example, in some embodiments, when an emergency call is made from a cell phone, thereby generating an emergency alert, the cell phone receives a heartrate of the person who made the emergency call from a smartwatch worn by the person and communicatively coupled to the cell phone (e.g., Wi-Fi or Bluetooth connectivity). The cell phone sends the heartrate to the additional data ingestion module 252, along with any other additional data, in an HTTP POST. In some embodiments, the additional data ingestion module 252 is integrated into an electronic device 210 through a mobile application installed on the device 210 or integrated into the firmware or operating system of the electronic device 210. In some embodiments, additional data is sent to the additional data ingestion module 252 from a network server. The additional data ingestion module 252 is accessed by any connected platform that receives data that might be relevant in an emergency. Connected platforms optionally send additional data to the additional data ingestion module 252 at any time. For example, in some embodiments, a website, web application, or mobile application integrated with the additional data ingestion module 252 that allows users to create profiles sends additional data included in the profiles to the additional data ingestion module 252 every time a profile is created or updated.

In some embodiments, the set of ingestion modules 258 includes one or more other data ingestion modules 253. Another data ingestion module 253 is optionally an interface for posting or receiving data relevant to emergencies that is not received by the location ingestion module 251 or the additional data ingestion module 252. In some embodiments, the other data ingestion module 253 receives audio or video streams during an emergency from electronic or communication devices associated with the emergency or proximal to the emergency. For example, an emergency alert is generated by an intelligent vehicle system installed in a vehicle in response to the vehicle experiencing a collision. In this example, the emergency alert is sent to the EMS 120 by the intelligent vehicle system or by an electronic device communicatively coupled to the intelligent vehicle system, such as a cell phone coupled to the intelligent vehicle system via Bluetooth. In response to generating the emergency alert, the intelligent vehicle system additionally begins streaming audio and video from microphones and cameras installed inside or outside of the vehicle to the clearinghouse 250 through the other data ingestion module 253. A cell phone communicatively coupled to the intelligent vehicle system additionally or alternatively streams audio or video from microphones and cameras integrated into the cell phone to the clearinghouse 250 through the other data ingestion module 253. In some embodiments, the one or more other data ingestion modules 253 are REST APIs that are accessed with an HTTP POST.

After receiving the relevant data, the set of ingestion modules 258 can store the data in one or more clearinghouse databases 257. For example, in some embodiments, the clearinghouse databases 257 include a location database and an additional data database. In some embodiments, as described above, the one or more clearinghouse databases 257 are stored on a third-party server communicatively coupled to or otherwise accessible by the EMS 120. In some embodiments, the set of ingestion modules 258 tags or otherwise associates the data received by the modules with an identifier of a user or device associated with the data. For example, the set of ingestions modules 258 tag the data the received by the modules with a user ID number, an email address, or a phone number (e.g., caller ID). In some embodiments, the ingestion modules 258 tag the data received by the clearinghouse 250 based on the data source (e.g., device name or type, application name, username, phone number, corporate account, etc.).

In some embodiments, the emergency data maintained by the clearinghouse is purged. In some embodiments, the data is purged on a regular or periodic basis. In some embodiments, data that is older than a defined threshold is purged. In some embodiments, different data types are purged according to different schedules and/or thresholds. For example, dynamic data (e.g., data that is subject to constant or regular change) such as location data may be more likely to become out-of-date over time and so may be purged more frequently than static data such as a permanent home address, which may remain permanently in the database until it is replaced with an updated address.

In some embodiments, an individual or group of individuals are associated with multiple identifiers. For example, the location ingestion module 251 receives a location generated by a phone associated with the phone number+1-555-555-5555, associated with John Doe. The additional data ingestion module 252 also receives a heartrate from a smartwatch associated with the email address johndoe@email.com, also associated with John Doe. In this example, the set of ingestion modules 258 tag the location with the phone number "+1-555-555-5555," tag the heartrate with the email address "johndoe@email.com," and associate both the location and the heartrate with John Doe in the clearinghouse databases 257.

In some embodiments, as depicted in FIG. 2, the clearinghouse 250 includes a set of retrieval modules 259. The set of retrieval modules 259 optionally include a location retrieval module 254, an additional data retrieval module 255, and one or more other data retrieval modules 256. In some embodiments, the location retrieval module 254 is an interface for retrieving location data from the clearinghouse databases 257. In some embodiments, the location retrieval module 254 is a JSON REST API that receives a query or request (e.g., in the form of an HTTP GET request) from a requesting party, such as an ESP. In some embodiments, the request is sent from a call-taking application (e.g., call taking module 145) integrated into the ESP system 130. In some embodiments, the request (also referred to as an "emergency data request") is sent from an emergency response application 260. In some embodiments, the location retrieval module 254 provides a single GET endpoint for retrieving either the latest or paginated list of locations for a specific caller ID (e.g., an identifier of a user or an electronic device associated with a user, such as a phone number). For example, as described above, a phone number associated with a device 210 from which a location was received is included in the header, body, or metadata of the request sent to the location retrieval module 254. The clearinghouse 250 then retrieves a location or set of locations from the clearinghouse databases 257 and delivers the location or set of locations to the requesting party. In some embodiments, the location retrieval module 254 is a location information server (LIS). In some embodiments, the LIS is a NG911 standards-based XML API for the retrieval of location data from the clearinghouse databases 257. In some embodiments, as described above, the location retrieval module 254 accepts HELD requests from requesting parties and returns location data for a specific caller ID or anonymous reference. However, in some embodiments, the location retrieval module 254 automatically retrieves and transmits location data using a subscription system, as described below.

As depicted in FIG. 2, the set of retrieval modules 259 optionally include an additional data retrieval module 255. In some embodiments, the additional data retrieval module 255 is a JSON REST API for the retrieval of emergency or additional data. As described above, additional data optionally includes medical data, personal data, demographic data, and health data. Additional data also optionally includes data received from connected devices such as vehicles, IoT devices, and wearable devices. In some embodiments, the additional data retrieval module 255 receives a query or request (e.g., in the form of an HTTP GET request) from a requesting party, such as an ESP or a second emergency management system, as described below. In some embodiments, the request (also referred to as an "emergency data request") is sent from an emergency response application 260. The additional data then retrieves additional data associated with a specific or particular identifier of a user or an electronic device associated with the user, such as a phone number, and returns the data to the requesting party. In some embodiments, the set of retrieval modules 259 further includes one or more other data retrieval modules 256, which function similarly to the location retrieval module 254 and additional data retrieval module 255, for the retrieval of data stored in the clearinghouse databases 257 not retrieved by the location retrieval module 254 or additional data retrieval module 255. However, in some embodiments, the additional data retrieval module 255 automatically retrieves and transmits additional data using a subscription system, as described below.

In some embodiments, a retrieval module within the set of retrieval modules 259 and a corresponding ingestion module within the set of ingestion modules 258 form a sub-clearinghouse. For example, in some embodiments, location ingestion module 251 and location retrieval module 254 combine to form location clearinghouse 150A (as shown in FIG. 1B). Likewise, in some embodiments, additional data ingestion module 252 and additional data retrieval module 255 combine to form additional data clearinghouse 150B. In some embodiments, a requesting party is only given access to a particular sub-clearinghouse. For example, a police officer is only given access to the location clearinghouse 150A, while an EMT (emergency medical technician) is only given access to the additional data clearinghouse 150B. However, a requesting party is given differential access to the clearinghouse 150, sub-clearinghouses, or particular emergency data categories within the clearinghouse 150 based on any factor or set of factors. In some embodiments, a requesting party initiates a query or request (i.e., an emergency data request) using an emergency response application 260 (as described below), which in turn generates the query and transmits the query to the clearinghouse 250.

In some embodiments, the clearinghouse 250 includes an emergency data streaming module or streaming module (not shown). In some embodiments, a streaming module is capable of both receiving and transmitting emergency data, but emergency data received by the streaming module is not stored within a database. Instead, emergency data is streamed through the streaming module without being committed to memory within the clearinghouse 250. In some embodiments, the streaming module establishes an active or persistent communication link (e.g., a websocket connection, as described below) between the EMS or clearinghouse 250 and an emergency data recipient. For example, in some embodiments in which emergency data is pushed from the EMS or clearinghouse 250 to an emergency data recipient, the streaming module can establish a persistent communication link between the EMS or clearinghouse 250 and the emergency data recipient, and any emergency data that is received by the EMS or clearinghouse 250 to which the emergency data recipient is subscribed (as described below) is pushed to the emergency data recipient through the persistent communication link without being committed to memory within the EMS or clearinghouse 250.

Emergency Data Subscription System

As described above, in some embodiments, an emergency management system (EMS) maintains a clearinghouse 250 that obtains and shares emergency data to aid emergency service providers (ESPs) in responding to emergencies. During an emergency, in some embodiments, an ESP can send an emergency data request to the EMS through the emergency response application 260, and, in response, the EMS can send any available emergency data associated with the emergency back to the emergency response application 260. In some embodiments, as described above, the emergency response application 260 includes an identifier associated with an emergency alert in the emergency data request. The EMS can then use the identifier associated with the emergency alert to retrieve emergency data associated with the emergency alert from the clearinghouse. For example, as described above, an ESP 230 (e.g., a public safety answering point (PSAP)) can receive an emergency alert in the form of a 9-1-1 phone call (representative of an emergency or potential emergency) from a mobile phone associated with a phone number (e.g., (555) 555-5555). The ESP 230 can then send an emergency data request including the phone number (i.e., the identifier of the emergency alert) to the EMS, which can then retrieve any emergency data within or accessible by the clearinghouse associated with the phone number and return the available emergency data to the requesting ESP 230. This process of returning emergency data to the emergency response application 260 in response to an emergency data request is referred to as "pulling" emergency data from the clearinghouse.

However, in some embodiments, the EMS can "push" emergency data from the clearinghouse 250 to the emergency response application (i.e., the EMS can send emergency data to the emergency response application 260 without receiving an emergency data request). In some embodiments, the EMS pushes emergency data to the emergency response application 260 using an emergency data subscription system. Using the emergency data subscription system, a recipient (or potential recipient) of emergency data from the clearinghouse 250 can subscribe to the clearinghouse 250 for a particular device identifier, user identifier, or ESP identifier (hereinafter, "subscription"). After subscribing to a subscription, the recipient (e.g., an ESP or second EMS) may automatically receive updates regarding the subscription without first sending an emergency data request. For example, in some embodiments, if an ESP subscribes to a phone number, whenever the clearinghouse 250 receives updated emergency data associated with the phone number, the clearinghouse 250 can automatically send the updated emergency data associated with the phone number to the ESP (e.g., through the emergency response application 260), without first receiving an emergency data request including the phone number. For example, in some embodiments, if a recipient is subscribed to a particular phone number, and the clearinghouse 250 receives a new or updated location associated with the particular phone number, the clearinghouse 250 will instantly and automatically push the new or updated location associated with the particular phone number to the recipient the moment that the new or updated location is received by the clearinghouse 250, without the recipient having to send an emergency data request. In some embodiments, when an ESP or ESP personnel accesses the emergency response application 260 at a computing device associated with the ESP or ESP personnel, the EMS establishes a persistent or active communication link (e.g., a websocket connection) with the computing device in order to push emergency data regarding a subscription to which the ESP or ESP personnel is subscribed to the emergency response application 260.

In some embodiments, an active communication link is a connection, or a potential connection (e.g., two corresponding endpoints), between two entities (e.g., an EMS and an ESP) through which data can be freely transmitted (i.e., without a recipient entity having to actively accept transmitted data). In some embodiments, an active communication link is a persistent communication link. In some embodiments, a persistent communication link is a communication link that endures for a period of time that is not dependent on the transmission of a particular packet of data. For example, in some embodiments, a persistent communication link between two entities (e.g., an EMS and an ESP) endures until the communication link is actively terminated by one of the entities, as opposed to passively terminating once a particular packet of data (e.g., a particular emergency alert) has been transmitted. In another example, a persistent communication link endures for a predetermined amount of time (e.g., five minutes or an hour). In another example, a persistent communication link established between an EMS and an ESP through an emergency response application endures until a login session on the emergency response application is terminated or the emergency response application itself is terminated. In some embodiments, a persistent communication link is a websocket connection. Web-Socket is a type of computer communications protocol. A websocket connection is a longstanding or persistent internet connection between a client and a server that allows for bidirectional communication between the client and server without the client needing to send data requests to the server, which differentiates the WebSocket computer communications protocol from other types of computer communications protocols such as the HyperTextual Transfer Protocol (HTTP). The WebSocket protocol is often used by chat clients to facilitate user to user webchats. In some embodiments, the EMS establishes a n active communication link with a computing device (e.g., an ESP console 130) in response to receiving an emergency data request. In some embodiments, the EMS establishes an active communication link with an ESP console when an ESP personnel logs into the emergency response application 260 at the ESP console.

In some embodiments, the EMS establishes an active communication link with a responder device when an ESP personnel logs into the emergency response application 260 at the responder device. In some embodiments an active communication link established between the EMS and a computing device associated with ESP personnel is maintained by the EMS for the duration of the ESP personnel's log-in session.

In some embodiments, the EMS automatically subscribes a recipient to a subscription (e.g., a particular device identifier or user identifier) in response to receiving an emergency data request including the subscription or an identifier of the subscription. For example, in some embodiments, when an ESP personnel sends an emergency data request including a phone number to the EMS through their ESP console (e.g., through the emergency response application 260), the EMS subscribes the ESP personnel to the phone number and establishes a persistent or active communication link with the ESP console. Then, whenever the clearinghouse 250 receives updated emergency data associated with the phone number, the EMS can automatically push the updated emergency data associated with the phone number to the ESP console. For example, an ESP personnel logs into an emergency response application 260 in communication with the EMS on the ESP personnel's ESP console. Subsequently, the ESP personnel receives a 9-1-1 call from a mobile phone and then generates and sends an emergency data request including the phone number of the mobile phone to the EMS through the emergency response application 260. The EMS then uses the phone number of the mobile phone to retrieve the most recent location associated with the mobile phone received by the clearinghouse and returns the most recent location associated with the mobile phone to the ESP personnel through the emergency response application 260. The EMS simultaneously subscribes the ESP personnel to the phone number of the mobile phone and establishes a websocket connection between the EMS and the ESP console and automatically pushes any updated emergency data (e.g., enhanced locations) associated with the phone number received by the clearinghouse to the emergency response application 260 as soon as the updated emergency data associated with the phone number is received by the clearinghouse 250.

In some embodiments, an ESP is associated with an identifier of the ESP (e.g., a unique ESP account ID; also referred to as an "ESP identifier") that an ESP or ESP personnel can subscribe to. The EMS can then establish a persistent or active communication link with a computing device associated with an ESP or ESP personnel subscribed to the unique ESP identifier and push emergency data associated with the unique ESP identifier to the computing device (e.g., through the emergency response application 260) whenever new or updated emergency data associated or tagged with the unique ESP identifier is received by the clearinghouse 250. For example, in some embodiments, when the clearinghouse 250 receives a location (e.g., an emergency location) associated with an emergency alert (e.g., when a person calls 9-1-1 from a mobile phone and the mobile phone responsively sends a current location of the mobile phone to the clearinghouse 250), the EMS retrieves one or more geofences (as described below) associated with each ESP registered with the EMS and determines which (if any) of the geofences that the emergency location associated with the emergency alert falls within. The EMS then tags the location associated with the emergency alert with the unique ESP identifiers associated with each of the ESPs associated with geofences that the location associated with the emergency alert falls within. For example, if four ESPs are registered with the EMS—ESP A, ESP B, ESP C, and ESP D—and the clearinghouse 250 receives a location associated with an emergency that falls within the one or more of the geofences associated with ESP A and ESP D, the EMS can tag the location associated with the emergency alert with the unique ESP account ID associated with ESP A and the unique ESP account ID associated with ESP D. The EMS can then push the location associated with the emergency alert to any ESPs or ESP personnel with an established persistent or active communication link with the EMS and currently subscribed to either the unique ESP account ID for ESP A or the unique ESP account ID for ESP D. In some embodiments, when an ESP personnel logs into the emergency response application 260, a communication is sent to the EMS that includes one or more unique ESP account IDs that the ESP personnel or their respective ESP is currently subscribed to.

Emergency Data Geofencing

Figure 3:
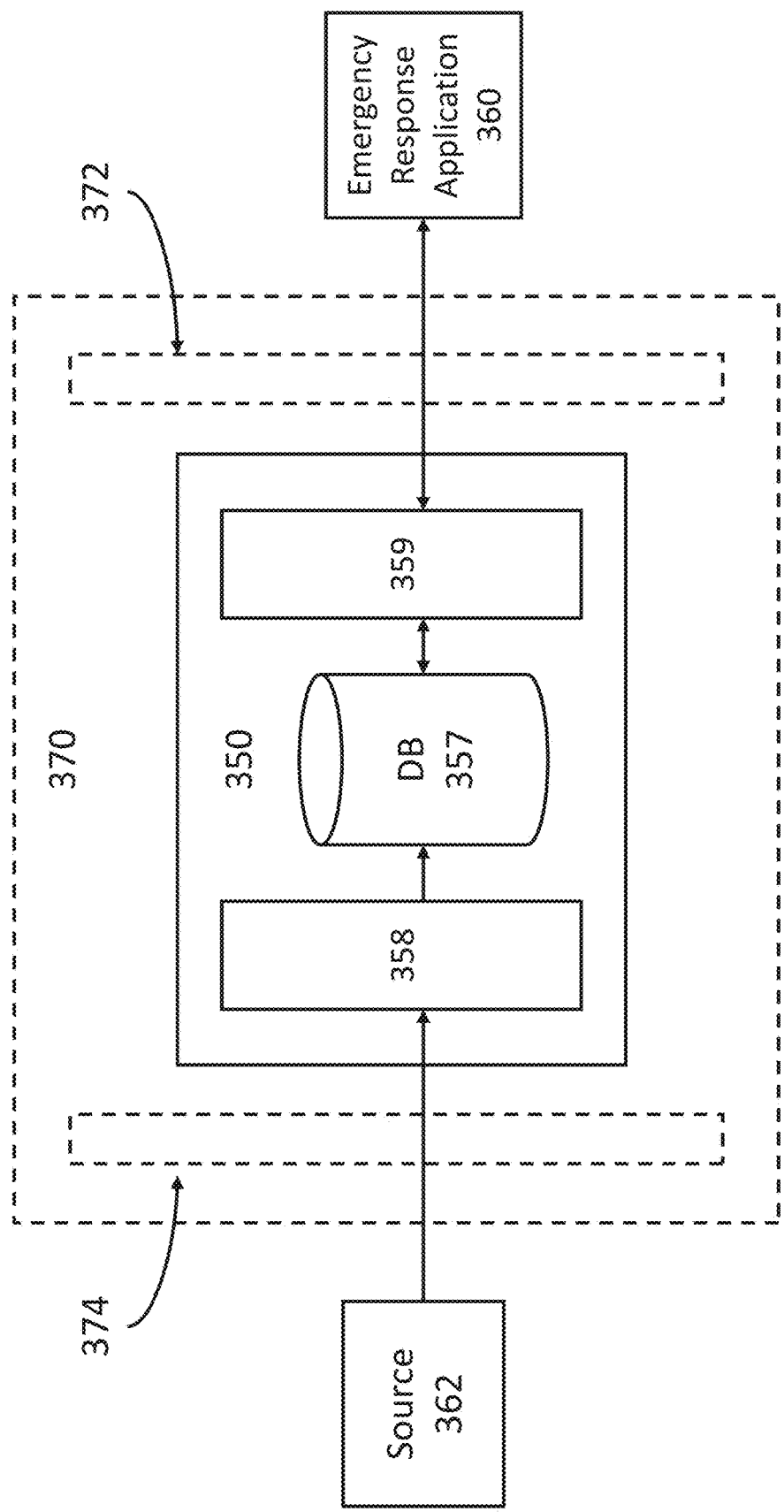
FIG. 3 depicts a diagram of a geofence applied to a clearinghouse for emergency data.

FIG. 3 depicts a diagram of a geofence applied to a clearinghouse for emergency data. In some embodiments, a geofence module 370 is applied to the clearinghouse 350 to protect potentially sensitive emergency data using geospatial analysis. In some embodiments, as described above with respect to FIG. 2, the clearinghouse 350 includes a set of ingestion modules 358 and a set of retrieval modules 359. The set of ingestion modules can receive emergency data, or other information that can be useful in responding to an emergency, from a variety of sources. For example, in some embodiments, a smartphone sends emergency data to the clearinghouse 350 in the form of an HTTP POST API call in response to a user of the smartphone initiating a 911 emergency call. As depicted in FIG. 3, in some embodiments, when emergency data (e.g., an emergency location or additional emergency data) is sent (directly or indirectly, such as through a third-party server) from an electronic device 310 to the clearinghouse 350, the emergency data is first processed by a geofence module 370 before being received by the set of ingestion modules 358 within the clearinghouse 350, as described below with respect to FIG. 10. Similarly, in some embodiments, when an emergency data request is sent from a requesting party (e.g., the emergency response application 360, as described below), the emergency data request is processed by the geofence module 370 before being received by the set of retrieval modules 359 for display on a GUI of the emergency response application 360 on a computing device of the requesting party.

In some embodiments, as mentioned above, a geofence module 370 is applied to the clearinghouse 350 to protect potentially sensitive emergency data using geofences. Generally, a geofence is a virtual perimeter for a real-world geographic area. A geofence can be dynamically generated—as in a radius around a point location—or a geofence can be a predefined set of boundaries (such as school zones or neighborhood boundaries). The use of a geofence is called geofencing, and one example of usage involves a location-aware device of a location-based service (LBS) user entering or exiting a geofence. Entry or exit from a geofence could trigger an alert to the device's user as well as messaging to the geofence operator. The geofence information, which could contain the location of the device, could be sent to a mobile telephone or an email account.

For emergency response, an emergency service provider (public or private entities) may be given jurisdictional authority to a certain geographical region or jurisdiction (also referred to as "authoritative regions"). In the context of emergency services, one or more geofences may correspond to the authoritative region of an ESP. In many cases, the ESP is a public entity such as a public safety answering point (PSAP) or a public safety service (PSS; e.g., a police department, a fire department, a federal disaster management agency, national highway police, etc.), which have jurisdiction over a designated area (sometimes, overlapping areas). Geofences are used to define the jurisdictional authority by various methods and in various Geographic Information System (GIS) formats. In some embodiments, geofences only represent authoritative regions if the geofence has been assigned or verified by a local, state, or federal government. In some embodiments, geofences represent assigned jurisdictions that are not necessarily authoritative regions. For example, in some embodiments, a geofence is unilaterally created by its associated ESP without verification or assignment by a local, state, or federal government.

Geofences can be defined in various ways. For example, in some embodiments, a geofence comprises one or more of the following: a county boundary, a state boundary, a collection of postal/zip codes, a collection of cell sectors, simple shapes, complex polygons, or other shapes or areas. In some embodiments, geofences comprise approximations where the "approximated" geofence encloses an approximation of the authoritative region.

Updates to geofences may be required over time because the authoritative regions may change over time. Geofences may change over time (e.g., a new sub-division has cropped up) and require updates. In some embodiments, the systems and methods described herein allow geofences to be updated (e.g., a PSAP administrator can upload updated geofence GIS shapefiles).

For maintaining the privacy, security and integrity of the data, geofencing may be applied to emergency data. For example, applying geofence filters to the emergency data allows additional avenues for monitoring, both visibility and control, over the clearinghouse to detect anomalies/spikes and reduce the risk of security breaches.

In some embodiments, the emergency data is obtained from an emergency data source 362 (such as an electronic device or third-party server, as described above). On the retrieval side, in some embodiments, an emergency data recipient 363 accesses the clearinghouse 350 by sending an emergency data request to the clearinghouse 350, as described above. An ingestion geofence 374 (also referred to as "upstream filtering") is applied to restrict sending of data from emergency data sources 362 to the clearinghouse 350 from geographical areas that are not covered by the "combined authoritative jurisdiction" (i.e., covered one or more provisioned geofences in the geofence database (not shown)). In some embodiments, the ingestion geofence (also referred to as an "ingress filter") is applied to the ingestion module 358 to protect against accidental breaches of privacy. In some embodiments, the ingestion module 358 of the clearinghouse 350 drops location payloads that do fall within the geographical region covered by the "combined authoritative region."

In some embodiments, the clearinghouse 350 comprises one or more databases 357 (e.g., a database storing emergency data). For example, in some embodiments, the retrieval module 359 obtains emergency data from a clearinghouse database 357 to send to an emergency data recipient 363 (e.g., an ESP) in response to an emergency data request, as described above. In some embodiments, the retrieval geofence 372 (also referred to as an "egress filter") is applied at the retrieval module 359 of the clearinghouse 350. Applying geofencing to retrieved emergency data will protect against abuse and limit the scope of security breaches in cases where credentials have been compromised. In some embodiments, one or more geofences are associated with one or more credentials associated with an ESP agency or organization. In some embodiments, the credentials associated with an ESP agency or organization confers authorization to access data such as emergency data from the clearinghouse. In some embodiments, specific authorization to access data is granted individually to members of a PSAP through tokens derived from the credentials for that PSAP.

In some embodiments, when the retrieval module 359 checks the coordinates of current location data (within retrieved emergency data) associated with a device identifier with the geofence(s) associated with the credentials in an emergency data request. If the current location is within the geofence region (enclosed by the geofence(s)), the current location is returned to the ESP and displayed within the ESP console. If not, the module 359 will return a "not found" message (as opposed to the retrieved location is outside the geofence) to protect privacy.

In some embodiments, geofences can be used for reporting results for internal metrics and monitoring the system. For example, the number of emergency data requests, locations provided, "no location found" etc., can be obtained for a geofence(s) associated with a PSAP. Using single or combined geofences, the emergency data can be obtained on county-wide, city-wide, postal code, course grid (rectangle overlay), state-wide, or country-wide basis. In some embodiments, ingress and egress counters (i.e., percent of emergency sessions where the location data was received, but not queried) and other similar metrics can be calculated and analyzed to identify problems and spikes. In some embodiments, different geofences are used for retrieval and for reporting.

In some embodiments, a given incident (e.g., an incident associated emergency alert, as described below) can be determined to fall within a plurality of geofences, as described below. In some embodiments, emergency data for the incident is pushed to each PSAP having a geofence that the incident (e.g., a location associated with the incident) falls within. In some embodiments, emergency data for the incident is pushed to a subset of PSAPs having a geofence that encloses or encompasses the incident. In some embodiments, the location data of an individual device identifier is not pushed to more than one PSAP at one time. In some embodiments, wherein a device identifier egresses a geofence in which communication began and ingresses into a neighboring geofence, the location data is autocratically pushed to the neighboring PSAP with jurisdiction over the ingress geofence.

To determine the appropriate ESP(s) for sharing emergency data, the authoritative jurisdiction (defined by one or more geofences) of an ESP (e.g., primary agency) has to be evaluated. In case of irregularities (e.g., overlaps, islands, or other irregular features), steps may be taken to check with respective agency, geographical boundaries (national and international borders, county lines, rivers, hills, etc.), or other authority. In some embodiments, call routing data may be analyzed to see which ESP is answering the emergency call.

Figure 7:
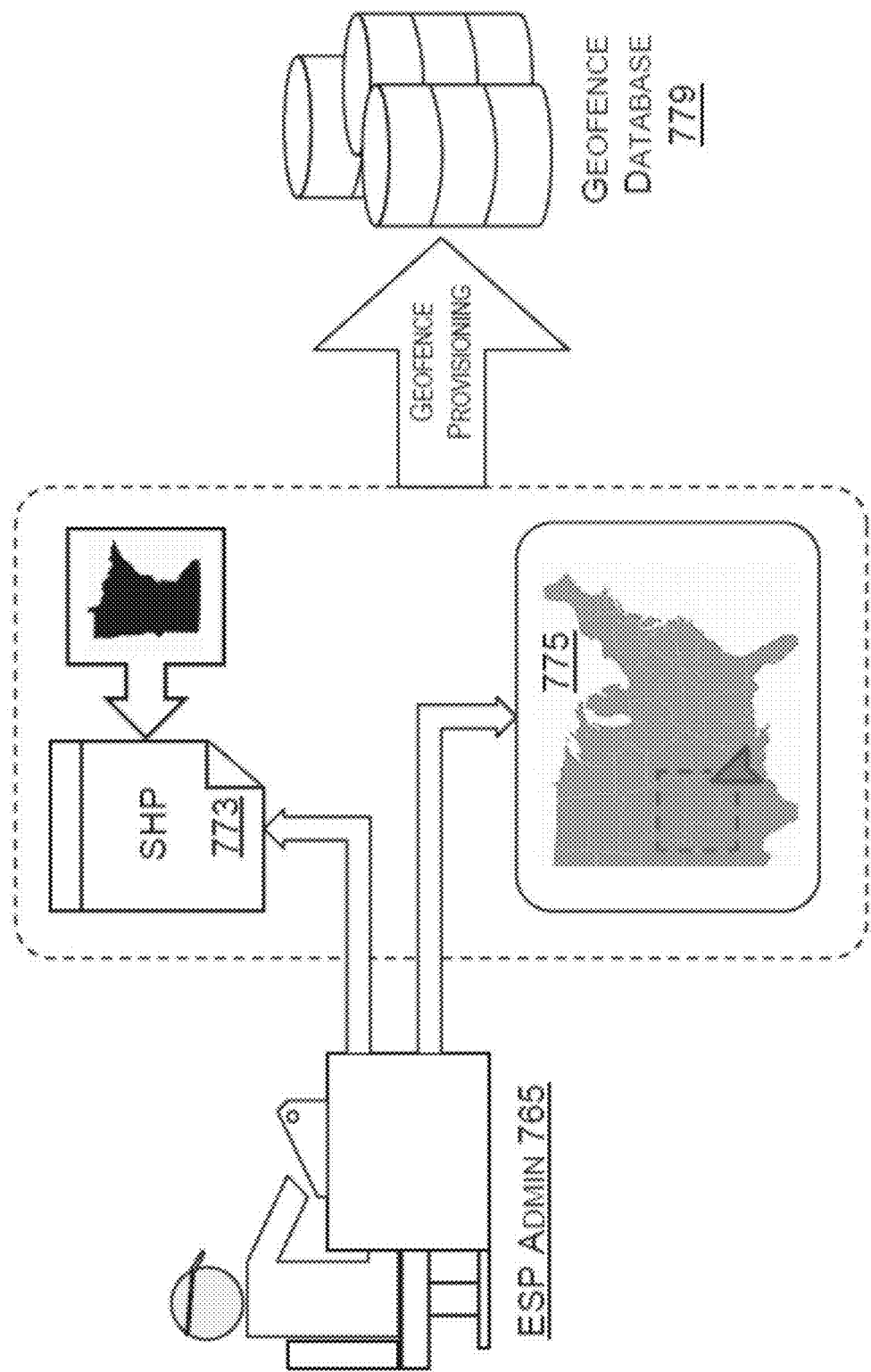
FIG. 7 depicts a flow diagram of an emergency data retrieval process.

Raw geofences may be pre-processed to generate processed geofences using a variety of techniques (e.g., before provisioning as shown in FIG. 7. For removing irregularities, a geofence may be processed to resolve overlaps, remove islands and projections, smooth boundaries, modifying the file format or size, etc.

In some cases, there may be overlap between geofence of two or more ESPs. In some embodiments, the emergency data may be shared with the two or more ESPs to err on the side of making mission critical information to all entities that may be involved in the emergency response. In some embodiments, the two or more ESPs are primary agencies (e.g., PSAPs) and the emergency data has to be shared with one appropriate ESP. To determine the appropriate ESP(s) for sharing emergency data, the authoritative jurisdiction (defined by one or more geofences) of the overlapping ESPs by checking with respective agency, geographical boundaries (national and international borders, county lines, rivers, hills, etc.), sample routing data, etc. In contrast, if the overlapping ESPs include one or more secondary ESPs, the overlap may be retained and emergency data may be shared with one or more ESPs (e.g., one primary agency and two secondary agencies).

In some embodiments, a buffer (e.g., +10 km) is added to the geofence(s) so that results within the buffer zone are also returned. In many cases, PSAPs have discretion and incentive to respond to emergencies that are beyond their authoritative jurisdiction. As an example, a geofence that is a circular area with a radius of 10 km would have an area of 100 π or ~314 km2, whereas the same area with a 10 km buffer around its circumference would have yield a combined radius of 20 km and a combined area of 400 π or ~1256 km2. In some embodiments, the buffer is from 0.5 km to 5 km, from 0.5 km to 10 km, from 0.5 km to 15 km, from 0.5 km to 20 km, from 0.5 km to 25 km, or from 0.5 km to 30 km. In some embodiments, the buffer is from 1 km to 5 km, from 1 km to 10 km, from 1 km to 15 km, from 1 km to 20 km, or from 1 km to 30 km. In some embodiments, the buffer is at least 0.1 km, at least 0.2 km, at least 0.3 km, at least 0.4 km, at least 0.5 km, at least 0.6 km, at least 0.7 km, at least 0.8 km, at least 0.9 km, at least 1 km, at least 2 km, at least 3 km, at least 4 km, at least 5 km, at least 6 km, at least 7 km, at least 8 km, at least 9 km, at least 10 km, at least 11 km, at least 12 km, at least 9 km, at least 14 km, at least 15 km, at least 16 km, at least 17 km, at least 18 km, at least 19 km, at least 20 km, at least 25 km, or at least 30 km. In some embodiments, the buffer is no more than 0.1 km, no more than 0.2 km, no more than 0.3 km, no more than 0.4 km, no more than 0.5 km, no more than 0.6 km, no more than 0.7 km, no more than 0.8 km, no more than 0.9 km, no more than 1 km, no more than 2 km, no more than 3 km, no more than 4 km, no more than 5 km, no more than 6 km, no more than 7 km, no more than 8 km, no more than 9 km, no more than 10 km, no more than 11 km, no more than 12 km, no more than 9 km, no more than 14 km, no more than 15 km, no more than 16 km, no more than 17 km, no more than 18 km, no more than 19 km, no more than 20 km, no more than 25 km, or no more than 30 km.

Figure 4:
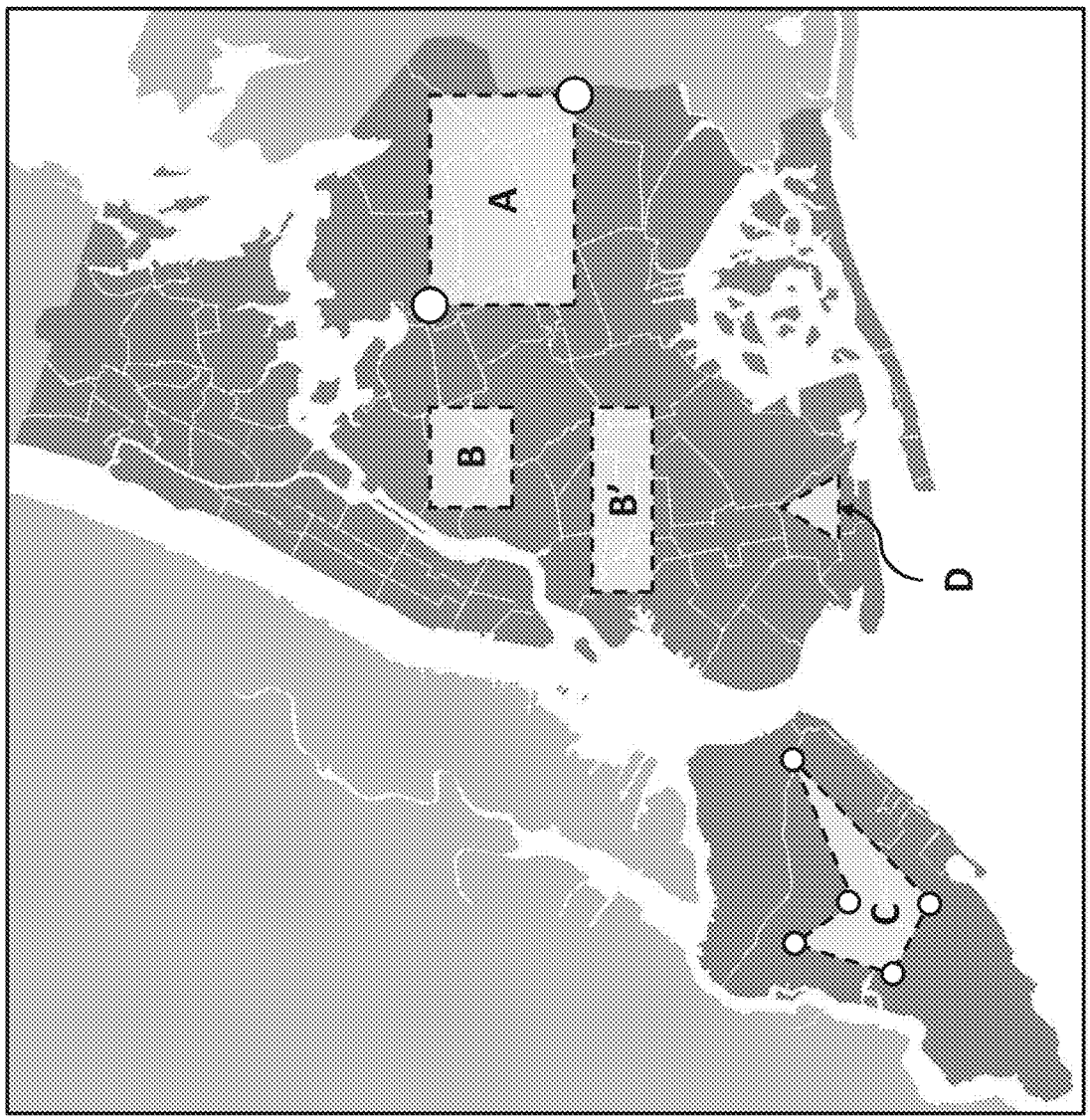
FIG. 4 depicts a diagram of an emergency response application system, in accordance with certain embodiments.

FIG. 4 illustrates non-limiting examples of geofence approximations that may be submitted as an "authoritative jurisdiction" for an ESP. One or more geofences enclose the geofenced region which is under the authoritative jurisdiction of an ESP. In some cases, the geofenced region may be a complex polygon, but it may be approximated using an appropriate shape. For example, a/rectangle (A), two disjointed rectangles (B, B'), a polygon with several sides (C) and a triangle (D), may represent different geofenced regions (defined by one or more geofences).

In some embodiments, an administrator of a PSAP submits the complex authoritative jurisdiction as one or more approximate geofence(s) by specifying points. For example, the PSAP administrator can submit geofenced region A by specifying two points—the north-west corner and the south-east corner using a drawing tool provided by the GUI of the emergency response application. In this example, the two points of the geofenced region are set using two latitude-longitude coordinates. In another example, the multiple-sided polygon C is submitted by specifying the five corners. In some embodiments, a PSAP administrator approximates a geofence for a PSAP by drawing one or more polygons using a drawing tool provided by the GUI of the emergency response application. In some embodiments, a geofence is generated using a series of points that are connected (e.g., entering three longitude-latitude points on a map to form a triangular geofence).

Approximating a complex geofenced region has several advantages. The geofence(s) are simple and the calculations can be quicker and less cumbersome for applications where exact calculations are not needed.

In some embodiments, a PSAP administrator can submit a GIS file (e.g., a shapefile) that represents the actual authoritative jurisdiction of the PSAP, which may then be provisioned in a geofence database. It is appreciated that a GIS file defining the authoritative jurisdiction may be saved in one or more industry-acceptable formats such as a shapefile, a GeoJSON file, KML file, etc. In some embodiments, the GIS file includes one or more features such as points, lines, polygons, density, and other shapes. A GeoJSON is open standard GIS file representing geographical features and non-spatial attributes based on JavaScript Object Notation. Some non-limiting examples of features include points (such as addresses and locations), line strings (streets, highways and boundaries), polygons (countries, provinces, tracts of land), and multi-part collections of these types. A Keyhole Markup Language (KML) file includes geographic annotations and visualization on internet-based maps on Earth browsers. A shapefile is a vector data format for storing the location, shape, and attributes of geographic features. A shapefile is stored in a set of related files, each of which may contain one feature class (e.g., lines, points, polygons, etc.). In some embodiments, the shapefile is a file with extension .SHP in ESRI file format where SHP is the feature geometry, SHX is the shape index position and DBF is the attribute data.

Various embodiments of the geofence database are contemplated. In some embodiments, one or more databases are searchable using a PSAP identifier, credentials, or other information. In some embodiments, an emergency location is searched through several geofences in the geofence database. In some cases, the geofenced region is shrunk for ease of storage and to simplify calculations.

As described above and below, in some embodiments, an emergency management system (EMS) utilizes geofences to determine the appropriate recipient of a particular set of emergency data received by the EMS. For example, as described above and below, in some embodiments, when the EMS receives an emergency alert that includes an emergency location, the EMS can utilize a geofence system to identify a geofence that the emergency location falls within. In response, the EMS can transmit the emergency location, any other emergency data included in the emergency alert (e.g., a user identifier or device identifier, a timestamp, etc.), or any other emergency data otherwise associated with the emergency alert to the entity (e.g., an ESP) associated with the geofence that the emergency location falls within. The geofence system, in this sense, can be understood as a routing system for emergency data.

Figure 5:
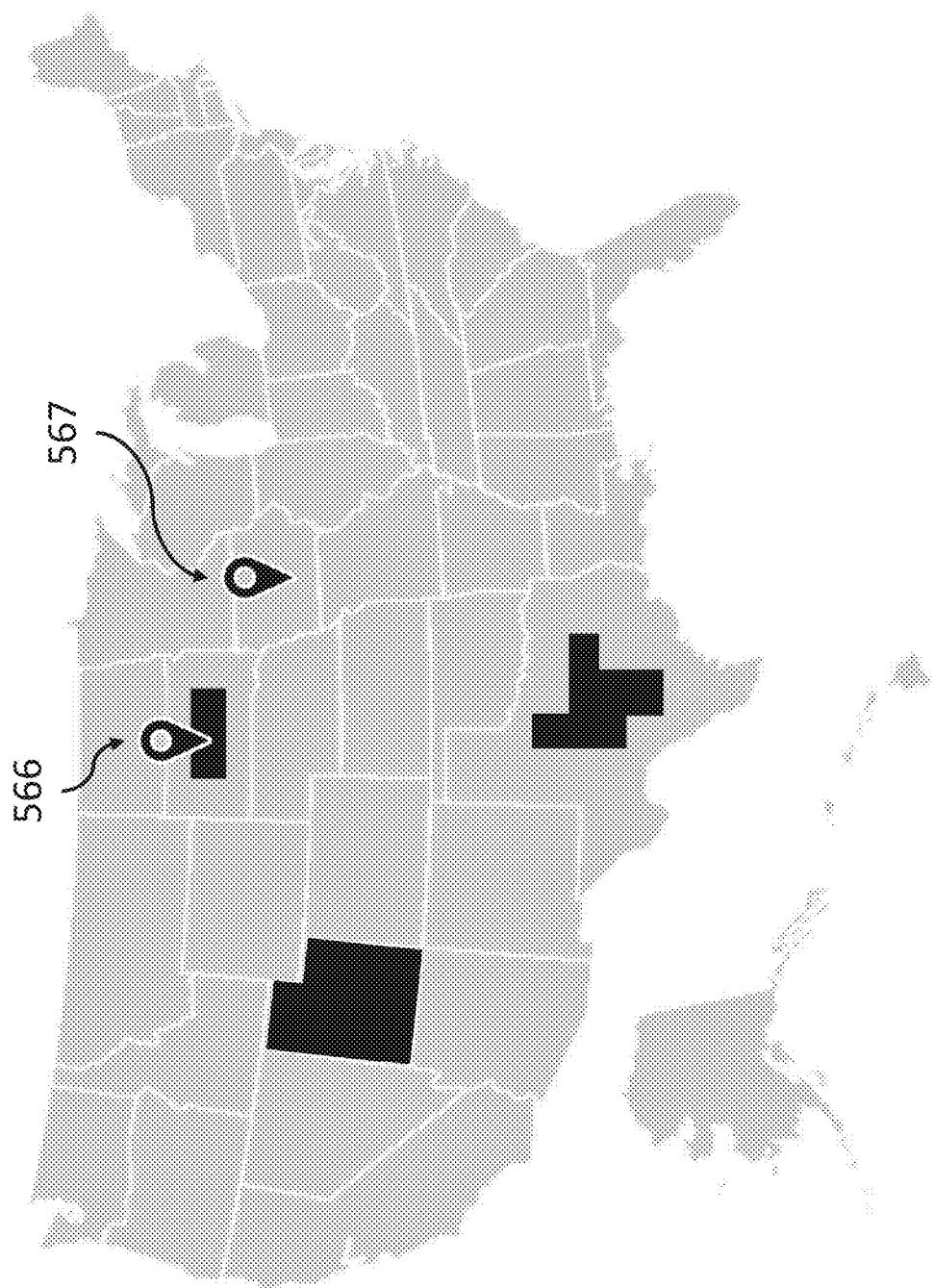
FIG. 5 illustrates a graphical user interface provided by an emergency response application, in accordance with certain embodiments.

FIG. 5 illustrates non-limiting examples of geofenced regions defined by one or more geofences within the United States. As shown, the geofenced region (e.g., an authoritative jurisdiction) may comprise an entire state (P), a complex shape within a state (Q), and a simple (rectangle) shape (R). As described in FIG. 3, the clearinghouse 350 will return the emergency location if it is within the retrieval geofence(s) associated with the credentials in the emergency data request. Referring back to FIG. 5, if an ESP member or user associated with geofenced region R is requesting an emergency location using the device identifier at location 566 and 567, the emergency location 566 will be returned, while emergency location 567 will be returned as an "unavailable location."

In some embodiments, geofences may be defined on a grid mesh including equal-sized rectangles or grids, for example, on the entire United States. In such scenarios, the gridlines may be used as geofences to define geofenced region comprising each grid. Such grid-geofences may be used as other geofences for filtering, reporting and monitoring emergency data.

Figure 6:
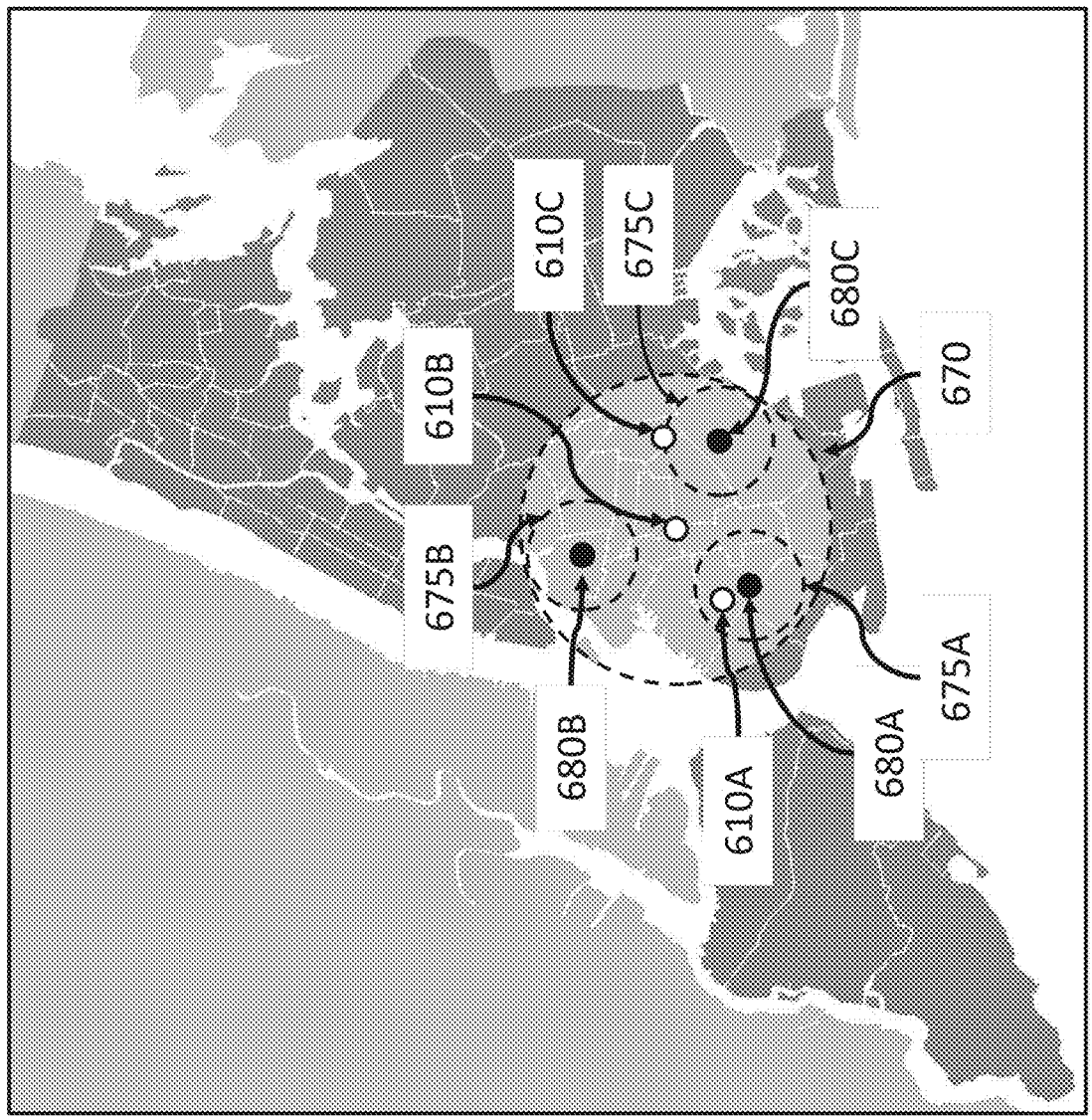
FIG. 6 illustrates a graphical user interface provided by an emergency response application, in accordance with certain embodiments.

FIG. 6 illustrates non-limiting examples of sub-jurisdictions within a larger geofenced region. As described, sub-jurisdiction geofences may be used for filtering, monitoring and visualizing emergency data. In addition, the sub-jurisdiction geofences may also be used for allocating and managing emergency responders. For example, several ESPs or responders may be serving the geofenced region 670. Geofencing can combine awareness of one or more emergency responders with awareness of the responder's proximity to locations where emergencies may be occurring (white dots 610A, 610B, 610C). To mark a responder location (black dots 680A, 680B, and 680C), its latitude, longitude and altitude can be specified. To adjust for proximity, a proximity radius can be added (see 675A, 675B, 675C). The latitude, longitude, and radius define a geofence, creating a circular area, or fence, around the location of the responder.

Various ways of using of proximity radius and assigned jurisdictions for visualizing and responding emergencies are contemplated. In another example, the region 670 is assigned to a police station, which may send officers to respond when the emergency situations arise. In this example, several police officers (black dots 680A, 680B, and 680C) may be assigned a specific beat 675A, 675B, and 675C (in various shapes) to monitor and emergencies occurring within each area.

Various scenarios are contemplated based on where the emergency is occurring. For example, when an emergency occurs in emergency location 610A, it is clearly within officer 680A's assigned jurisdiction and he or she may be first contacted to respond. In some situations, officer 680A may visualize the location of the emergencies and give priority to the emergency that is occurring within his or her beat. In contrast, in the case of emergency location 610C, the emergency is on the boundary of the officer 680C. Finally, emergency location 610B is occurring outside the sub-jurisdictions of all the officers and one of the officers may volunteer to respond to the emergency. In some embodiments, the geofence may be used to not allow one or more officers to view emergencies outside its main jurisdiction or sub-jurisdiction or outside a proximal radius based on the policy of the police station. It is contemplated that a police administrator (e.g., a police chief) may define the sub-jurisdictions or proximal radius to administer the geofenced region 670.

FIG. 7 depicts the process of provisioning and indexing of geofences. Generally, the process includes a geofence submission unit 776 (not marked) and a geofence provisioning unit 778 (not marked). As shown, an ESP administrator 765 can submit a GIS file 773 (e.g., a shape file) for the actual authoritative jurisdiction 775 of the ESP agency or organization, which may be provisioned in a geofence database 779.

It is appreciated that a GIS file 773 defining the authoritative jurisdiction may be saved in one or more industry-acceptable formats such as a GIS shape file, a GeoJSON file, KML file, etc. The GIS file may include various features such as points, lines, polygons, density, etc. A GeoJSON is open standard GIS file representing geographical features and non-spatial attributes based on JavaScript Object Notation. Some non-limiting examples of features include points (such as addresses and locations), line strings (streets, highways and boundaries), polygons (countries, provinces, tracts of land), and multi-part collections of these types. A Keyhole Markup Language (KML) file includes geographic annotations and visualization on internet-based maps on Earth browsers. A GIS shape file is a vector data format for storing the location, shape, and attributes of geographic features. A shapefile is stored in a set of related files, each of which may contain one feature class (e.g., lines, points, polygons, etc.). In some embodiments, the GIS shape file is a shape file with extension .SHP in ESRI file format where SHP is the feature geometry, SHX is the shape index position and DBF is the attribute data.

In some embodiments, the ESP administrator 765 submits one or more geofence(s) for provisioning a geofence database 779 as described in FIG. 5. For example, an approximated geofenced area 775 can be submitted using a shape file. In another example, the geofence may be submitted in one or more formats such as .shp, .shx, .dbf; .xml, .prj, .sbn, .sbx, .cpg, GeoJSON, etc., in a zipped folder. In some embodiments, the geofences is converted a common format for pre-processing (e.g., GeoJSON).

The credentials of the ESP administrator 765 can be matched to the ESP agency or organization (associated with an ESP account such as a PSAP identifier) and used for provisioning the submitted geofences in the provisioning unit 778. In some embodiments, the geofences are provisioned into a geofence database 779.

Various embodiments of the geofence database 779 are contemplated. It may be one or more databases that may be searchable using an ESP identifier (e.g. PSAP identifier), ESP account, user credentials, by state, etc. In some embodiments, an emergency location (e.g. from an emergency alert) may be matched with one or more geofences in the database 779 (as described in the jurisdictional awareness views in FIGS. 12, 13A-13C. In some cases, the geofenced region may be shrunk for easy of storage and to simplify calculations.

Emergency Response Application

Figure 8A:
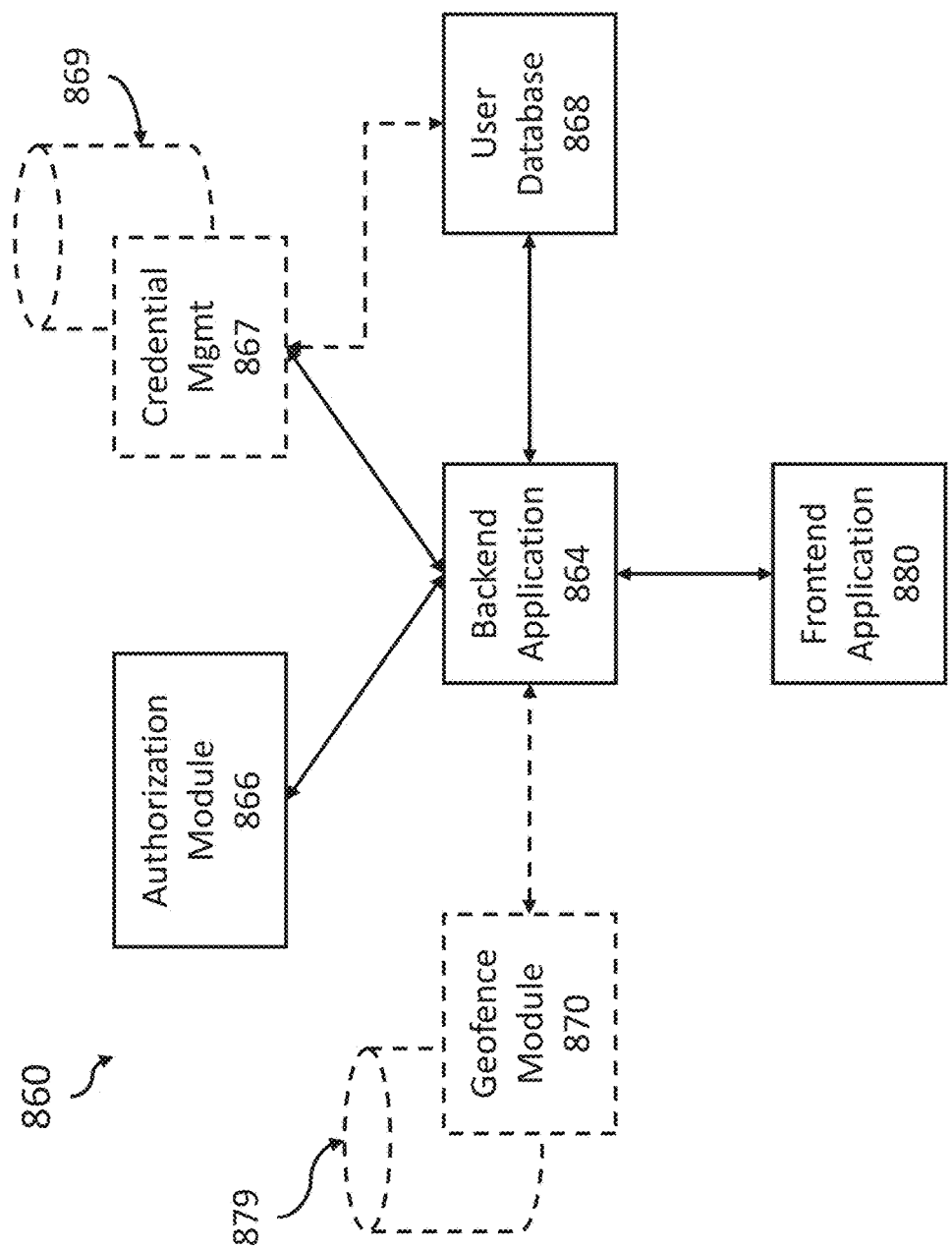
FIG. 8A depicts a system diagram for the credentialing and jurisdictional provisioning systems, in accordance with certain embodiments.

As mentioned above, in some embodiments, an emergency management system (EMS) autonomously and automatically transmits emergency data to an emergency data recipient (e.g., an emergency service provider (ESP)) for display within an emergency response application. FIG. 8A depicts a diagram of an emergency response application 860. In some embodiments, the emergency response application 860 includes a frontend application 880 (hereinafter "graphical user interface" or "GUI"), a backend application 864, an authorization module 866, and a user database 868. In some embodiments, the emergency response application 860 additionally or alternatively includes a credential management system 867 or a geofence module 870. In some embodiments, the credential management system 867 and the geofence module 870 are external to the emergency response application 860 and communicatively coupled to the emergency response application 860. In general, the components of the emergency response application 860 function to provide a graphical user interface for users (e.g., employees of a PSAP) to register for access to the emergency data stored within the clearinghouse, deliver emergency data requests to the clearinghouse, and receive emergency data from the clearinghouse. In some embodiments, the components of the emergency response application 860 additionally function to provide a graphical user interface for users to submit geospatial representations of jurisdictions (hereinafter, "geofences"), which is optionally used by the EMS to protect potentially sensitive emergency data stored within the clearinghouse, as described above. In some embodiments, geofences are used to route emergency data to an appropriate emergency data recipient, as described above and below.

In some embodiments, users interact with the emergency response application 860 using the frontend application, or graphical user interface (GUI) 880. In some embodiments, the GUI 880 is a webpage that is accessible through a web browser. In some embodiments, the GUI 880 is accessed through a desktop application. In some embodiments, the GUI 880 contains one or more pages each with their own plurality of interactive elements, such as, but not limited to, entry fields, soft buttons, sliders, maps, images, and videos. In some embodiments, the interactive elements of the GUI 880 are configured to instruct the GUI 880 or the backend application 864, or both, to perform various operations. As an example, a soft button (e.g., a "next" button) instructs the GUI 880 to navigate from one page to another. Another soft button (e.g., a "submit" button) instructs the GUI 880 to navigate from one page to another while concurrently instructing the backend application 864 to store and/or process information submitted by a user into an entry field elsewhere within the GUI 880. In some embodiments, the backend application 864 functions to receive inputs from the GUI 880 and coordinates the functions of the authorization module 866, the credential management system 867, the user database 868, and the geofence module 870 to receive emergency data from the clearinghouse and display the emergency data to the users of the emergency response application 860. In some embodiments, one or more geofences are stored within one or more geofence databases 869 accessible by the geofence module 870.

Figure 8B:
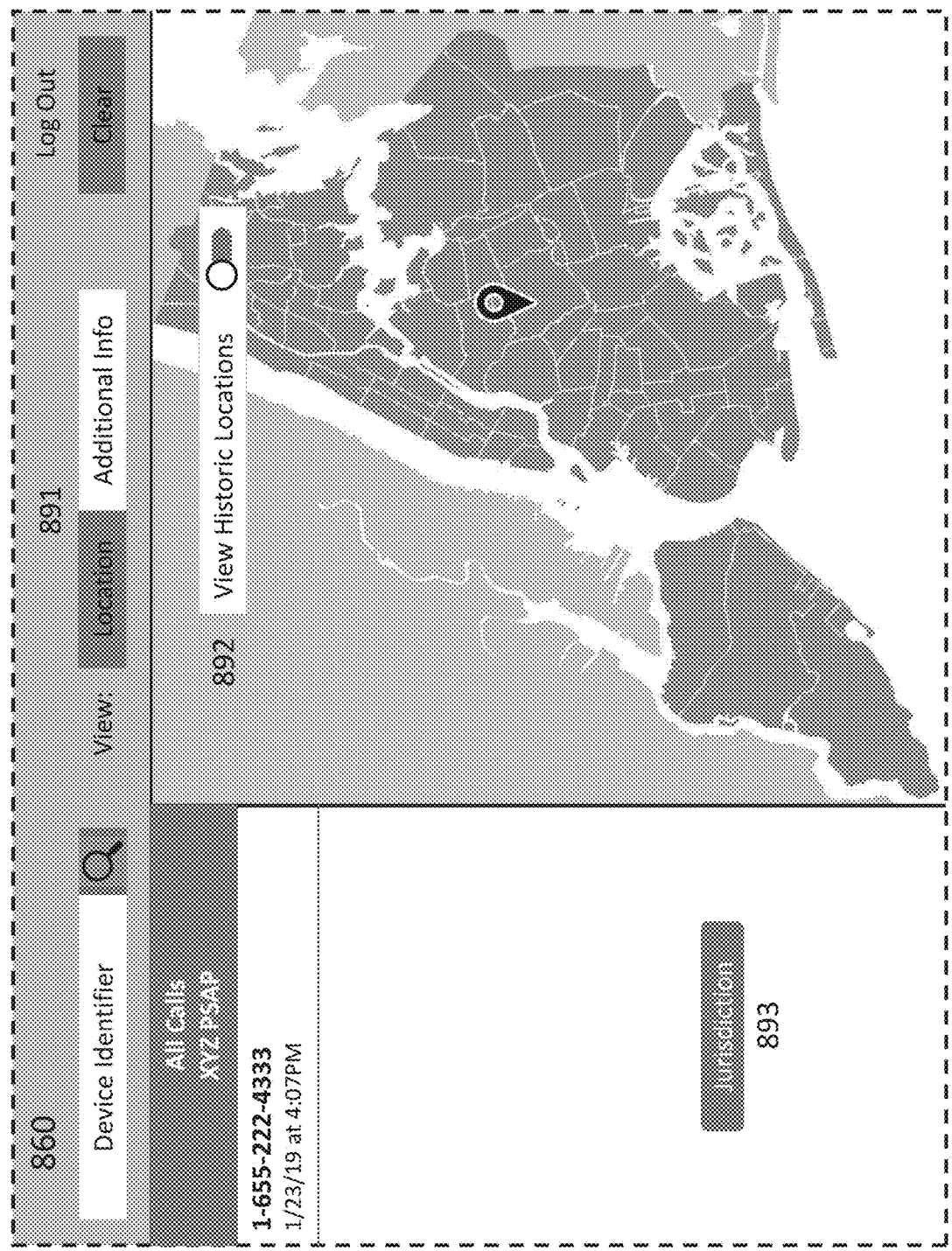
FIG. 8B illustrates a graphical user interface provided by an emergency response application, in accordance with certain embodiments.

In some embodiments, the emergency response application GUI 880 is customizable. FIG. 8B depicts a non-limiting example of an emergency response application webpage GUI. In some embodiments, the GUI is configurable to display information relevant to the individual authority. In some embodiments, the GUI is configurable to restrict information from being accessed by an individual authority. For example, the GUI available to a PSAP administrator may display options to access sensor data, traffic data, video data and historical and live location data while a GUI used by a first responder may display live location data, personal medical data, and traffic data. In some embodiments, the individual features of the GUI are customizable, such that a user can enable or disable functionalities and/or data streams 891. For example, a user may enable or disable a historic location overlay 892. In another example a user may enable or disable personal medical information associated with the device identifier. In some embodiments, the individual features of GUI are able to be arranged by the user according to the user's preferences. In some embodiments, features of the GUI are made available based on a user's proximity to an emergency. For example, a first responder may gain access to a medical data associated with a device identifier when the first responder is 5000, 2000, 1000, or 500 meters or less from the emergency. In some embodiments, the GUI includes a functionality to enable and disable an active communication link (e.g., a websocket connection) 893 that, when enabled, prompts the EMS to automatically push emergency data to the emergency response application 860, as described below.

As mentioned above, in some embodiments, the emergency response application 860 is a webpage that can be accessed through an internet or web browser. In such embodiments, the emergency response application 860 can be quickly and easily integrated into the systems used by emergency service providers (ESPs), such as public safety answering points (PSAPs), because accessing and using emergency response application 860 requires no additional software or hardware outside of standard computing devices and networks. As previously discussed, one of the greatest hindrances that PSAPs face in providing emergency assistance to people experiencing emergency situations is in acquiring accurate locations of the emergencies and the people involved, because PSAPs are currently typically limited to verbally asking for and verbally receiving locations from callers. In some embodiments, the clearinghouse is capable of receiving accurate locations (as well as additional emergency data, as described above) from electronic devices such as smartphones and delivering the accurate locations to the appropriate PSAPs during emergency situations. Therefore, it is advantageous to provide the emergency response application 860 to PSAPs in the form of a webpage accessible through a standard web browser, in order to provide the potentially life-saving information stored within the clearinghouse to those capable of providing emergency assistance as quickly and easily as possible.

Figure 9A:
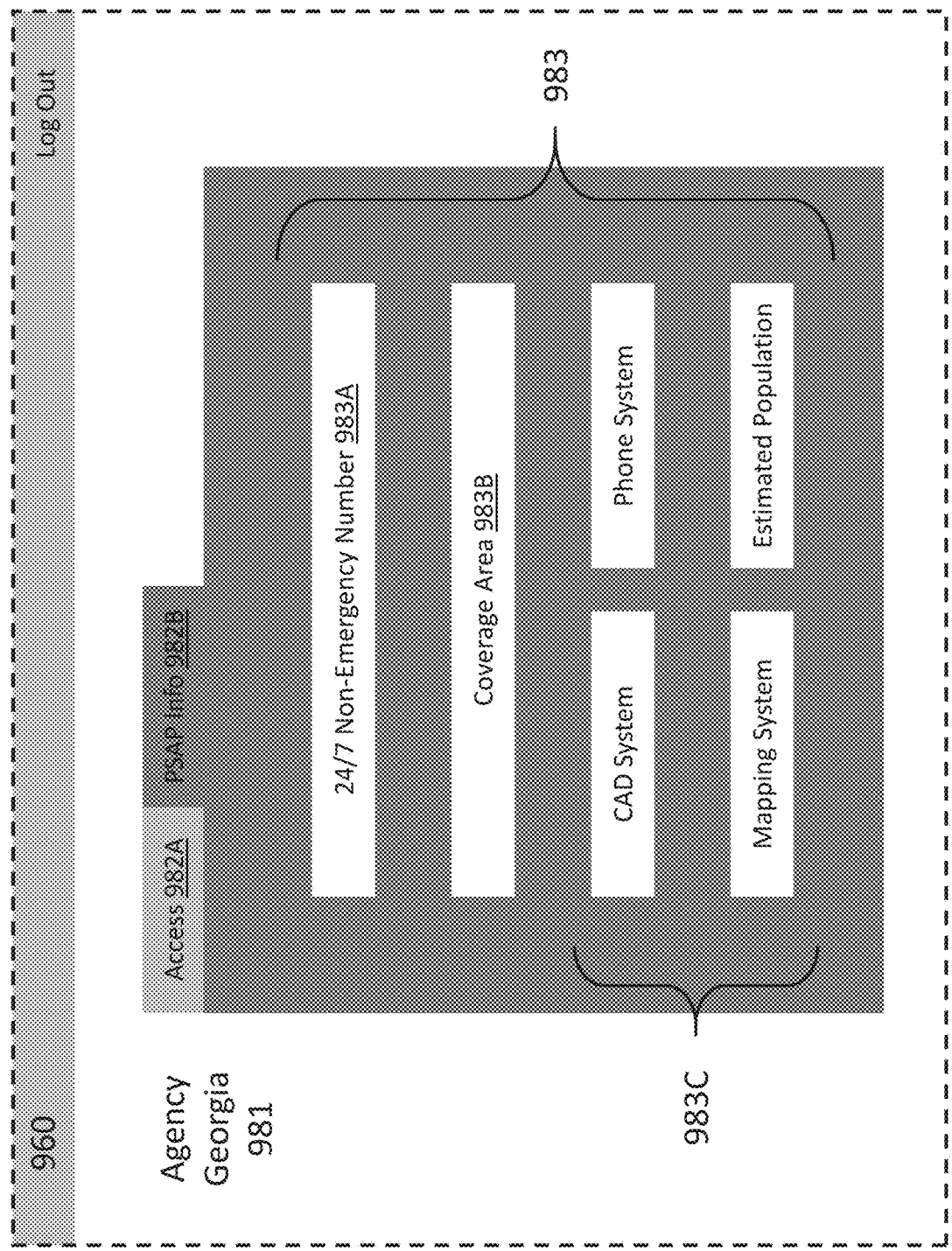
FIG. 9A and FIG. 9B illustrate a graphical user interface provided by an emergency response application, in accordance with certain embodiments.

In providing the emergency response application 860 to ESPs (and the potentially sensitive emergency data stored within the clearinghouse, by extension) in the most accessible way possible, it is advantageous to provide rigorous security precautions and functions specifically created and suited for the emergency response application 860, as will be described below. In some embodiments, if an ESP desires to access the emergency data stored within the clearinghouse, an administrator of the ESP (hereinafter, "ESP administrator" or "ESP admin") can navigate to the emergency response application 860 using a URL in a standard web browser. The ESP administrator can then use interactive elements of the GUI 880 to request access to the clearinghouse using the emergency response application 860. In some embodiments, upon selecting to request access to the emergency response application 860, the emergency response application 860 prompts the ESP administrator to submit information 983 about the ESP through the GUI 880, as depicted in FIG. 9A. In some embodiments, the information about the ESP includes the name of the ESP (hereinafter, "ESP name") 981, a non-emergency hardline telephone number of the ESP (hereinafter, "non-emergency number") 983A, the coverage area or jurisdiction of the ESP 983B (e.g., a geofence), and other information 983C. In some embodiments, other information 983C includes at least one of a type of computer aided dispatch (CAD) system used by the ESP (e.g., a PSAP), a type of phone system used by the ESP, a type of mapping system used by the ESP, and an estimated population covered by the ESP (i.e., an approximate number of people who reside within the jurisdiction of the ESP). In some embodiments, the ESP administrator can use interactive elements to define a geofence representing the jurisdiction of the PSAP 983B, as described above. In some embodiments, the ESP is not granted access to the emergency response application 860 if some or all of the information 983 is not submitted by the ESP administrator. In some embodiments, the ESP administrator edits or resubmits the information 983 about the ESP by selecting the ESP Information tab 982B. In some embodiments, after the ESP is granted access to the emergency response application 860 and/or the clearinghouse, the ESP administrator can create accounts for other employees or members of the ESP by selecting the Access tab 982A, as described below. In some embodiments, after a request for access to the emergency response application 860 is received by the emergency response application 860, an organization is created for the requesting PSAP within the credential management system 867 and an account node is created for the PSAP administrator within the credential management system 867 and linked with the organization, as described below.

In some embodiments, after the ESP administrator submits a request for access to the emergency response application 860 and/or the clearinghouse, the emergency response application 860 creates an account for the ESP administrator and stores the account for the ESP administrator in the user database 868. In some embodiments, the account created for the ESP administrator includes information about the ESP administrator such as, but not limited to, the name of the ESP administrator, an email address and/or telephone number of the ESP administrator, a system identifier (hereinafter "system ID") for the ESP administrator, and an identifier of the ESP (e.g., the name of the ESP 981). In some embodiments, the request for access to the emergency response application 860 submitted by the ESP administrator must be verified before the ESP administrator is given further access to the emergency response application 860. For example, in some embodiments, the request for access must be verified before the ESP administrator is granted the ability to perform functions such as creating accounts for other employees or members of the ESP or requesting emergency data through the emergency response application 860. In some embodiments, requests for access to the emergency response application are manually verified by public safety professionals, such as by communicating with local government agencies to determine that the information 983 about the ESP requesting access is true and correct. In some embodiments, requests for access to the emergency response application are automatically verified by the EMS or emergency response application 860 if all of the information 983 about the ESP requesting access correctly match previously received or confirmed information. In some embodiments, if some or all of the information 983 about the ESP requesting access is determined to be untrue or false, the request for access to the emergency response application 860 is denied. In some embodiments, if some or all of the information 983 about the ESP requesting access is determined to be untrue or false, the request for access is denied and the ESP is flagged for further investigation.

Figure 9B:
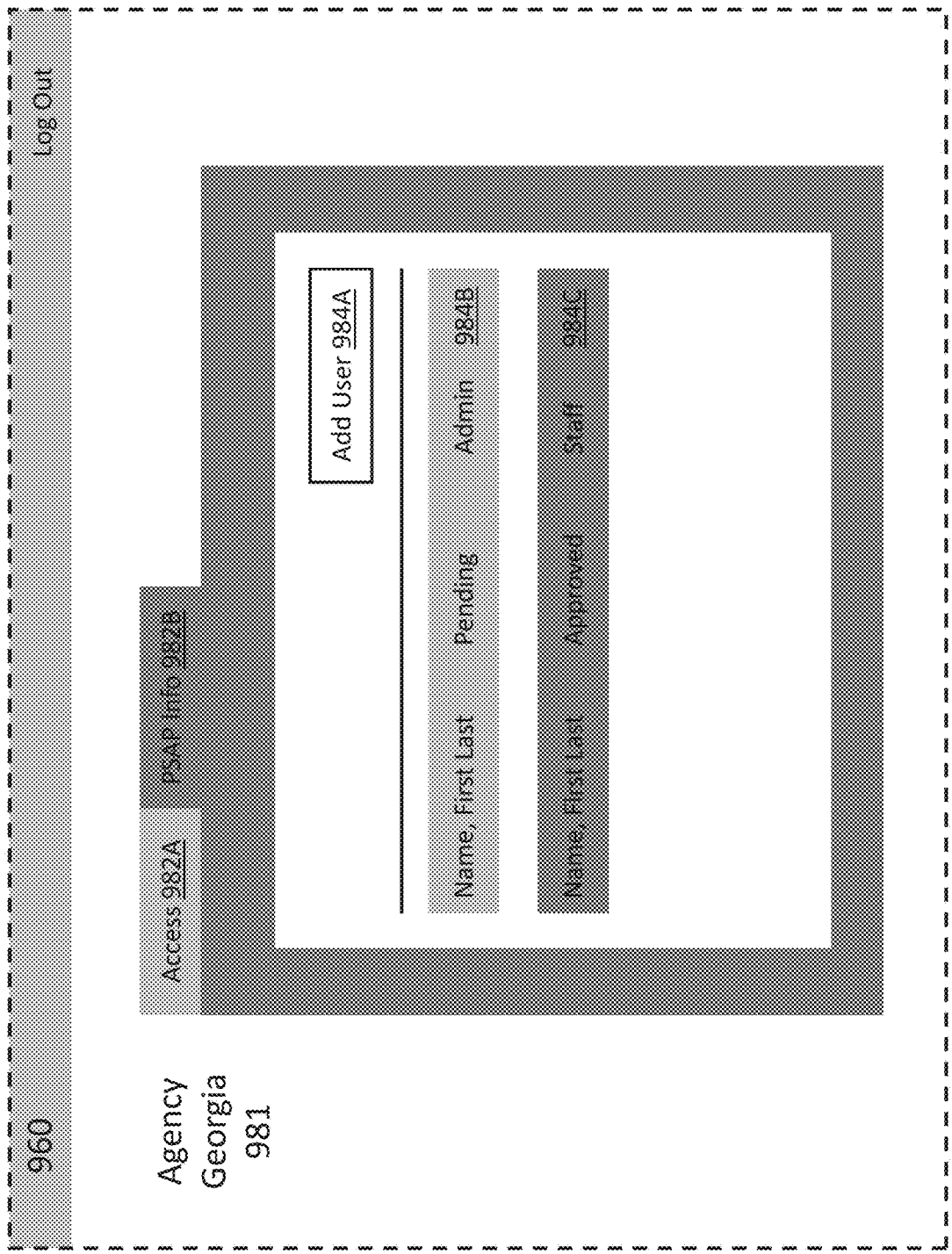

In some embodiments, after an account is created for the ESP administrator in the user database 868, the ESP administrator can create accounts for employees or other members of the ESP. In some embodiments, the emergency response application 860 will not allow an ESP administrator to create accounts for other members of the PSAP until a request for access to the emergency response application from the ESP administrator is verified. In some embodiments, to create an account for another member of an ESP, the ESP administrator can select the Access tab 982A. Selecting the Access tab 982A then prompts the emergency response application to display a list of accounts associated with the particular ESP. For example, FIG. 9B depicts a list of accounts associated with the "Georgia" PSAP, which includes a PSAP administrator account 984B and a PSAP staff account 984C. In this example, although the PSAP administrator account 984B is pending approval (e.g., by a public safety professional, as described above), the PSAP staff account 984C has already been approved. In some embodiments, the emergency response application 860 includes a predefined set of account types with different levels of access to functions within the emergency response application 860. For example, in some embodiments, accounts created within the emergency response application must either be administrator accounts or staff accounts. In some such embodiments, administrator accounts have full access to the functions of the emergency response application, including, but not limited to, editing information 983 about the ESP, creating new accounts, and requesting emergency data. In some embodiments, the staff account lacks the full access of the administrator and/or only has the ability to request emergency data. In some embodiments, ESP administrators define custom account types and designate which functions of the emergency response application 860 are accessible by the respective custom account types.

After selecting the Access tab 982A, an ESP administrator can create a new account for an ESP by selecting the Add User button 984A. In some embodiments, after selecting the Add User button 984A, the emergency response application 860 prompts the ESP administrator to select an account type 985A for the new account, as depicted in FIG. 9B. In some embodiments, as described above, the account types include administrator accounts and staff accounts. In some embodiments, the account types include a token, which can be used to automate the login process. In addition to the account type, the emergency response application 860 prompts the ESP administrator to submit an email address 985B for the user of the new account. Upon submission of the account type and email address, the emergency response application creates a new account within the user database 868 and populates the new account within the user database 868 with the account type and the email address. In some embodiments, an email including a confirmation link is sent to the email address, and the emergency response application 860 does not allow access to the new account until the confirmation link is selected. In some embodiments, the email additionally or alternatively includes a temporary password for the new account. In some embodiments, an ESP administrator creates an account for another member of the ESP before the request for access to the emergency response application 860 is approved. However, in some embodiments, neither the ESP administrator nor any account other created by the ESP administrator can access emergency data stored within the clearinghouse until after the request for access to the emergency response application 860 has been approved. In some embodiments, when a new account is created within the user database 868, a new account node is concurrently created for the new account within the credential management system 867, as described below. In some embodiments, access keys or credentials allow for differential access to different recipients, as described below.

Authentication, Credentials & Roles

To ensure the security, privacy and integrity of the data provided to the ESP, proper authentication may be required at various steps. The authorization process may require the ESP member or user of the emergency response application to verify their identity through the use of credentials such as log-in password, config file (e.g., a configuration created in a third-party system), etc. In some embodiments, the ESP member provides fingerprint, voice command, etc. to log-in, which can be verified.

Various types of credentials may be utilized as a part of the authentication process. Credentials may be generated, stored, verified and validated by the EMS. For example, the credentials may be generated, but must be verified (e.g., phone verification) before use. In some embodiments, the credentials are valid for a specific duration of time (e.g., 1 minute, 5 minutes, 1 hour, and 24 hours). Some non-limiting examples of credentials that can be used are access keys, admin credentials, time-limited tokens, etc. In some embodiments, credentials are transmitted through secure pathways (e.g., using encryption).

In some embodiments, credentials are used in a two-step authentication process. For example, the authentication may require: (i) a log-in and password for the ESP member to log-in the ESP system and (ii) a time-limited token to be generated based on an authentication request. In some embodiments, a role (as described above) may be combined with to create a three-step authentication process. For example, an administrator of the ESP could have designated roles for various ESP members and selected specific data categories to be made accessible for each role.

In contrast to system-generated credentials which must be created, stored and managed in specific ways, roles can be assigned by the admin to each member of the ESP. For example, roles can include admin, agent, call taker, supervisor, manager, etc. In contrast to credentials, roles do not need to be verified by system as they are usually admin-defined. In addition, the admin can update the role of an ESP member to accurately reflect changes in jobs, positions and responsibilities. In this way, the use of the roles allows the admin to customize the management portal to reflect the organizations under their supervision. In some embodiments, an ESP member can have multiple admin-defined roles.

In some embodiments, the ESP member or user is subscribed to the emergency data received within the ESP jurisdiction, as described above and below. In this way, the credential system ensures that emergency data that is relevant for the ESP member is accessible and updates are available quickly and efficiently.

Due to the diversity of ESP members (e.g., call dispatcher, PSAP manager, police, and paramedic) and the need for accurate and relevant data, there are specific challenges for emergency response. Although system-defined credentials may also be used to restrict access to emergency data, admin-defined roles were incorporated to allow the customization needed for different ESP members. In this way, the present system allows for both secure authentication and significant customizations for managing access to emergency data for various members of the organization.

Credential Management System & User Database

As previously discussed, it is advantageous to provide rigorous security precautions and functions specifically created and suited for the emergency response application 860 in such embodiments wherein the emergency response application 860 is accessible as a webpage through standard web browsers. In some embodiments, as mentioned above, the emergency response application 860 includes a user database 868 and is communicatively coupled to a credential management system 867. In such embodiments, the user database 868 and the credential management system 867 function cooperatively to secure the emergency response application 860 and the emergency data stored within the clearinghouse. Unlike the emergency response application, which can be accessed through public networks and servers, the credential management system 867 can be securely connected to the clearinghouse through private networks and servers. In this sense, the credential management system 867 can serve as a protective barrier between the emergency response application 860 and the clearinghouse, as described below.

In some embodiments, when an ESP administrator (e.g., a PSAP administrator) requests access to the emergency response application 860 on behalf of an ESP, an organization (also referred to as an "org") is created for the ESP within the credential management system 867. Concurrently, an organization identifier (also referred to as an "org ID") is created for the organization within the credential management system. When the request is granted, a long-lived credential (hereinafter, "credential") is created for the ESP within the credential management system 867. In some embodiments, the credential never expires. In some embodiments, the credential expires after an extended period of time, such as a year. In some embodiments, multiple credentials are created for a single organization. As an example, in the event that a credential is compromised, the credential is deactivated, and a new credential is created for the organization. Alternatively, multiple credentials are created for a single organization, and in some embodiments, the credential management system 867 periodically cycles through the credentials by activating one and deactivating the others to provide an additional layer of security.

In some embodiments, whenever an account is created within the emergency response application 860, the account is stored within the user database 868 and populated with information regarding the account, such as a name of the ESP member for which the account was created, an email address, and the name of the ESP. In some embodiments, a temporary password is created for and stored with the account in the user database 868. Concurrently with storing the account within the user database 868, an account node is created within the credential management system 867 and a system ID is generated for the account node. The emergency response application 860 then stores the system ID in the account stored within the user database 868. In this way, the system ID serves as a link between an account stored within the user database 868 and a correlated account node stored within the credential management system 867. The emergency response application 860 then requests information regarding an account node stored within the credential management system 867 using the system ID associated with the account node, as described below. In some embodiments, organizations, organization IDs, users, and system IDs, and credentials are stored within a credential management system database 869. In some embodiments, the credential management system 867 is a software module included in the EMS. In some embodiments, the credential management system 867 is a third-party service. As an example, an API management service, such as Apigee, may be used as a credential management system.

Login Flow

In some embodiments, once a request for access to the emergency response application 860 from an ESP administrator has been approved, the ESP administrator and any account created by the ESP administrator is able to log into the emergency response application 860 and request emergency data from the clearinghouse through the emergency response application 860. To log into the emergency response application 860, any account holder (i.e., registered user) can navigate to a login page within the GUI 880 of the emergency response application 860 and submit the email address and password associated with their account (e.g., "login information"). If the login information is correct, the emergency response application 860 can grant the account holder access to the emergency response application 860 and display the dashboard within the GUI 880, as depicted in FIG. 8B. In some embodiments, alternate information is used as login information. For example, in some embodiments, login information comprises a username, employee ID, or other suitable identifying information for an account holder.

In some embodiments, the emergency response application 860 or EMS maintains an authorized list (also referred to as a "whitelist") of internet protocol addresses (hereinafter, "IP addresses"). In such embodiments, only login attempts from IP addresses listed on the whitelist are granted access to the emergency response application 860. In some embodiments, when an ESP administrator requests access to the emergency response application 860 and the request is approved, as described above, the IP address from which the ESP administrator submitted the request is automatically added to the whitelist. In some embodiments, the whitelisted IP address from which the ESP administrator submitted the request is associated with the ESP administrator within the ESP administrator's account stored in the user database 868. In some embodiments, each additional account created by an ESP administrator (e.g., another ESP admin account or an ESP staff account) is associated by default with the whitelisted IP address from which the ESP administrator submitted the request to access the emergency response application 860 within the user database 868.

In some embodiments, when a user (e.g., an ESP admin or ESP staff member) attempts to log into the emergency response application 860 by submitting the email address and password for their account, the emergency response application 860 identifies the IP address of the computing device from which the user is attempting to login and cross-references the IP address with the whitelist of IP addresses. If the IP address is found on the whitelist of IP addresses, in addition to the email address and password being correct, the emergency response application 860 can grant the user access to the emergency response application 860. However, if the IP address is not found on the whitelist of IP addresses, the emergency response application 860 can deny the user access to the emergency response application 860. In some embodiments, in addition to denying the user access to the emergency response application 860, the emergency response application 860 can disable or deactivate the account with which the user attempted to login. In some embodiments, when a user attempts to log into the emergency response application 860 by submitting the email address and password for their account, the emergency response application 860 identifies the IP address of the computing device from which the user is attempting to login and cross-references the IP address with one or more IP addresses listed with the account. If the IP address is found within the one or more IP addresses listed with the account, in addition to the email address and password being correct, the emergency response application 860 can grant the user access to the emergency response application 860. However, if the IP address is not found within the one or more IP addresses listed with the account, the emergency response application 860 can deny the user access to the emergency response application 860 and/or disable or deactivate the account with which the user attempted to login.

Figure 10:
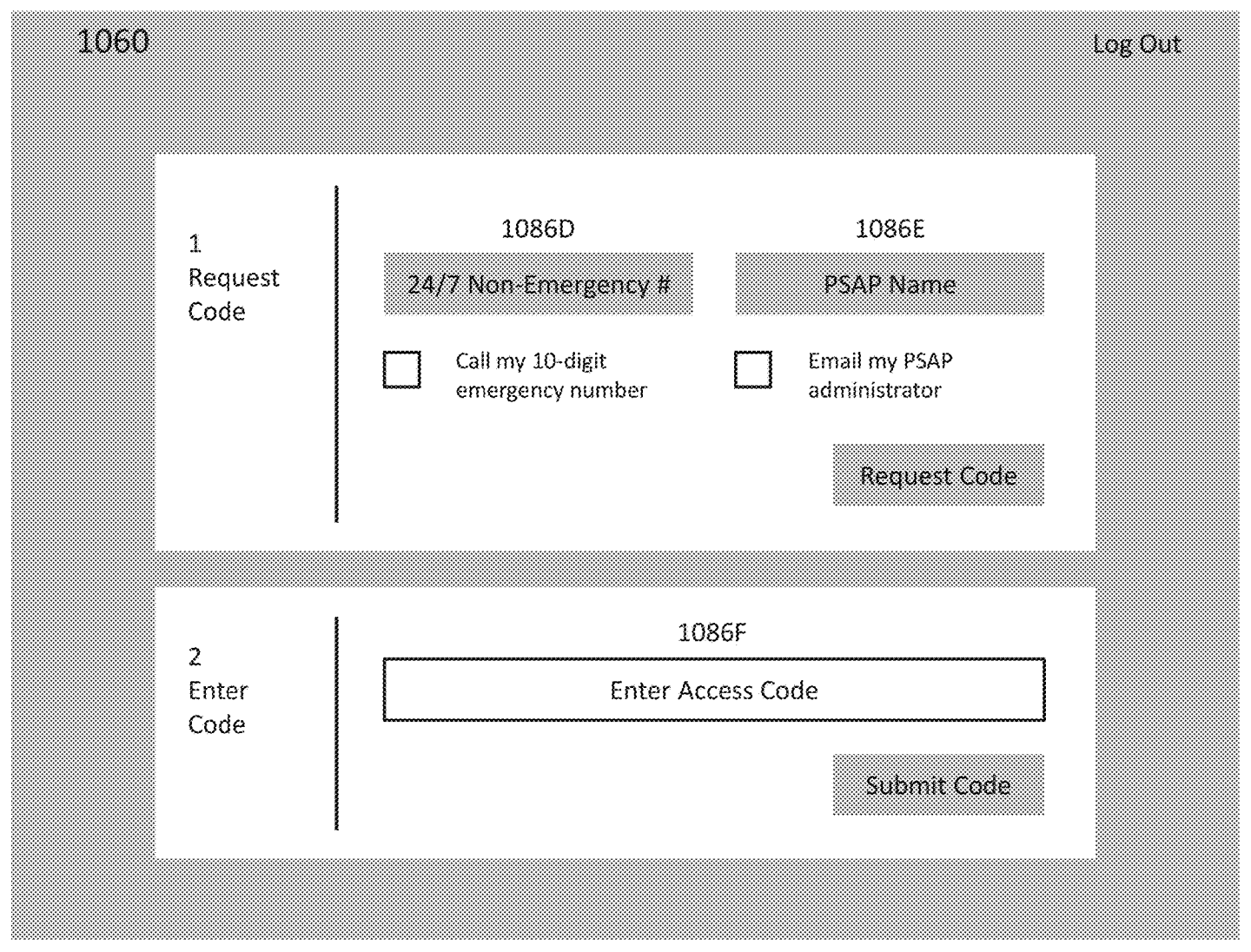

If an account is disabled or deactivated by the emergency response application 860 in response to receiving a login attempt from an unrecognized IP address (e.g., an IP address that is not found within the whitelist of IP addresses or an IP address that is not found within one or more IP addresses listed with the account), the account must be reactivated by the emergency response application 860 but the account can be used to access the emergency response application 860. In some embodiments, after disabling or deactivating an account, the emergency response application 860 presents options for requesting an access (or reactivation) code through the GUI 880, as depicted by FIG. 10. The access code can be used to reactivate the disabled account. For example, in some embodiments, the emergency response application presents an option to request an access code by receiving a phone call (e.g., an interactive voice response (IVR) call) to a non-emergency number associated with the ESP associated with the disabled account. In such an embodiment, the GUI 880 can present an entry field 1086D through which the non-emergency number can be submitted. After receiving a non-emergency number and confirming that the submitted non-emergency number is indeed associated with the proper ESP, the emergency response application 860 or EMS can deliver an IVR call to the non-emergency number of the associated ESP and playback an access code through the IVR call. This method ensures and confirms that whoever is attempting to log into the emergency response application from the unrecognized IP address is truly affiliated with the associated ESP, because to receive the access they must be physically present at the ESP or receive the access code from another person who is physically present at the ESP. In some embodiments, the IVR call is delivered using voice over internet protocol (VoIP). Once the access code is submitted to the emergency response application 860 (e.g., through the entry field 1086F), the emergency response application 860 can reactivate the disabled account. In some embodiments, after reactivating the disabled account, the emergency response application 860 can add the formerly unrecognized IP address to the whitelist of IP addresses. In some embodiments, after reactivating the disabled account, the emergency response application 860 can associate the formerly unrecognized IP address with the account within the user database 868.

In some embodiments, the emergency response application 860 can present an option to request an access code by delivering an email containing the access code to an ESP administrator associated with the disabled account. In such an embodiment, the GUI 880 can present an entry field 1086E through which an ESP name can be submitted. After receiving an ESP name through the entry field 1086E, the emergency response application 860 can identify an ESP administrator associated with the ESP name within the user database 868 and retrieve an email address of the ESP administrator from the ESP administrator's account. If the emergency response application 860 is unable to identify an ESP administrator associated with the ESP name within the user database 868, the emergency response application 860 can display an error message within the GUI 880. If the emergency response application 860 is able to identify to an ESP administrator associated with the ESP name within the user database 868, the emergency response application 860 can then deliver an email containing an access code to the ESP administrator's email address. This method similarly ensures and confirms that whoever is attempting to log into the emergency response application from the unrecognized IP address is truly affiliated with the associated ESP, because they must receive the access code from the ESP administrator, who has been previously verified. As described above, the access code can then be used to reactivate the disabled account. In some embodiments, the email sent to the email address of the ESP administrator additionally or alternatively includes a confirmation link that is selectable by the recipient of the email (i.e., the ESP administrator) to automatically reactivate the disabled account. Once the account has been reactivated, the emergency response application 860 can grant the account holder access to the emergency response application 860 and display the dashboard within the GUI 880, as depicted in FIG. 8B, and the user can use the emergency response application 860 to receive emergency data from the clearinghouse, as described below with respect to FIG. 11.

In some embodiments, when a user successfully logs into the emergency response application 860, such as by navigating to the emergency response application 860 within a web browser and submitting their login information through the GUI 880 (and the login information points to an authorized and/or active account, as described above), the emergency response application 860 retrieves the system ID associated with the user's account and sends an account information request including the system ID to the credential management system 867. In response to receiving the account information request from the emergency response application 860, the credential management system 867 can identify an account node correlated with the account and return information regarding the account node to the emergency response application 860. In some embodiments, the information regarding the account node includes the org ID associated with the organization to which the account node is linked. An example of a node is shown below.

```
{
"apps": [
  "lucas-rad-test",
  "CCInform-Sandbox"
],
"companies": [
  "neoteric",
  "test-company",
  "curbcall",
  "uber"
],
"email": "jsmith@rapidsos.com",
"developerId": "fc4fa636-a321-4e7b-a497-b3922df753a8",
"firstName": "John",
"lastName": "Smith",
"userName": "jsmith",
"organizationName": "rapidsos",
"status": "active",
"attributes": [ ],
"createdAt": 1475683130277,
"createdBy": "mjohnson@rapidsos.com",
"lastModifiedAt": 1511305645398,
"lastModifiedBy": "apigee-drupal+rapidsos_jevp@google.com"
```

In some embodiments, after receiving the information regarding the account node from the credential management system 867, the emergency response application 860 then sends a temporary access token request including the org ID to the credential management system 867. In response to receiving the temporary access token request, the credential management system 867 can identify a credential associated with the organization to which the org ID refers and generate a temporary access token based on the credential. In some embodiments, after receiving the information regarding the account node from the credential management system 867, the emergency response application 860 sends a credential request including the org ID to the credential management system 867. In response to receiving the credential request, the credential management system 867 can identify a credential associated with the organization to which the org ID refers and return the credential to the emergency response application 860. In this embodiment, the emergency response application 860 can then send a temporary access token request including the credential to the credential management system 867, which can in turn generate the temporary access token based on the credential and return the temporary access token to the emergency response application 860. In some embodiments, the emergency response application 860 sends the temporary access token request to the credential management system 867 only after the user navigates to the dashboard.

In some embodiments, the credential management system 867 generates the temporary access token by deriving the temporary access token from the credential. In some embodiments, the temporary access token expires after a predetermined duration of time, such as 24 or 48 hours. In some embodiments, the temporary access token expires when the user logs out of the emergency response application 860. In some embodiments, the temporary access token is a short-lived access token created under the OAuth 2.0 authorization protocol. After generating the temporary access token, the credential management system 867 can then return the temporary access token to the emergency response application 860. In some embodiments, the temporary access token is generated automatically upon the successful login of a user without requiring input from the user. In some embodiments, the user must manually request that the temporary access token be generated, such as by selecting a generate access token button after the successful login of the user. However, a temporary access token may be generated in any other way.

In some embodiments, after a user (e.g., a PSAP administrator or PSAP staff member) successfully logs into the emergency response application 860 and a temporary access token is generated for the user, the user can use the emergency response application to receive emergency data from the clearinghouse, such as through a jurisdictional awareness view (as described below).

Emergency Data Sharing & Jurisdictional Awareness View

Figure 13A:
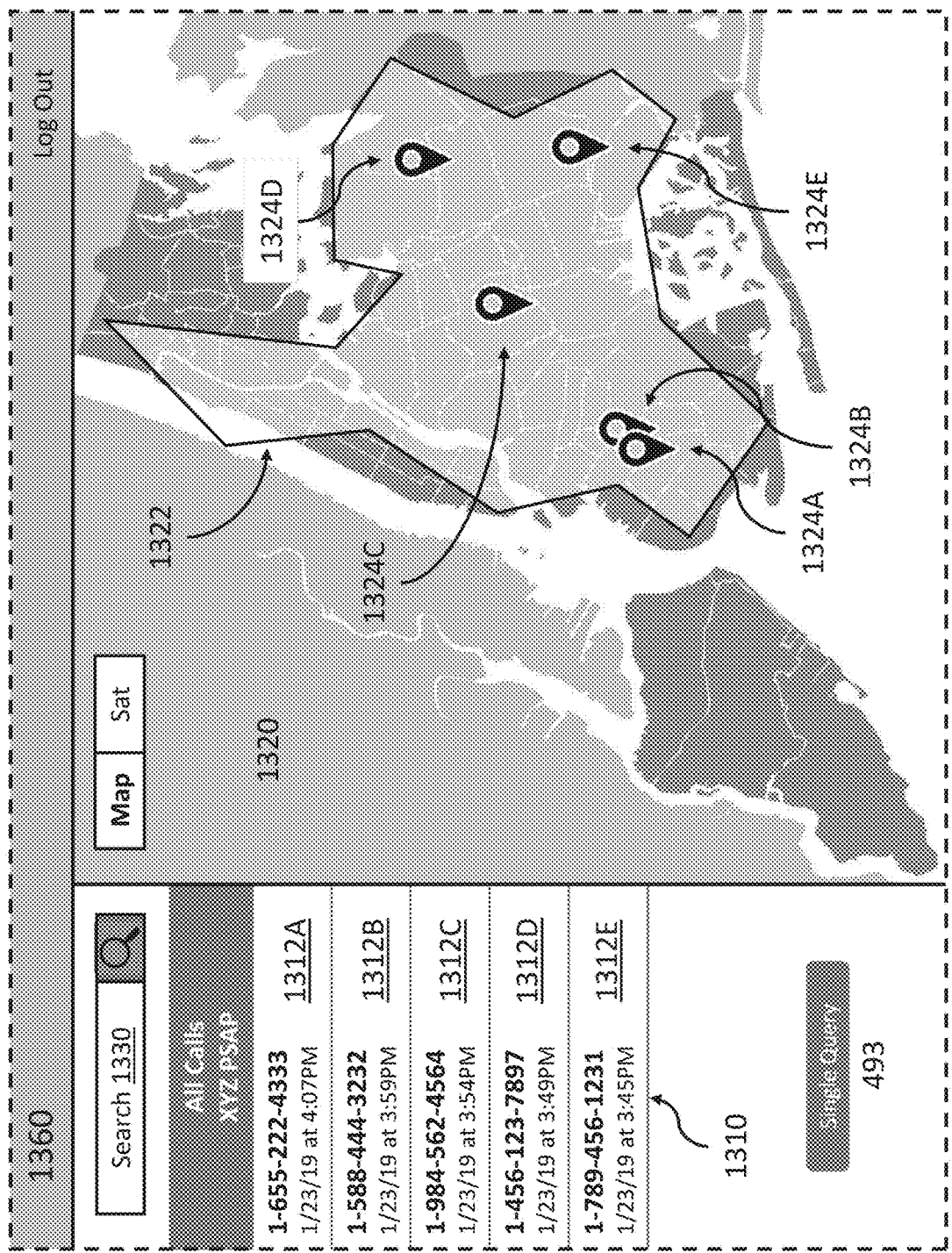
FIG. 13A, FIG. 13B, and FIG. 13C illustrate jurisdictional view of an emergency response application, in accordance with certain embodiments.

As mentioned above, in some embodiments, an emergency management system (EMS) manages the flow emergency data from one or more emergency data sources (e.g., electronic devices or third-party servers) to one or more emergency data recipients (e.g., emergency service providers (ESPs) or other emergency management systems, as described below). In some embodiments, emergency data transmitted to an emergency data recipient is received by and displayed within an emergency response application, as mentioned above. In some embodiments, the systems, applications, servers, devices, methods, and media of the instant application provide a jurisdictional awareness view (also referred to as an "emergency management view") within the emergency response application. In some embodiments, the jurisdictional awareness view enables an ESP to view one or more ongoing or recently generated or received emergency alerts (e.g., emergency calls) within one or more geofenced jurisdictions. FIG. 13A illustrates the jurisdictional awareness view displayed within the emergency response application. In some embodiments, the jurisdictional awareness view includes a list of incidents (e.g., incident queue 1310) that displays one or more incidents associated with one or more device identifiers (e.g., phone numbers, IP addresses). In some embodiments, the jurisdictional awareness view additionally or alternatively includes an interactive map that displays one or more incident locations associated with the one or more incidents associated with the one or more device identifiers, as described below. In some embodiments, the list of incidents 1310 is referred to as an emergency alert queue where emergency calls and/or alternative emergency alerts (e.g., SMS alerts, web-based alerts, emergency alarms, etc.) are displayed. In some embodiments (not shown), emergency alerts are displayed in a first queue and alternative emergency alerts are displayed on a second queue within the emergency response application. The alternative emergency alerts may be primary requests for service that have to be claimed by the ESP user within a specified time period.

Figure 11:
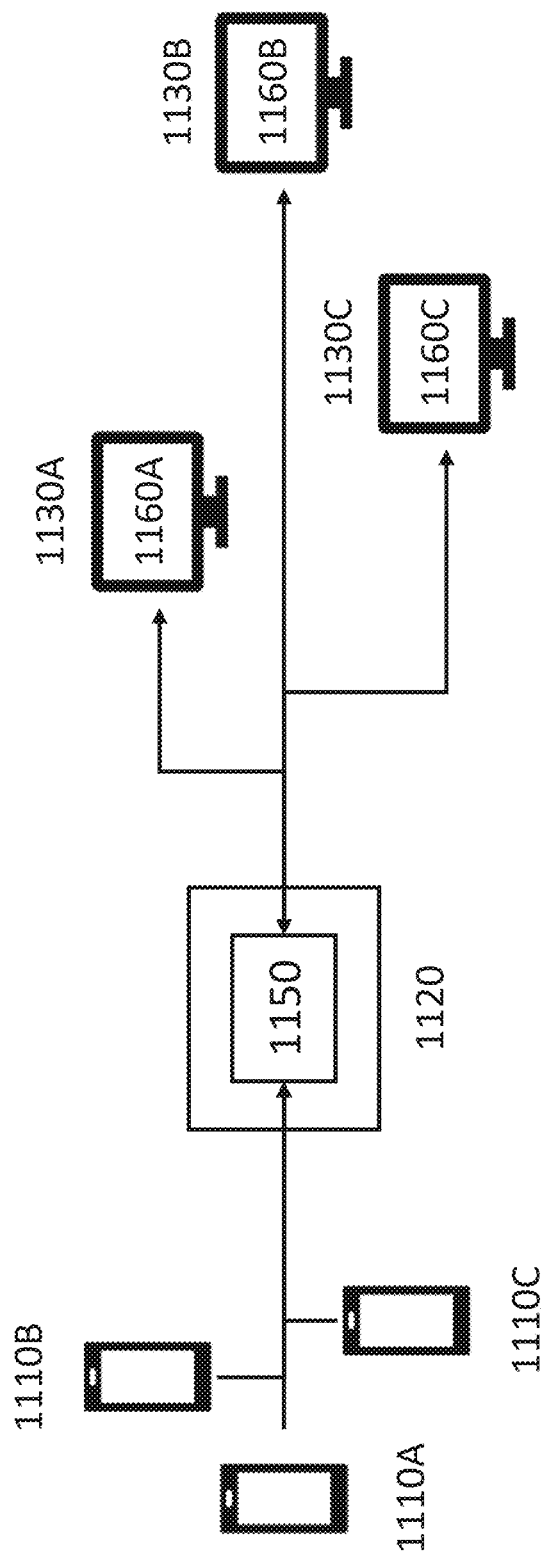
FIG. 11 depicts a flow of emergency data associated with an emergency call, in accordance with certain embodiments.

As described above, in some embodiments, the emergency management system 1120 (EMS) can push emergency data from the Emergency Clearinghouse to emergency service providers (ESPs) using an emergency data subscription system (hereinafter, "subscription system"). FIG. 11 depicts a flow diagram of a process for pushing emergency data from the Emergency Clearinghouse to one or more ESPs. In some embodiments, a member of an ESP (e.g., a PSAP staff member) logs into the emergency response application 1160A at an ESP console 1130A (e.g., a computing device associated with the ESP) by accessing the emergency response application 1160A (e.g., by navigating to the emergency response application 1160A through a web browser) and submitting their login information through the GUI of the emergency response application 1160A. In some embodiments, when the ESP member logs into the emergency response application 1160A by submitting their login information, the emergency response application 1160A or EMS 1120 then determines an ESP account ID associated with the ESP member's account and establishes an active communication link (e.g., a websocket connection) with the ESP console 1130A, thereby automatically subscribing the ESP console to the ESP account ID for the duration of their login session. Then, as described above, when the EMS 1120 receives an emergency alert including a location (e.g., when an emergency call is made from an electronic device 1110A and sends an emergency alert to the EMS 1120 including a location generated by the electronic device 1110A), the EMS 1120 retrieves a geofence associated with every ESP registered with the EMS 1120 and determines if the location falls within any of the geofences. In response to determining that the location falls within a geofence associated with the ESP associated with the ESP account ID, the EMS 1120 then associates the location with the ESP account ID, and determines if there are any active communication links between the EMS 1120 and any computing devices subscribed to the ESP account ID. In this instance, because the ESP console 1130A is subscribed to the ESP account ID and actively linked to the EMS 1120 through the active communication link, the EMS 1120 automatically pushes (e.g., from the clearinghouse 1150) the emergency alert or emergency data associated with the emergency alert (e.g., the location, a phone number, etc.) to the ESP console 1130A for display within the emergency response application 1160A. In some embodiments, emergency alerts or emergency data associated with emergency alerts that have been pushed to an ESP are displayed within the jurisdictional awareness view, as described below.

For example, ESP console 1130A and ESP console 1130B are two different ESP consoles associated with the same ESP (e.g., two computing devices at the same public safety answering point (PSAP)), PSAP A. ESP console 1130C is associated with a second ESP, PSAP B. One day, PSAP call-takers access and successfully log into the emergency response application 1160 (emergency response application 1160A-1160C) at each of the three ESP consoles (ESP console 1130A-1130C), thereby establishing three separate active communication links, one active communication link between the EMS 1120 and each of the three ESP consoles. The ESP consoles are automatically subscribed by the EMS 1120 to the ESP account IDs associated with their respective ESPs (ESP ID A for PSAP A and ESP ID B for PSAP B). Both PSAP A and PSAP B are associated with only one geofence, geofence A and geofence B, respectively. Geofences A and B do not overlap. The geofences have previously been tagged within the EMS 1120 with their respective ESP account IDs (e.g., during the registration process for the emergency response application, as described above).

Later that day, an emergency call is made from communication device 1110A, which causes communication device 1110A to generate a first emergency alert including a first location of the communication device 1110A and transmit the first emergency alert to the EMS 1120. When the EMS 1120 receives the first emergency alert, the EMS 1120 retrieves some or all of the geofences stored within the EMS 1120 and determines if the first location falls within any of the geofences stored within the EMS 1120. In this example, the EMS 1120 determines that the first location falls within geofence A, associated with PSAP A. In response, the EMS 1120 tags the first location with the ESP account ID associated with geofence A, ESP ID A. The EMS 1120 then determines if there are any active or persistent communication links between the EMS and any ESP consoles subscribed to ESP ID A and automatically pushes (e.g., from the clearinghouse 1150) the first emergency alert to those ESP consoles. In this example, both ESP console 1130A and ESP console 1130B are subscribed to ESP ID A, so the EMS 1120 automatically pushes the first emergency alert to both ESP console 1130A and ESP console 1130B for display within emergency response applications 1160A and 1160B, respectively, such as through a jurisdictional awareness view (as described below). The first location does not fall within geofence B, because geofence A and geofence B do not overlap, so the first emergency alert is not pushed to ESP console 1130C, even though an active communication link has been established between the EMS 1120 and ESP console 1130C.

Three minutes later, an emergency call is made from communication device 1110B, which causes communication device 1110B to generate a second emergency alert including a second location of the communication device 1110B and transmit the second emergency alert to the EMS 1120. When the EMS 1120 receives the second emergency alert, the EMS again retrieves some or all of the geofences stored within the EMS 1120 and determines if the second location falls within any of the geofences stored within the EMS 1120. In this example, the EMS 1120 determines that the second location falls within geofence B, associated with PSAP B. In response, the EMS 1120 tags the second location within the ESP account associated with geofence B, ESP ID B and automatically pushes the second emergency alert to ESP console 1130C for display within emergency response application 1160C, because ESP console 1130C has an active communication link established with the EMS 1120 and ESP console 1130C is subscribed to ESP ID B. The EMS 1120 does not push the second emergency alert to ESP console 1130A or ESP console 1130B. Although ESP console 1130A and ESP console 1130B have active communication links established with the EMS 1120, they are not subscribed to ESP ID B, and geofence A and geofence B do not overlap, meaning the second location does not fall within geofence A. Two minutes after that, an emergency call is made from communication device 1110C, which then generates a third emergency alert including a third location of the communication device 1110C and transmits the third emergency alert to the EMS 1120. The EMS 1120 determines that the third locations falls within geofence A (like the first location included in the first emergency alert) and thus automatically pushes the third emergency alert to both ESP console 1130A and ESP console 1130B for display within emergency response applications 1160A and 1160B. In some embodiments, emergency response application 1160A and emergency response application 1160B display the first emergency alert and the third emergency alert simultaneously, such as through a jurisdictional awareness view, as described below.

Third-Party Queries

In some embodiments, emergency data may be accessed from third-party servers on a need-to-know basis. On one hand, availability of emergency data (such as location data, user data, sensor data) can improve the emergency response. However, for private data (such as user location, medical data, etc.), it may critical to maintain privacy and integrity of the emergency data.

Various types of access controls are contemplated for differential access to emergency data. In some embodiments, privacy controls based on user preferences and/or consent may be applied to the emergency data. For example, a user may indicate that his or her medical data be accessible only during a medical emergency to medical personnel. In this case, the type of emergency has to be determined before the medical data can be pulled from the third-party database.

Thus, the emergency data may be "pulled" from third-party servers only when there is a known receiving party. For example, an ESP user (such as a PSAP call taker) may have sent a data request for a particular device identifier (e.g., a phone number). Alternatively, an ESP user (such as a PSAP call taker) may have logged in to an emergency response application and emergency alerts within the jurisdiction of the ESP can be displayed for efficient emergency response as described below.

Figure 12:
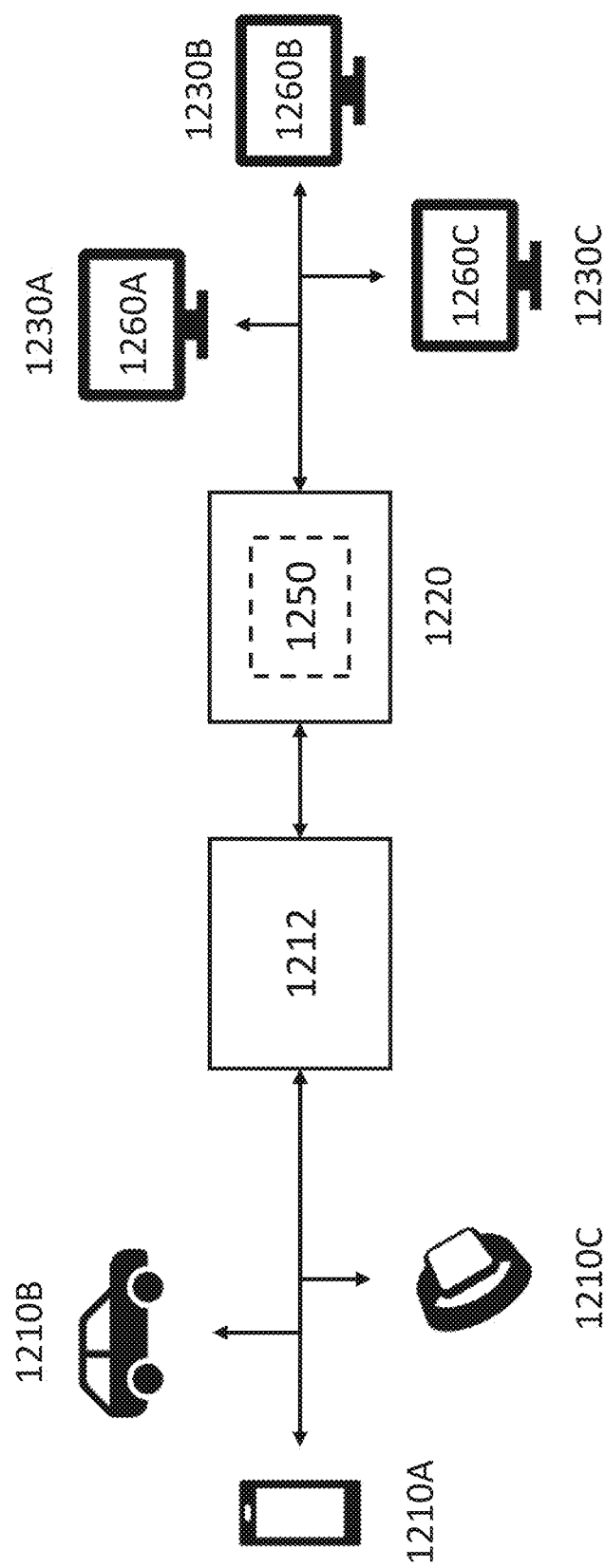
FIG. 12 illustrates embodiments of a system for receiving and transmitting emergency data by an emergency management system (EMS).

FIG. 12 depicts a diagram of a system for receiving and transmitting emergency data by an emergency management system (EMS). As depicted by FIG. 12, in some embodiments, the system includes one or more electronic device 1210, a third-party server 1212, an EMS 1220, and one or more emergency service providers (ESPs) 1230. In some embodiments, the EMS 1220 includes a clearinghouse 1250 for emergency data, as described above. In some embodiments, an ESP 1230 includes an emergency response application 1260, as described above. In some embodiments, as depicted by FIG. 12, the third-party server 1212 is communicatively coupled to one or more electronic device 1210. In some embodiments, the one or more electronic devices 1210 communicatively coupled to the third-party server 1212 are all the same type of device. For example, in some embodiments, the third-party server 1212 is the backend system of a ridesharing company (e.g., Uber or Lyft), and the one or more electronic devices 1210 are all mobile phones 1210A powering a ridesharing application (e.g., the Uber or Lyft app). In some embodiments, the one or more electronic devices 1210 communicatively coupled to the third-party server 1212 are different types of devices. For example, in some embodiments, the third-party server 1212 is the backend system of a device manufacturer (e.g., Apple), and the one or more electronic devices 1210 communicatively coupled to the third-party server 1212 include mobile phones 1210A, smartwatches 1210C, laptop computers, and the like. In some embodiments, as depicted by FIG. 12, the third-party server 1212 is also communicatively coupled to the EMS 1220. As depicted by FIG. 12, in some embodiments, the EMS 1220 is communicatively coupled to a plurality of ESPs 1230, such as ESPs 1230A-1230C. Although only one third-party server 1212 is shown in FIG. 12, it will be appreciated that the EMS 1220 may be communicatively coupled to a plurality of third-party servers 1212.

In some embodiments, as described above with respect to FIG. 11, an emergency data source can autonomously or automatically transmit (i.e., "push") an emergency alert or emergency data to an EMS (e.g., without first receiving a query from the EMS). However, as mentioned above, in some embodiments, the EMS 1220 can query emergency data sources (e.g., a third-party server 1212) for emergency data (i.e., the EMS 1220 can "pull" emergency data from emergency data sources) instead. For example, in some embodiments, when an ESP 1230 establishes an active communication link (e.g., a persistent communication link, such as a websocket connection) with the EMS 1220, such as by logging into an emergency response application 1260, as described above, the EMS 1220 can immediately transmit a query (hereinafter, a "third-party query") including an identifier of the ESP to a third-party server 1212. The third-party server 1212 can then retrieve any emergency data tagged with the identifier of the ESP that is stored within the third-party server 1712 system or otherwise accessible by the third-party server 1212 and return the emergency data tagged with the identifier of the ESP to the EMS 1220, so that the EMS 1220 may then in turn autonomously and automatically transmit (e.g., push, as described above) the emergency data tagged with the identifier of the ESP to the ESP 1230, such as through the active communication link. In some embodiments, an emergency data source (e.g., a third-party server 1212) does not transmit emergency data to the EMS 1220 unless the emergency data source first receives a third-party query including an identifier of an ESP from the EMS 1220 (i.e., the EMS 1220 must pull emergency data from the emergency data source), and the EMS 1220 does not transmit a third-party query including an identifier of an ESP to the emergency data source (e.g., the third-party server 1212) unless there is an active communication link previously established between the EMS and the ESP. Requiring the EMS 1220 to pull emergency data from the emergency data source (e.g., the third-party server 1212), and only when an appropriate recipient of the emergency data is already present, provides further security and protection to the emergency data. When a third-party server 1212 pushes emergency data to the EMS 1220 without knowing if an appropriate recipient is already present, the third-party server 1212 risks transmitting emergency data that may never be received by an appropriate recipient, thereby needlessly putting the emergency data at risk. The emergency data returned by a third-party server 1212 may include any type of emergency data, including, but not limited to: location data, user data, demographic data, medical data, ride data, or health data. The emergency data tagged with the identifier of the ESP may then be displayed within an emergency response application 1260, such as within a jurisdictional awareness view, as described above. In some embodiments, the EMS 1220 can continue to periodically transmit a third-party query including the identifier of the ESP to the third-party server 1212 to receive new or updated emergency data tagged with the identifier of the ESP. For example, in some embodiments, after an ESP establishes an active communication link with the EMS 1220, the EMS 1220 periodically transmits third-party queries including the identifier of the ESP to the third-party server 1212 at an interval of 1 second, 2 seconds, 3 seconds, 4 seconds, 5 seconds, 10 seconds, or 15 seconds. In this way, the emergency data can be updated at different intervals. However, the EMS 1220 may periodically transmit third-party queries to a third-party server 1212 at any interval of time. In some embodiments, the EMS 1220 periodically transmits third-party queries including an identifier of an ESP to a third-party server 1212 throughout the duration of an active communication link established between the ESP 1230 and the EMS 1220.

For example, in some embodiments, when a person dials 911 from their mobile phone, the mobile phone generates and transmits an emergency alert, including a device-based hybrid location generated in real-time by the mobile phone, to a third-party server 1212. The emergency alert may include emergency data associated with the emergency alert, such as the location, a device or user identifier, or a timestamp. In this example, the third-party server 1212 is able to access (e.g., internally or externally) one or more geofences associated with one or more respective emergency service providers (ESPs) and determine if the location (i.e., the device-based hybrid location generated by the mobile phone) falls within any of the one or more geofences. If the third-party server 1212 determines that the location does fall within one of the one or more geofences, the third-party server 1212 tags the emergency alert or the emergency data included in the emergency alert (e.g., the location) with an identifier of the particular ESP associated with that geofence, and stores the emergency alert or the emergency data included in the emergency alert in one or more of the third-party server's databases. Then, if the EMS 1220 detects an active communication link established between the EMS 1220 and the particular ESP, the EMS 1220 transmits a third-party query including the identifier of the particular ESP to the third-party server 1212. In turn, the third-party server 1212 then retrieves and transmits the emergency alert or the emergency data included in the emergency alert that has been tagged with the identifier of the particular ESP to the EMS 1220 for autonomous and automatic transmission to the particular ESP (such as through the active communication link). In this example, the EMS 1220 can then periodically (e.g., every second or every five seconds) transmit subsequent third-party queries including the identifier of the particular ESP to the third-party server 1212. In some embodiments, the EMS 1220 periodically transmits subsequent third-party queries including the identifier of the particular ESP to the third-party server 1212 for the duration of the active communication link established between the particular ESP and the EMS 1220.

In some embodiments, when there are active communication links established between the EMS 1220 and multiple ESPs, as depicted in FIG. 12, the EMS 1220 can transmit a single third-party query including all of the identifiers of the multiple ESPs to a third-party server 1212. In some embodiments, the EMS 1220 transmits multiple, separate third-party queries, each including only a single identifier of a single ESP. In some embodiments, when a third-party server 1212 receives multiple emergency alerts including respective emergency locations that fall within the same particular geofence, the multiple emergency alerts (or the emergency data included in the multiple emergency alerts) are thus tagged with an identifier of the same ESP associated with that particular geofence. Then, if the EMS 1220 transmits a third-party query including the identifier of that ESP to the third-party server 1212, the third-party server 1212 will return each of the multiple emergency alerts (or the emergency data included in each of the multiple emergency alerts) tagged with the identifier of the ESP to the EMS 1220 for transmission to the ESP. In this way, the EMS 1220 effectively requests all of the emergency alerts or associated emergency data relevant to a particular jurisdiction or geofence when the EMS 1220 transmits a third-party query including an identifier of an ESP, because the identifier of the ESP is associated with a geofence (i.e., a geographical area) and not a particular person or emergency event. This is in contrast to queries including other types of identifiers, such as a user or device identifier, to which a third-party server 1212 may return an emergency alert or emergency data relevant only to one person or emergency event. In some embodiments, an emergency alert or emergency data received by a third-party server 1212 (and, in some embodiments, subsequently tagged with an identifier of an ESP) is deleted, purged, or expires after a predetermined amount of time, so that the third-party server 1212 may only return relatively recent emergency data in response to a third-party query from an EMS. For example, in some embodiments, an emergency alert or emergency data received by a third-party server 1212 may be deleted or purged after thirty minutes or an hour expires from the time that the emergency alert or emergency data was received. Periodically purging emergency data received by a third-party server 1212 also limits the exposure of potentially sensitive data.

However, in some embodiments, the EMS 1220 may also transmit a third-party query including different types of identifiers to a third-party server 1212, such as a user identifier (e.g., an email address) or a device identifier (e.g., a phone number), so that the third-party server 1212 may retrieve and transmit emergency data associated or tagged with different types of identifiers to the EMS 1220. For example, in some embodiments, if the EMS 1220 receives an emergency alert associated with a device identifier (e.g., a phone number) from an electronic device (directly or indirectly, such as through a third-party server, as described above), the EMS 1220 can transmit a third-party query including the device identifier to one or more third-party servers 1212 (which may or may not include a third-party server from which the emergency alert was received) to request any available additional emergency data associated with the device identifier. The emergency data returned by a third-party server 1212 may include any type of emergency data, including, but not limited to: location data, user data, demographic data, medical data, or health data. For example, a solo skier in Colorado inadvertently crashes into a tree, severely injuring their leg. Fortunately, the skier is able to access their mobile phone and dial 911, which also prompts the mobile phone to generate and transmit an emergency alert including a device-based hybrid location generated in real-time by the mobile phone to the EMS 1220. The skier's location falls within a geofence associated with a Colorado PSAP that has previously established an active communication link with the EMS 1220. In this example, the EMS 1220 tags the emergency alert (and all of the emergency data included in the emergency alert; e.g., the skier's location) with an identifier of the Colorado PSAP and automatically transmits (i.e., pushes, as described above) the emergency data included in emergency alert to the Colorado PSAP through the active communication link established between the EMS 1220 and the Colorado PSAP. In this example, the EMS 1220 also transmits a third-party query including the skier's phone number (included in the emergency alert) to a plurality of third-party servers 1212 communicatively connected to the EMS 1220 and receives emergency data associated with the skier's phone number from two different third-party servers 1212. First, from the backend system of a device manufacturer that produced a smartwatch that the skier is wearing, the EMS 1212 receives real-time heartrate data generated by a sensor on the smartwatch. Second, from a database of medical information that the skier has registered on, the EMS 1212 receives a medical profile of the skier. The EMS 1212 then automatically transmits the heartrate data and medical profile to the Colorado PSAP. The Colorado PSAP can then use all of the emergency data associated with the emergency alert (e.g., the skier's location, the skier's heartrate data, and the skier's medical profile) to more quickly and effectively respond to the skier's emergency. In this example, the EMS 1220 can periodically (e.g., every 5 seconds) transmit subsequent third-party queries including the skier's phone number to the device manufacturer for updates of the skier's heartrate data, which the EMS 1220 can then transmit to the Colorado PSAP.

In some embodiments, the EMS 1220 may send different types of third-party queries to a third-party server 1212. For example, in some embodiments, the EMS 1220 can send a third-party query for location data or a third-party query for additional data. In some embodiments, the EMS 1220 can send different types of third-party queries for additional data. For example, the EMS 1220 may send a third-party query for medical data, or a third-party query for sensor data, or a third-party query for user data. In some embodiments, the type of emergency data is included within the third-party query such as within the routing code, header, or a separate data field In some embodiments, the third-party query for different data types will be sent to different third-party server endpoints. In some embodiments, the returned data will be marked with the data type so differential access by ESP users may be implemented.

It is contemplated that different types of data may need to be updated at different frequencies. For example, some data such as user name and address may be static, while location and sensor data may be dynamic. In some embodiments, different types of third-party queries are periodically transmitted by the EMS 1220 to a third-party server at different intervals. For example, in some embodiments, the EMS 1220 periodically transmits third-party queries for additional data less frequently (e.g., every 15 seconds) than the EMS 1220 periodically transmits third-party queries for location data (e.g., every 5 seconds).

In some embodiments, user of third-party queries with data types can allow access controls and differential access to emergency data. In some cases, a determination of the type of emergency may be required to be done before certain types of emergency data is accessed (e.g., medical data will be available for medical emergencies). For access controls, user consent or preferences or third-party data policies may be followed by restricting access to private data for certain types of emergencies (e.g., medical emergencies). For differential access, user consent or preferences or third-party data policies may be followed by restricting access to the type of ESP (e.g., a user may not give permission to share location data for police emergencies). In the processes depicted by FIGS. 11 & 12, the EMS, using the subscription model, does not require receiving an emergency data request to determine an appropriate ESP to receive an emergency alert or emergency data associated with the emergency alert. As a result, the EMS can use the jurisdictional awareness view within the emergency response application to display emergency alerts and emergency data associated with emergency alerts to appropriate ESPs as the emergency alerts are received by the EMS in real-time. Using the subscription system to automatically push emergency data from the clearinghouse to ESPs provides numerous advantages. The system allows members of an ESP to see and be aware of all emergencies in their jurisdiction whether or not they are handling or responding to a particular emergency and whether or not an emergency call actually gets connected to the ESP. Additionally, even if a member of the ESP is not immediately able to respond to an emergency alert, they are still able to see where the emergency is and when the emergency alert was received. As depicted by FIG. 13A, in some embodiments, the jurisdictional awareness view includes an incident queue 1310 (also referred to as a "list of incidents") and an interactive map 1320. In some embodiments, when an emergency alert or emergency data associated with the emergency alert is pushed to the emergency response application, an incident 1312 is created for the emergency alert and displayed within the incident queue 1310. In some embodiments, as depicted by FIG. 13A, an incident 1312 created for an emergency alert is displayed with a device identifier associated with the emergency alert. For example, FIG. 13A depicts five incidents 1312 associated with five different emergency alerts, 1312A-1312E. Incident 1312A is displayed with the device identifier "1-655-222-4333" representing the electronic device that generated the emergency alert that incident 1312A was created for. It is contemplated that incidents within the incident queue 1310 may be displayed or ordered in any manner for clarity and efficiency. In some embodiments, the incident queue 1310 is ordered sequentially based on the time that the emergency alerts are received by the emergency response application. In some embodiments, the incident queue 1310 is prioritized based on type of emergency, severity of the emergency or other appropriate factors. In some embodiments, the ESP user is required to respond to emergency alerts in the alert queue sequentially. In some embodiments, the ESP user may select or respond to any emergency alert in the queue in any order.

In some embodiments, the incident queue 1310 is populated by device identifiers that correspond to emergency locations. In some embodiments, the incident queue 1310 displays a call start time associated with each device identifier. In some embodiments, the incident queue 1310 displays a call end time associated with each device identifier. In some embodiments, the incident queue 1310 displays a call date associated with each device identifier. In some embodiments, the incident queue 1310 displays a call start time, end time, and date associated with each device identifier in the user's time zone or in the caller's time zone. In some embodiments, the incident queue 1310 displays a call start time, end time, and date associated with each device identifier in the user's time zone and in the caller's time zone. In some embodiments, the incident queue 1310 is ordered. In some embodiments, the incident 1310 queue is ordered with respect to the start time of the call. In some embodiments, the terminated calls are automatically removed from the incident queue 1310 by the user. In some embodiments, the terminated calls are automatically removed from the incident queue 1310. In some embodiments, the terminated calls are automatically removed from the incident queue 1310 after a variable delay. In some embodiments, the terminated calls are automatically removed from the incident queue 1310 after a variable delay if the user does not manually remove the terminated call. In some embodiments, the delay is about 5 seconds, about 10 seconds, about 15 seconds, about 20 seconds, about 30 seconds, about 45 seconds, about 60 seconds, about 2 mins, about 5 mins, about 10 mins, about 15 mins, about 30 mins, about 45 mins, about 60 mins, about 2 hours, about 5 hours, about 8 hours, or about 12 hours.

In some embodiments, the incident queue 1310 includes a search box 1330 that allows the user to quickly find device incidents within the incident queue 1310 by their associated device identifiers. In some embodiments, the search box 1330 allows for searching in a current incident queue. In some embodiments, the search box 1330 allows for searching through historical incidents. In some embodiments, the search box 1330 allows for searching in a current incident queue and historical incidents. In some embodiments, a historical incident is an incident terminated or resolved anytime in the previous 5 mins, 30 mins, 60 mins, 3 hours, 6 hours, 12 hours, or 24 hours. In some embodiments, a historical incident is an incident terminated or resolved at a previous time. In this respect, a user is able to review the history of a device identifier with respect to previously emergency alerts (e.g., emergency calls). For example, a search for the device identifier "1-655-222-4333" may return incident 1312A, a current incident that is currently displayed within the incident queue 1310, as well as one or more historical incidents associated with previous emergency alerts associated with the device identifier.

As mentioned above, in some embodiments, the jurisdictional awareness view includes an interactive map 1320. In some embodiments, the jurisdictional awareness view displays one or more geofences 1322 associated with the ESP for which the emergency response application has been accessed. In some embodiments, the jurisdictional awareness view displays one or more incident locations 1324 (e.g., a location marker) for each incident 1312 listed in the incident queue 1310 within the interactive map 1320. For example, FIG. 13A depicts five incident locations 1324 within the interactive map 1320, incident locations 1324A-1324E, one for each of the five incidents 1312 listed in the incident queue 1310, incidents 1312A-1312E, respectively. In some embodiments, the jurisdictional awareness view displays at least one incident location 1324 for each incident 1312 listed in the incident queue 1310. In some embodiments, the jurisdictional awareness view displays only one incident location 1324 for each incident 1312 listed in the incident queue 1310. In some embodiments, each incident location 1324 is customizable by the user. In some embodiments, the shape and/or color of each incident location 1324 is customizable. In some embodiments, the shape and color of the incident location 1324 is denoted in the incident queue 1310. In some embodiments, the user is enabled to annotate text next to or within a text box associated with a particular incident location 1324. In some embodiments, the user is enabled to annotate text next to or below each device identifier within the incident queue 1310. For example, a user may customize three incident locations 1324 currently displayed within the interactive map 1329 by changing the incident locations 1324 to a "yellow star", and the associated incidents 1312 in the incident queue 1310 are automatically denoted with a "yellow star" adjacent to their respective device identifiers.

Figure 13B:
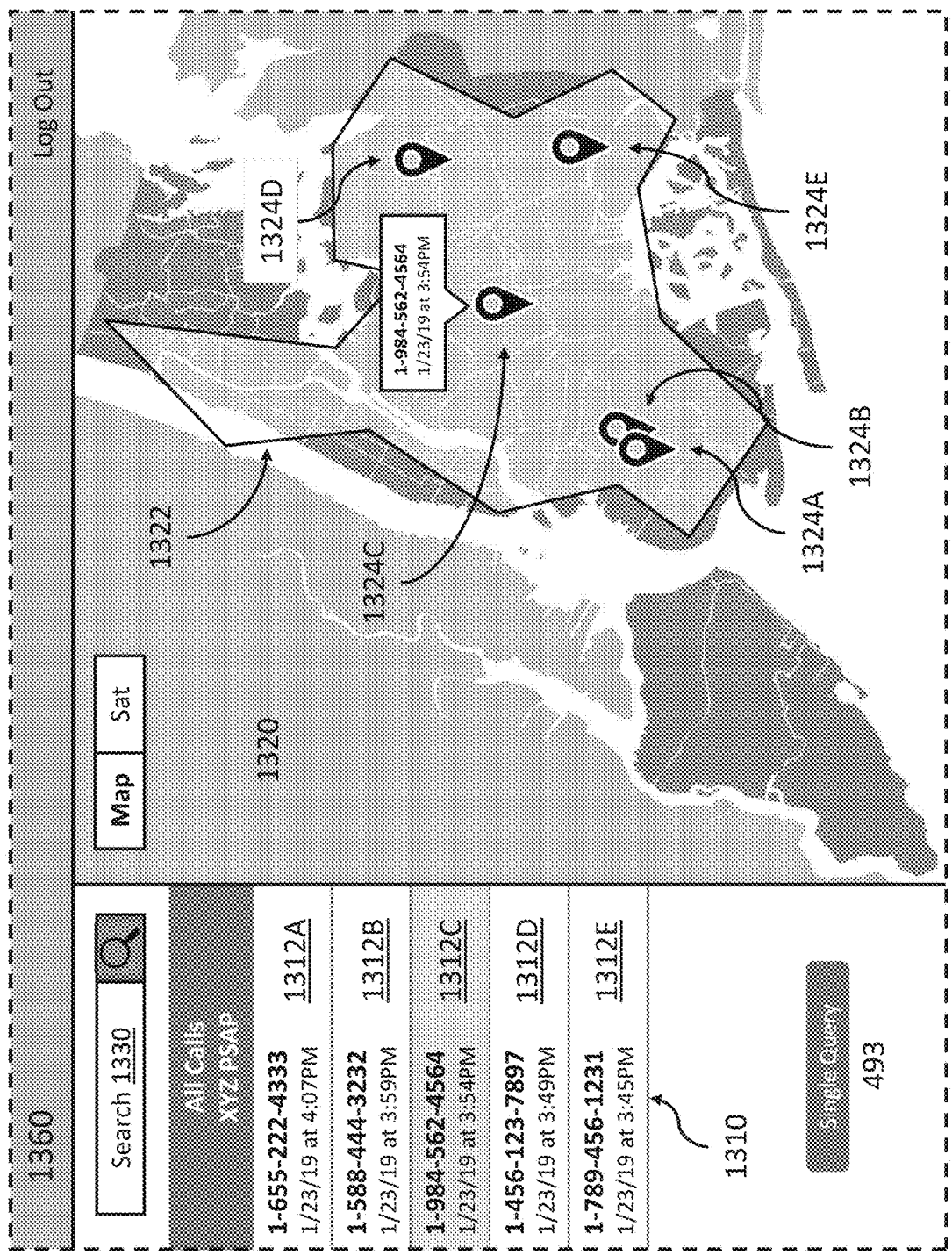

In some embodiments, each incident location 1324 is automatically updated or changed. In some embodiments, the incident location 1324 is updated or changed to reflect response status of secondary response agencies, such as the fire department or police department. In some embodiments, the incident location 1324 is updated or changed to reflect response status at a PSAP. For example, the incident location 1324 may be flashing to indicate that no user at the PSAP has attended to the associated incident 1312. In another example, the incident location 1324 may automatically change color to indicate that a first responder has been dispatched to the associated emergency location. In another example, an incident location 1324 may automatically change to reflect that an emergency is no longer active, or the caller has exited the jurisdictional geofence of the PSAP. In some embodiments, the user is enabled to toggle on and off incident location customization preferences. In some embodiments, the user is enabled to display device identifier data (e.g. phone numbers) adjacent to an incident location 1324. For example, as depicted in FIG. 13B, an additional data overlay associated with incident 1312C (e.g., the associated device identifier and the time and date that the associated emergency alert was received) is displayed directly above the incident location 1324C associated with incident 1312C. In some embodiments, data associated with an incident is displayed within the interactive map 1320 in response to the incident 1312 or associated incident location 1324 being selected within the incident queue 1310 or interactive map 1320. In some embodiments, a user can select an incident 1312 or an incident location 1324 by clicking on or hovering over the incident 1312 or incident location 1324.

The jurisdictional view may allow an ESP user (e.g., a PSAP call taker) to mark one or more incidents as "Cancel", "Duplicate", "Push to CAD", etc. For example, a PSAP call taker can cancel inadvertent calls (e.g., butt dials), prank calls, and other non-emergency calls. For example, a fire that is being reported in two incidents 1312A and 1312B may be reporting the same fire. The ESP user (e.g., PSAP call taker, supervisor, emergency responder) may mark one of these incidents as a duplicate. In some embodiments, the ESP user links the two incidents 1312A and 1312B as related. In some embodiments, the ESP user consolidates the two incidents 1312A and 1312B as the same incident. By allowing identification of redundant emergency alerts, the jurisdictional view improves efficiency and efficacy of the emergency response.

In addition, a PSAP call taker could initiate a CAD (e.g., a computer aided dispatch (CAD) software program included in preexisting PSAP software) incident based on an incident 1312 listed in the incident queue 1310. For example, an emergency alert may have been triggered by smoke alarms in a home and there may not be an associated emergency call. By creating a CAD incident, the PSAP call taker could initiate dispatch and emergency response for to the home. In such an embodiment, the emergency response application can communicate with the CAD program to push an incident 1312 listed in the incident queue 1310 to the CAD program where the CAD program can then create a CAD incident for the incident 1312.

In some embodiments, the user initiates the emergency response application to find the jurisdictional awareness view, which displays one or more geofences associated with the user's ESP within an interactive map 1320. In some embodiments, the jurisdictional awareness view is populated with previous and current incidents associated with emergency alerts being attended to by the ESP. In some embodiments, upon initiation of the emergency response application, the jurisdictional awareness view is not populated with previous and current incidents, but becomes populated with each incoming emergency alert following the initiation of the emergency response application. In some embodiments, as mentioned above, when an incident 1312 is added to the incident queue 1310, a corresponding incident location 1324 is added to the interactive map 1320. In some embodiments, when an incident 1312 is removed from the incident queue 1310 (e.g., if the incident is resolved, marked as a duplicate, or otherwise deleted), the corresponding incident location 1324 is removed from the interactive map 1320. In some embodiments, wherein the user hovers or selects the incident location 1324, the device identifier (e.g., phone number) associated with the corresponding incident 1312 is displayed adjacent to the incident location 1324. FIG. 13B illustrates the selection of an incident 1312C in the incident queue 1310, which is then displayed at the corresponding incident location 1324C. In some embodiments, multiple incidents 1312 can be selected in the incident queue 1310 to display information adjacent to the corresponding incident location 1324.

In some embodiments, wherein a device that generated an emergency alert for which an incident is created within the jurisdictional awareness view is a mobile device and relocating in real time, the device's location is updated within the interactive map of the jurisdictional awareness view in real time. For example, when the emergency alert (including an initial location) is generated and transmitted to (or detected by) the emergency management system (EMS), the EMS can determine an appropriate ESP to receive the emergency alert and any data associated with the emergency alert and then automatically push the emergency alert and any data associated with the emergency alert to the ESP through the jurisdictional awareness view of the emergency response application (as described above). The emergency response application can then create an incident associated with the emergency alert within the jurisdictional awareness view, such as by listing an incident 1312 in the incident queue 1310 and displaying a corresponding incident location 1324 within the interactive map 1320. If the device sends updated location to the EMS, the EMS can automatically push the updated location to the emergency response application. The emergency response application can then update the incident location 1324 by moving the incident location 1324 within the interactive map 1320 to the location of the updated location received from the device. In some embodiments, the emergency response application displays the location associated with all incidents 1312 listed in the incident queue 1310 and tracks the location associated with each incident 1312 in real time simultaneously.

Figure 13C:
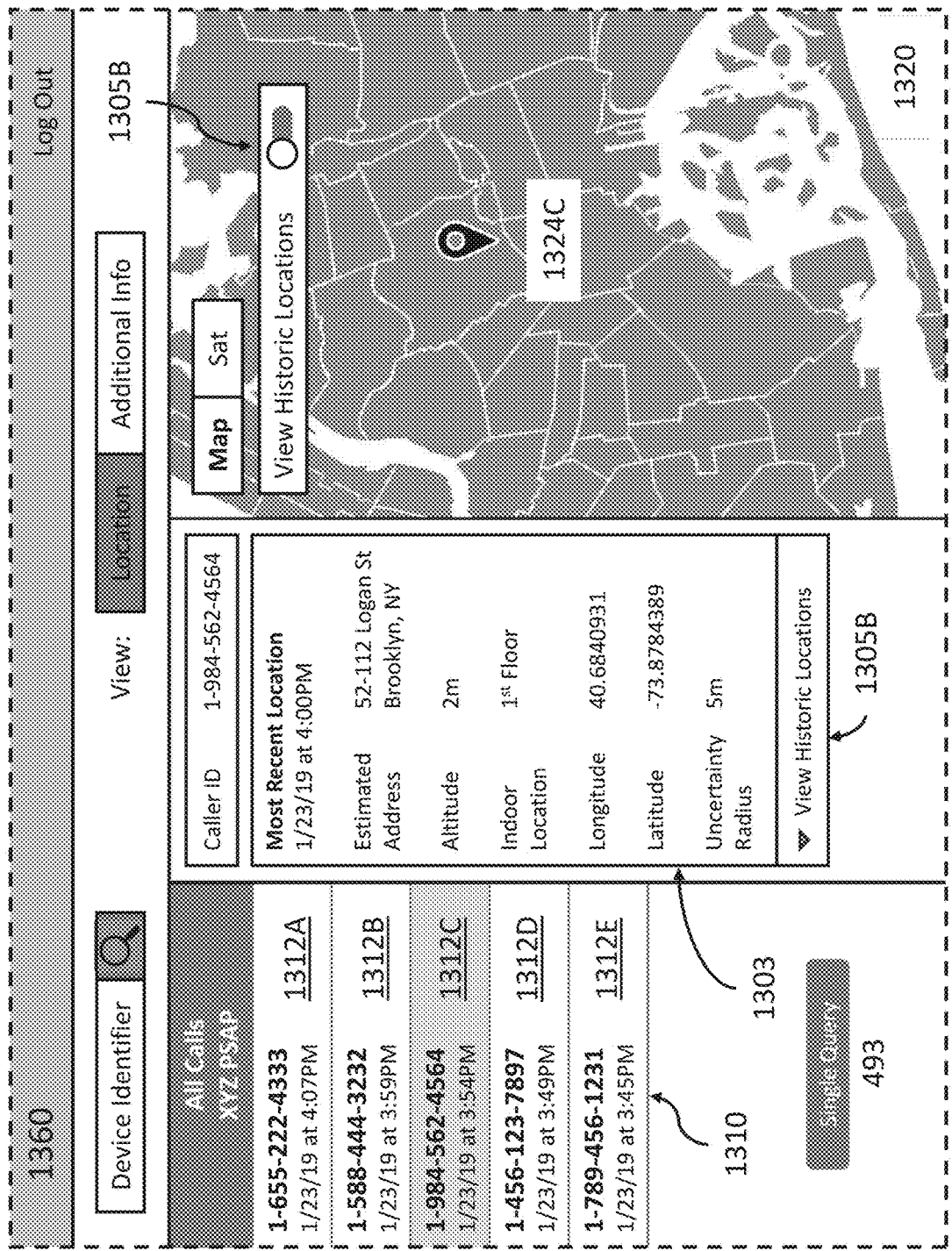
Figure 14A:
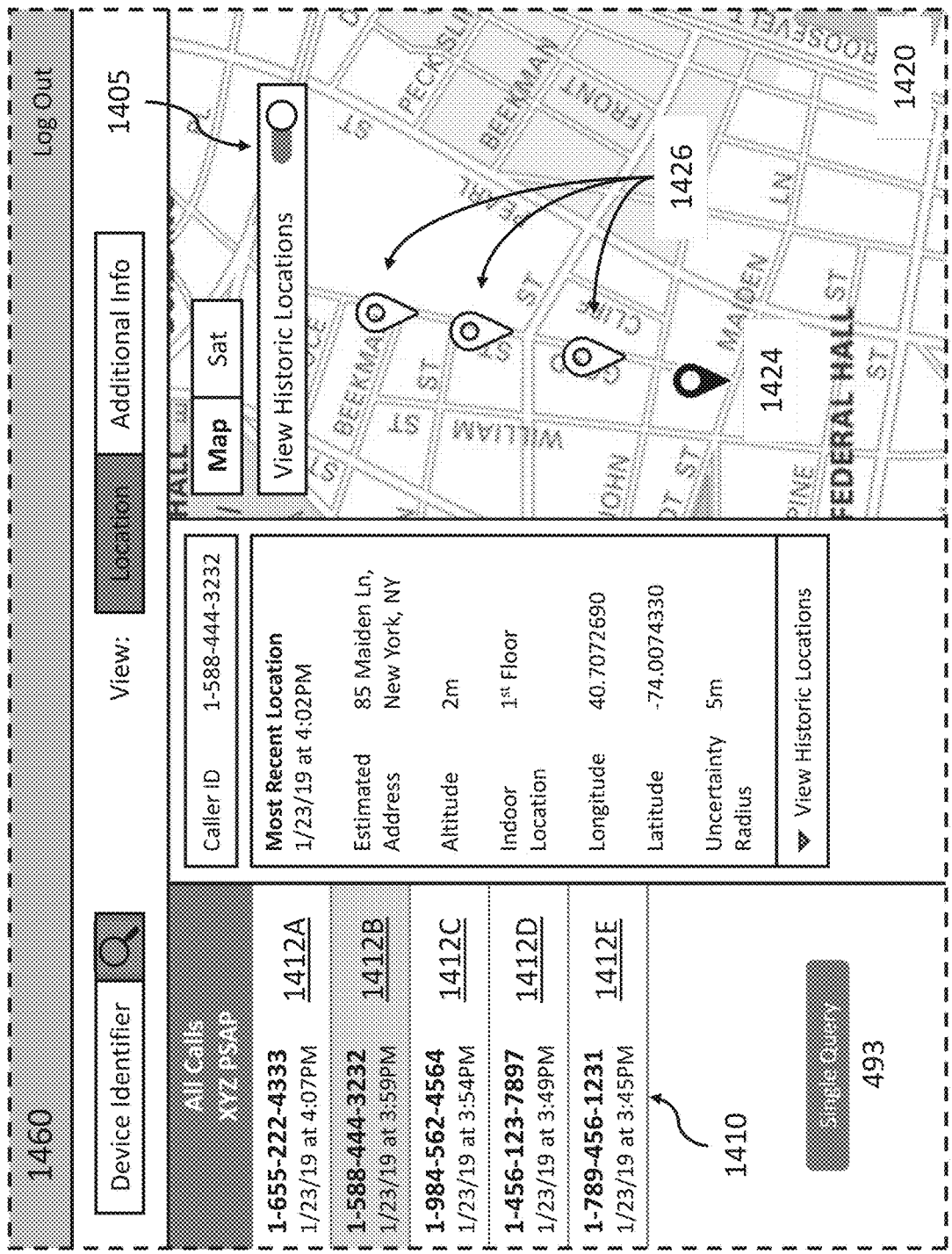
FIG. 14A, FIG. 14B, and FIG. 14C illustrate features of jurisdictional awareness view displayed within the emergency response application, in accordance with certain embodiments.
Figure 14B:
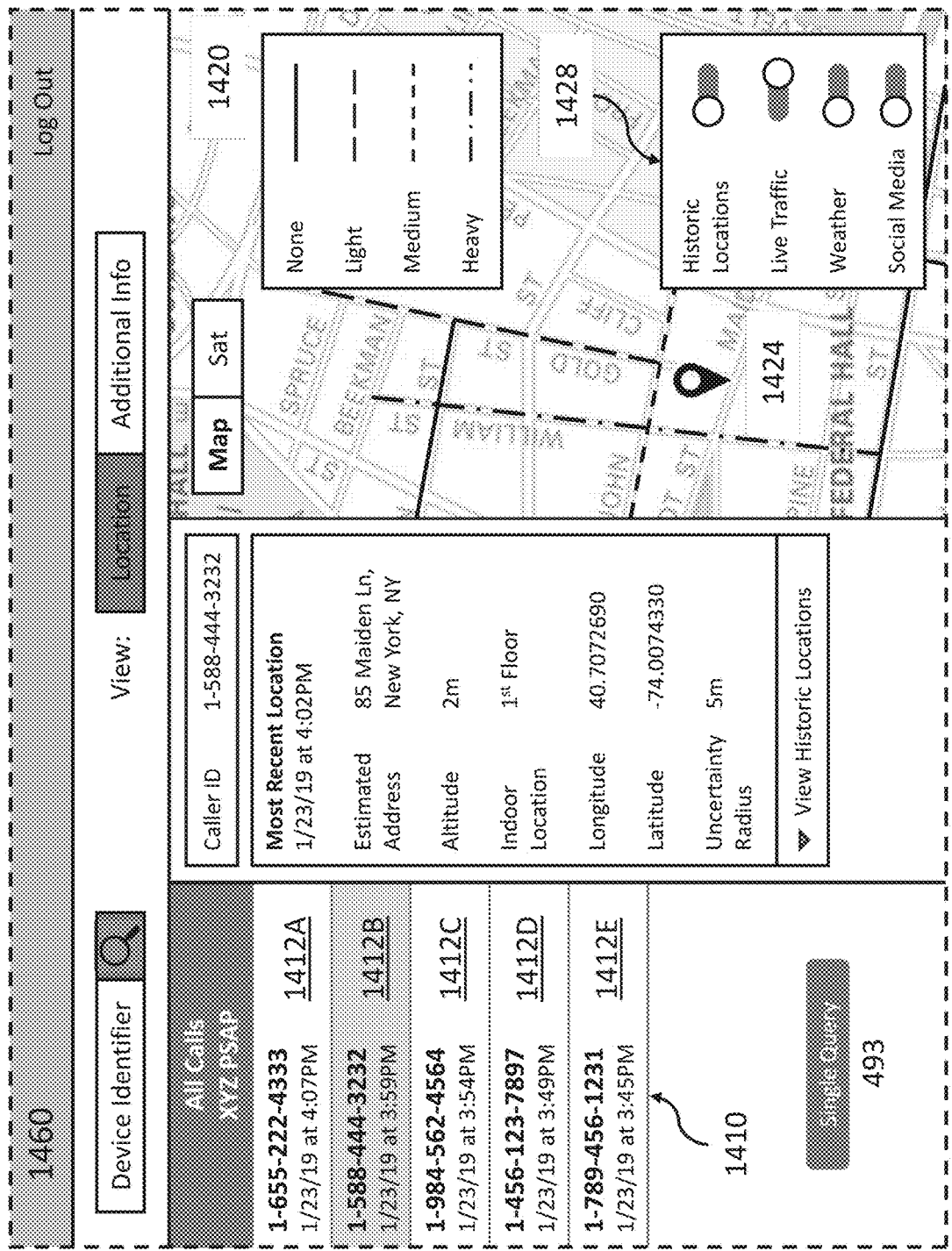
Figure 14C:
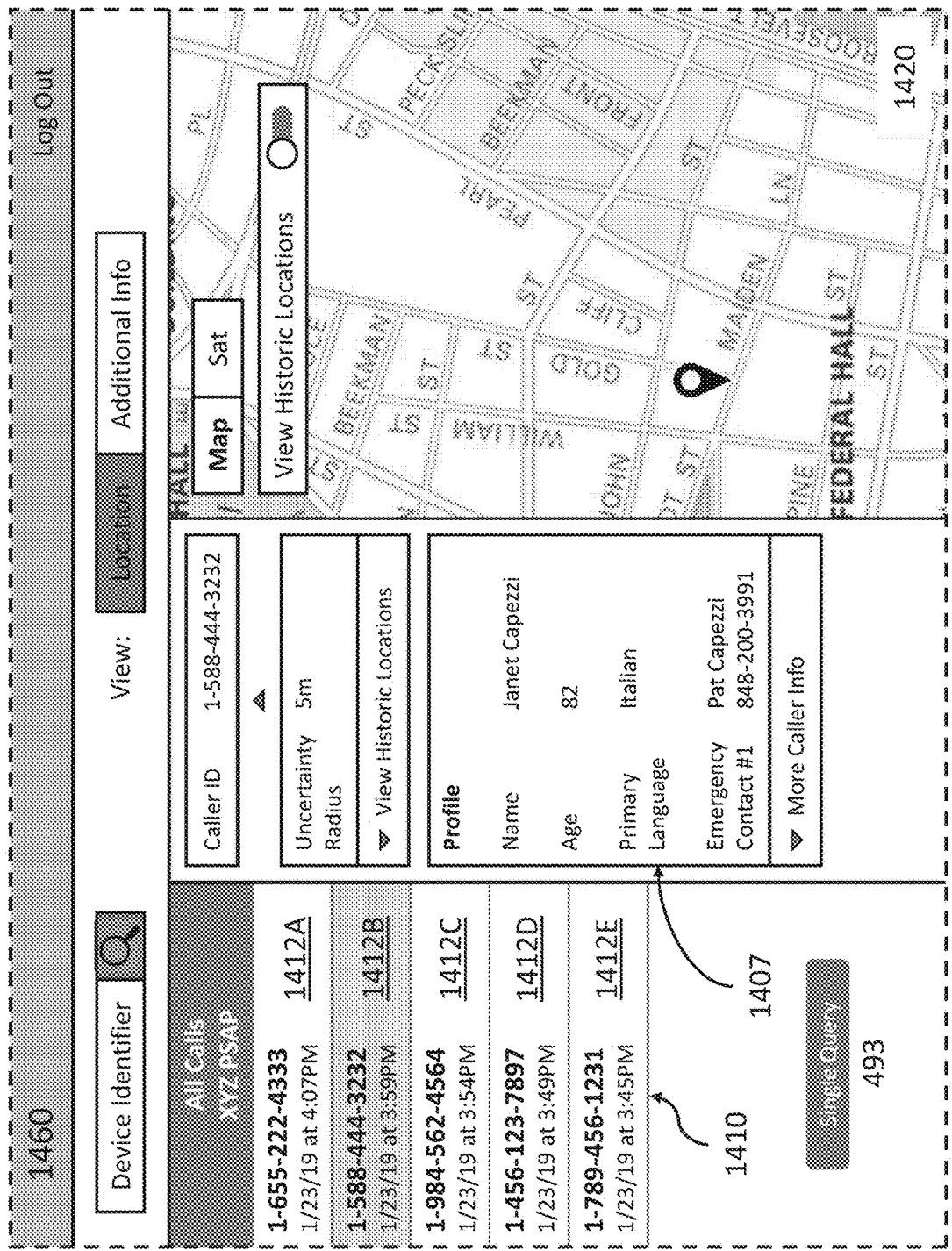

In some embodiments, a user of the emergency response application is enabled to access a single incident view from the jurisdictional awareness view. In some embodiments, the single incident view is accessed by the user selecting an incident location or an incident listed on the incident queue. FIG. 13C illustrates the selection of an incident 1312C in the incident queue 1310 to enter the single incident view. In some embodiments, the single incident view enlarges or moves the user's interactive map 1320 to detail the environment around the incident location 1324 (in the example depicted by FIG. 13C, incident location 1324C) corresponding to the selected incident 1312 (in the example depicted by FIG. 13C, incident 1312C). In some embodiments, enhanced location data 1303 or additional data (as depicted by FIG. 14C) is available in the single incident view.

In some embodiments, the single incident view enables a user to access various additional features. For example, in some embodiments, the single incident view enables the viewing of past location data (also referred to as "historic location data") through the use of a toggle button 1305A or menu selection 1305B. FIG. 14A illustrates the use of the past location data feature. In some embodiments, toggling the historic locations button 1405 allows the user to view the past locations 1426 (also referred to as "historic locations") associated with a particular incident 1412 listed in the incident queue 1410. As mentioned above, in some embodiments, the emergency response application can receive location updates regarding an incident 1412 and update the corresponding incident location 1424 accordingly. By selecting to see historic location data for a particular incident 1412, a user can see past locations 1426 associated with an incident 1412 as well as the current location (represented by the incident location 1424) associated with the incident 1412, as depicted by FIG. 14A. FIG. 14A depicts five incidents 1412 listed in the incident queue, incidents 1412A-1412E. In the example depicted by FIG. 14A, incident 1412B has been selected to bring up a single caller view for the incident 1412B. In response, the interactive map 1420 has zoomed in on the incident location 1424 associated with incident 1412B. Additionally, the user has selected to see historic locations 1426 by toggling the historic locations button 1405. In response, the interactive map 1420 now displays markers for historic locations 1426 associated with the incident 1412B. In some embodiments, the emergency response application displays a predetermined maximum number of past or historic locations 1426. For example, in some embodiments, the emergency response application displays no more than three historic locations associated with a particular incident 1412. In some embodiments, the emergency response application displays all of the historic locations 1426 associated with a particular incident 1412. In some embodiments, date and time is displayed when the user selects or moves the cursor over a past location data marker. In some embodiments, past location markers and the current location marker are displayed. In some embodiments, past location markers are automatically denoted or visibly distinct from current location markers. For example, past location markers may be denoted as shades of color, wherein more distant location markers are lighter shades, while the current location marker is the darkest shade of the color, or a different color. For example, as depicted in FIG. 14A, the current (e.g., most recent) location marker is depicted in black while the past location markers are depicted in white.

In another example, in some embodiments, the single incident view enables a user of the emergency response application to access one or more data layers. In some embodiments, a data overlay comprises an additional source of information. Examples of such information sources include IoT sensors (e.g., temperature sensor, camera/video camera), first responder devices (e.g., police vehicle console), wearable sensors (e.g., heart monitor), third party databases, and other relevant sources. In some embodiments, the jurisdictional awareness view is configured to be customizable to show one or more data overlays (or none) based on user configured settings. For example, FIG. 14B depicts the single incident view of the jurisdictional awareness view displaying a data layer. In this example, the jurisdictional awareness view provides a menu of data layers 1428. In this example, the menu of data layers 1428 includes toggles for four different data layers: historic locations (as described above), live traffic, weather, and social media. In the example depicted by FIG. 14B, incident 1412B has been selected and a user has selected the live traffic data layer to be turned on. In response, the jurisdictional awareness view has displayed traffic levels on the streets and roads around the incident location 1424 associated with incident 1412B. In this example, four different levels of traffic are displayed within the interactive map: none, light, medium, and heavy. Traffic levels around the location of an emergency may be particularly helpful for emergency service providers in dispatching first responders to the location. In some embodiments, the weather data layer displays weather conditions in the vicinity of an incident location 1424. In some embodiments, the social media data layer displays relevant social media data, such as social media posts regarding emergencies in the vicinity of an incident location 1424. The emergency response application may provide any type of data layer that offers emergency service providers helpful information in responding to emergencies.

For example, in some embodiments, the jurisdictional awareness view displays the location of available emergency services within a variable proximity to one or more incident locations 1424 (e.g., an emergency services data layer). In some embodiments, the jurisdictional awareness view displays the location of one or more first responders. In some embodiments, the location of a first responder that is assigned to and/or actively responding to an incident 1412 is displayed. In some embodiments, the location of the first responder is provided in real-time. In some embodiments, an estimated time to arrival and/or distance to arrival are displayed (e.g., calculated using the shortest or fastest path between the first responder and the incident location). In some embodiments, the emergency response application enables an ESP to coordinate the dispatch of emergency responders to incident locations 1412, so as to reduce response times and improve the allocation of resources. In some embodiments, the emergency response application is updated in response to the dispatch of a first responder to an incident location 1412. In some embodiments, the emergency response application is updated manually or automatically. In some embodiments, the jurisdictional view is used improve the coordination of first responder resources during large scale emergencies such as natural disasters, industrial accidents, and acts of terror.

In another example, in some embodiments, the jurisdictional awareness view displays one or more sensors within a variable proximity to one or more incident locations 1412 (e.g., a sensor data layer). In some embodiments, the one or more sensors comprise physiological sensors and/or environmental sensors. In some embodiments, the sensors sense one or more environmental or health/physiological parameters. In some embodiments, the environmental parameter is selected from the group consisting of light, motion, temperature, pressure, humidity, vibration, magnetic field, sound, smoke, carbon monoxide, radiation, hazardous chemicals, acid, base, reactive compounds, volatile organic compounds, and smog. In some embodiments, health parameters include heart rate, pulse, electric signals from the heart, blood oxygen levels, blood pressure, blood sugar level, and other health parameters. In some embodiments, a sensor is an Internet of Things (IoT) device such as a home thermostat, vehicle console, a pacemaker implant, etc. As used herein, IoT refers to the ever-growing network of physical devices, buildings, vehicles, and other objects that feature an IP address for internet network connectivity for exchanging data. In many cases, IoT devices are embedded with electronics, software, sensors, network connectivity, or a combination thereof. In some embodiments, IoT devices feature an IP address for internet connectivity. In addition to an IP address, an IoT device is optionally associated with a MAC address or an SSID. It is understood that, IoT devices are connected with one or more other devices through Bluetooth®, Wi-Fi, or other wired and/or wireless technologies which allow for transfer of data.

In some embodiments, the IoT device is in a network of sensors. As an example, IoT networks, wireless sensor networks (WSN) or wireless sensor and actuator networks (WSAN) monitor environmental parameters such as temperature, pressure, sound, etc., using a network of sensors or devices. When one sensor or device detects a sensed value outside of the identified range indicating a likely emergency, it will pass the data to other devices in the network. In some embodiments, the sensor network is a Wi-Fi, WiMAX, or LTE MESH network. In some embodiments, the sensor or IoT devices form nodes in the sensor network. In some embodiments, the sensor network includes a central node for controlling the network. In some embodiments, the sensor network has a distributed architecture to reduce the impact of a failed node.

In some embodiments, an IoT device comprises at least one of the following components including a sensing component (e.g., thermocouple), a networking component (a radio transceiver with an antenna or connection for an external antenna), a microcontroller, an electronic circuit connected to the sensing component, and an energy source. In some embodiments, the sensor network is controlled by a center console (e.g., a smart home console).

In some embodiments, the user of the emergency response application can disable the jurisdictional awareness view by selecting a location marker or a device identifier on the call queue. In some embodiments, the user of the emergency response application can disable the jurisdictional awareness view by way of a toggle button or a menu selection.

Emergency Response Application Additional Data

Figure 15:
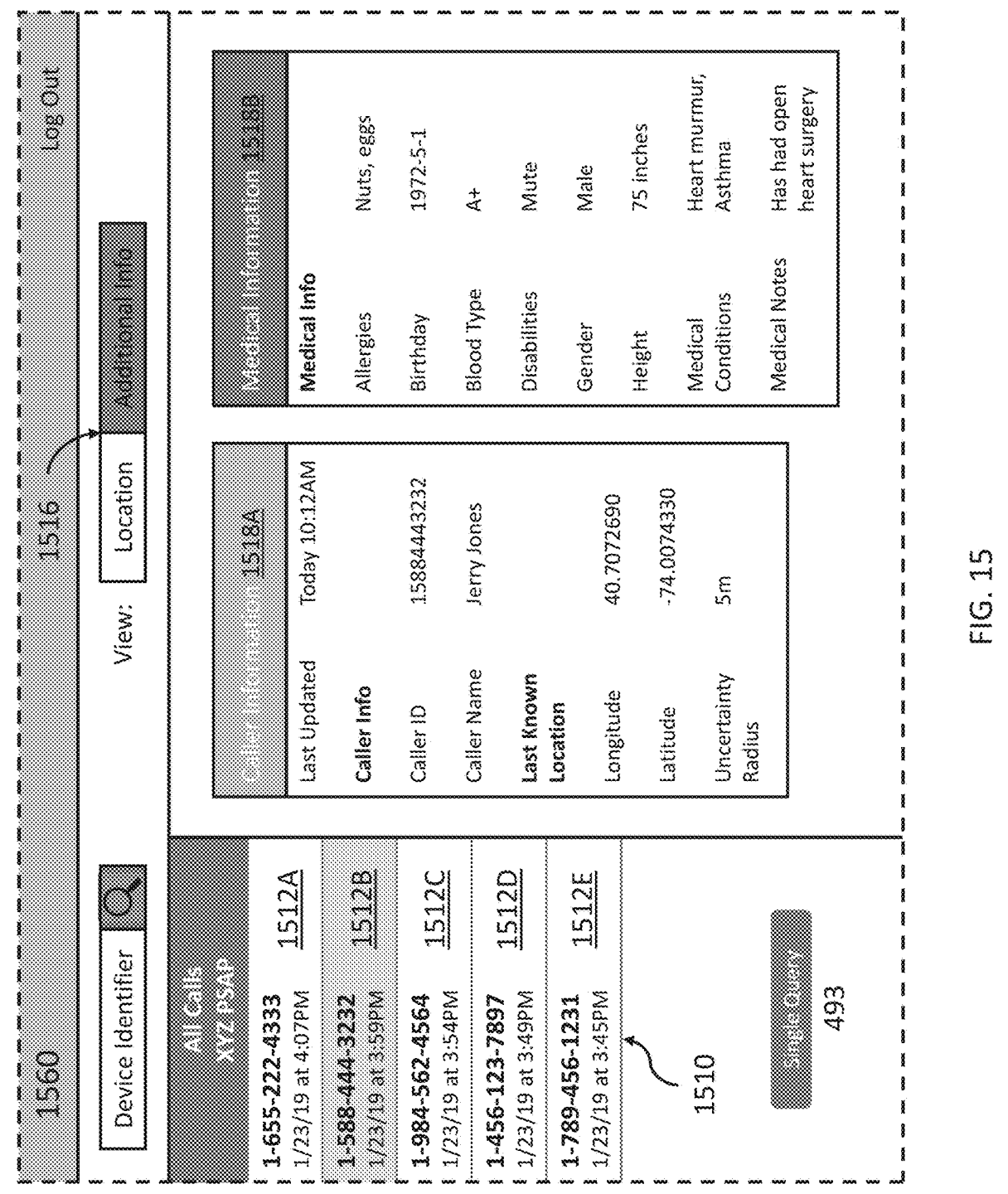

In some embodiments, the emergency data transmitted from the clearinghouse to the emergency response application includes additional data or information, as described above. For example, as described above, additional information can include, but is not limited to: service data reference, full name, email, emergency contacts, addresses, language, occupation, phone numbers, websites, gender, height, weight, ethnicity, profile picture, allergies, medical conditions, medications, disabilities, blood type, medical notes, birthday, and additional comments. In some embodiments, the emergency response application displays additional information included in the emergency data associated with a device identifier within the GUI, as depicted by FIGS. 14C & 15. In some embodiments, the emergency response application displays the additional information within the dashboard, as described above. In some embodiments, the emergency response application displays additional information included in the emergency data associated with the device identifier within a page separate from the dashboard. In some embodiments, a user can access the page displaying the additional information by selecting an additional information button or tab within the GUI. In some embodiments, the emergency response application displays the additional information within the jurisdictional awareness view, as depicted by FIG. 14C. For example, in some embodiments, when a user selects a particular incident 1412 listed in the incident queue 1410, thereby bringing up the single incident view for the particular incident 1412, the emergency response application displays additional data associated with the device identifier associated with the incident 1412, such as the profile information 1407 depicted by FIG. 14C. In some embodiments, as depicted by FIG. 14C, the emergency response application displays additional data above or below enhanced location data associated with an incident. FIG. 15 depicts an additional data displayed within the emergency response application. In some embodiments, when a user selects a particular incident 1512 listed in the incident queue 1510, thereby bringing up the single incident view for the particular incident 1512, the emergency response application presents a toggle 1516 for the user to select between location information and additional information. If the user selects additional information from the toggle 1516, the emergency response application displays additional information associated with the device identifier associated with the particular incident 1512.

In some embodiments, as depicted by FIG. 15, the emergency response application displays emergency data returned from the clearinghouse within discrete categories of emergency data categories, as described above. For example, in some embodiments, the emergency response application can separately display the "Demographics," "Contact Information," and "Addresses" groups of emergency data categories in individual sections. In some embodiments, the "Demographics," "Contact Information," and "Addresses" groups of emergency data categories (as described above) are displayed sequentially under a "Personal Information" (as described above; also referred to as "Caller Information") section of the GUI. In some embodiments, a "Medical Information" (as described above) section is displayed below the "Personal Information" section. In some embodiments, the GUI includes one or more tabs or sections to filter emergency data categories. For example, as depicted in FIG. 15, GUI can include a "Caller Information" tab or section 1518A and a "Medical Information" tab or section 1518B. In some embodiments, the GUI can include a "Location" tab or section, a "Caller-Provided Locations" tab or section, a "Devices" tab or section, and a "Directions" tab or section. In some embodiments, a "Directions" tab can be selected within the GUI to render a map displaying directions from a PSAP to a location of an emergency situation. In some embodiments, the map is capable of providing real-time or near real-time traffic updates.

Jurisdictional Query

As described above with respect to FIG. 12, there are several advantages for jurisdictional query as opposed to a simple query. A simple query may be sent to a third-party server based on a device identifier such as a phone number, SIM card number, IMEI number, etc. Typically, only one emergency alert will be returned from a simple query. In some embodiments, the jurisdictional query can be sent as a data request to a clearinghouse and displayed for an ESP as shown in FIGS. 13A-C. Even in the case where one phone is used to make multiple emergency calls, the returned emergency alerts are going to be likely regarding one incident. In contrast, a jurisdictional query is associated with an identifier of an agency or ESP, wherein all emergency alerts within the jurisdiction of the agency or ESP will be returned. In this way, the jurisdictional query can provide situational awareness to an ESP user regarding emergencies within their jurisdiction and can assist in providing effective and efficient response.

Figure 16:
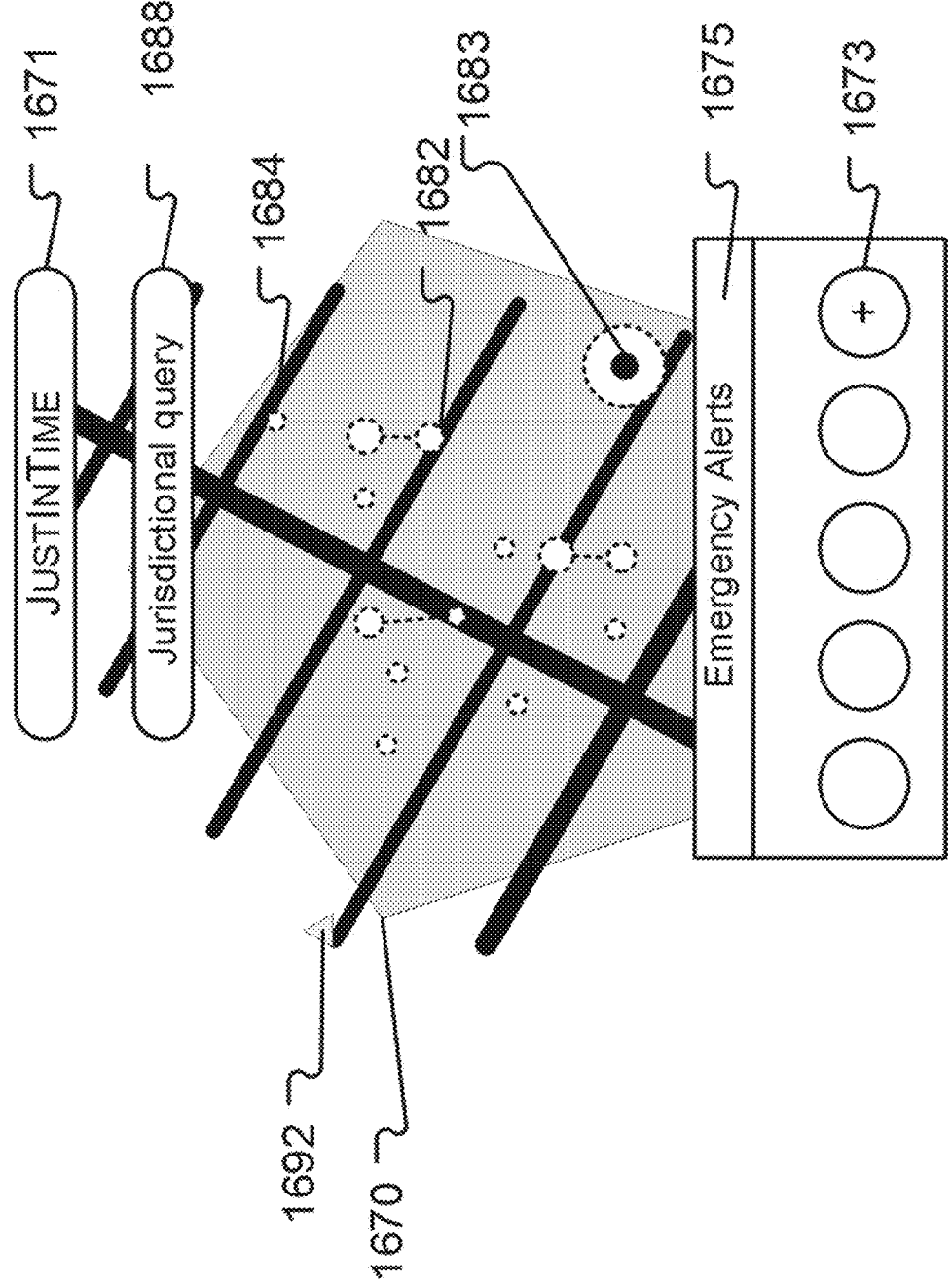
FIG. 16 illustrates the use of the jurisdictional query within an emergency response application, in accordance with certain embodiments.

FIG. 16 illustrates a non-limiting example of a graphical user interface displaying the returned results (i.e., emergency alerts 1675) for a specific jurisdictional query for an exemplary agency. For example, an ESP user (e.g. a PSAP call taker, an emergency responder, a police beat within the jurisdiction of the police station) may log-in to the emergency response application 1671 which may be displayed in jurisdictional query box 1688 (e.g., geofence of PSAP A). The jurisdictional boundary associated with the log-in credentials of the ESP user will be retrieved by the system and emergency alerts 1675 may be displayed for the ESP user to provide appropriate emergency response.

Various types of situational awareness information about the emergency can be displayed on the map. In some embodiments, the emergency alerts 1675 includes emergency calls (e.g., 911 calls) and alternative emergency alerts (such as SMS alerts, emergency alarms, web-based alerts, etc.). In some embodiments, emergency alerts 1675 provides supplemental data related to incoming emergency calls into a particular ESP agency. In some embodiments, emergency alerts 1675 includes primary requests for service, where the ESP has a limited time to claim and respond to the emergency.

As depicted, an emergency location 1683 may be selected to obtain emergency data regarding the emergency or claiming the emergency. The emergency location 1683 may include latitude-longitude, an address, a jurisdictional view of assets, a proximity radius from the emergency location, a proximity radius from landmarks, etc.

The geofence 1670 (e.g., a jurisdiction or sub-jurisdiction for the ESP or agency) corresponding to the credentials of the ESP user or responder may be displayed as a data overlay on a geographical map. Emergency locations outside the sub-jurisdiction (or alternatively in the geofence buffer zone) may be depicted using a different symbol (e.g., triangle 1692). In some cases, the ESP user may be able to view different types of events such as fire emergencies (big circles 1682) and medical emergencies (small circles 1684) within its jurisdiction. In some embodiments, the type of emergency may be further sub-divided to indicate different types of police emergencies (e.g., break-ins, altercations, gun-related incidents, mass casualty incidents, etc.), medical emergencies (e.g., emergencies that require ambulance dispatch, minor emergencies, etc.), fire emergencies (e.g., fire alarm, structural fires, etc.).

Although not shown, the ESP member may click on an emergency for additional data regarding the emergency (e.g., health sensor data for a medical emergency may be available). It is understood that various types of access controls may be used to limit access to private data, such as personally identifiable information may be masked, use of a pre-screening such as candidate screen with age and sex of the person in the emergency, RFIDs, QR codes, user consent procedures, etc. Although not shown, the responder 1680 may claim, cancel or mark off after the emergency has been responded to or canceled. Various types of emergencies, assets (such as medical and safety assets) can be viewed using the options 1673.

In another example, an ESP dispatcher may share a similar geographical map of medical assets on display for emergency responders in the field. The jurisdictional view may include the emergency location 1683 on the geographical map and the ESP users view assets that are in proximity to the emergency location for sending the response. If current location of the responders is available (e.g., 1682 may be squad cars), the movement of response assets (e.g., fire trucks sent to the scene) can also be monitored on the map. In some embodiments, medical assets include hospitals, clinics, doctors, nurses, pharmacies, first aid kits, IoT devices, cameras (e.g., CCTVs), and/or other assets. In some embodiments, the locations of the medical assets are displayed based on their physical addresses listed on public and private lists or databases or from communication devices in those facilities. It is understood that the viewed area of the map is adjustable by zooming in or out, rotating the angle of view, and/or panning.

It is understood that the screenshot in FIG. 16 is a non-limiting example and several variations are contemplated. In some embodiments, the map shows safety assets (such as police, private security personnel, fire extinguishers, fire hydrants, chemical showers, etc.), emergency responders (e.g., EMTs, medical services providers (commonly referred to as EMS), paramedics, etc.), volunteers (e.g., fire marshals, etc.). In some embodiments, the map shows safety assets (such as police, private security personnel, fire extinguishers, fire hydrants, chemical showers, drones, cameras, IoT devices, etc.), emergency responders (e.g., EMTs, paramedics, police vehicles, tow trucks, etc.), volunteers (e.g., fire marshals, etc.).

Non-limiting examples of geographical data layers including "police assets", "fire response assets", "safety assets", "drone assets", "IoT devices", "CCTVs", "vehicle rescue assets", "pet rescue assets", "water rescue assets" may also be generated.

Multiple Emergency Management Systems

As described above, in some embodiments, an emergency management system (EMS) is a system of devices, servers, or processors configured to manage the flow of emergency data from emergency data sources (e.g., connected devices or third-party servers) to emergency data recipients (e.g., emergency service providers (ESPs), ESP personnel, or other emergency management systems, as described below). As described above, an EMS may manage this flow of emergency data between sources and recipients in any number of ways. For example, in some embodiments, an EMS stores emergency data received from one or more sources and transmits emergency data to an ESP upon request, as described above. The emergency data can then be displayed within an emergency response application, as described above. In other embodiments, an EMS establishes an active communication link with an ESP (e.g., through an emergency response application, as described above), and, when the EMS comes in possession of an emergency alert or emergency data tagged with an identifier of the ESP, the EMS instantly and automatically transmits the emergency alert or the emergency data tagged with the identifier of the ESP to the ESP (e.g., through the active communication link), as described above. In some embodiments, the EMS receives an emergency alert or emergency data that was tagged with an identifier of an ESP before it was received by the EMS, as described above. In some embodiments, the EMS receives an emergency alert or emergency data and then tags the emergency alert or emergency data with an identifier of an ESP itself, such as by using a geofencing system, as described above.

Figure 17:
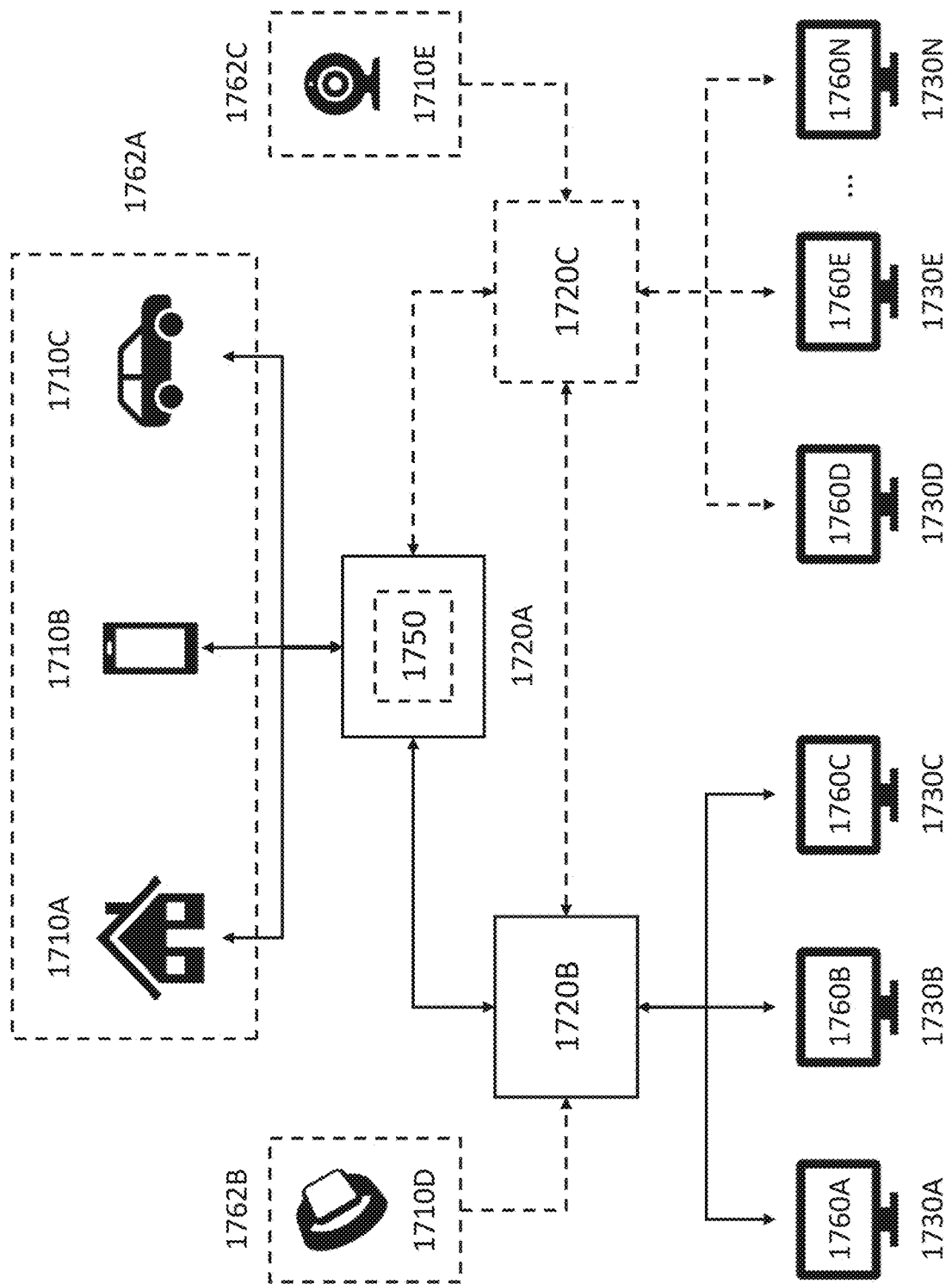
FIG. 17 depicts a diagram of a system for receiving and transmitting emergency data by an emergency management system (EMS), in accordance with certain embodiments.

In some embodiments, as described below, two or more separate and discrete emergency management systems (e.g., a first EMS and a second EMS) may function cooperatively in managing the flow of emergency data from emergency data sources to emergency data recipients. FIG. 17 depicts a diagram of two or more emergency management systems (EMSs) functioning cooperatively to manage the flow emergency data from one or more emergency data sources to one or more emergency data recipients. As depicted in FIG. 17, in some embodiments, a first EMS 1720A is communicatively coupled to one or more emergency data sources 1762A. In this example, as depicted in FIG. 17, the one or more emergency data sources 1762A communicatively coupled to the first EMS 1720A include home security systems 1710A, mobile phones 1710B, and vehicular telematics systems 1710C. The first EMS 1720A may include a clearinghouse 1750 for emergency data, as described above. As depicted in FIG. 17, the first EMS 1720A is also communicatively coupled to a second EMS 1720B, which may include its own clearinghouse for emergency data. The second EMS 1720B, as depicted by FIG. 17, is communicatively coupled the first EMS 1720A, one or more emergency data sources 1762B, and one or more emergency service providers (ESPs) 1730, such as through an emergency response application 1760. In this example, as depicted in FIG. 17, the one or more emergency data sources 1762B communicatively coupled to the second EMS 1720B include wearable devices 1710D.

As mentioned above, in some embodiments, a first EMS (e.g., EMS 1720A) and a second EMS (e.g., EMS 1720B) may function cooperatively to manage the flow of emergency data from one or more emergency data sources 1762 to one or more emergency data recipients (e.g., ESPs 1730). For example, as depicted in FIG. 17, a first EMS may have access to one or more emergency data sources 1762 that a second EMS does not have access to, and vice versa. Or, for example, as depicted in FIG. 17, a first EMS may have access to one or more emergency data recipients (e.g., ESPs 1730) that a second EMS does not have access to, and vice versa. In such circumstances, a first and second EMS may desire to function cooperatively to most effectively and efficiently achieve a shared goal of assisting the response to an emergency. For example, as depicted in FIG. 17, the first EMS 1720A is communicatively coupled to three sources of emergency data (electronic devices 1710A-1710C) that the second EMS 1720B does not have access too. However, the second EMS 1720B is communicatively coupled to three ESPs (ESPs 1730A-1730C) that the first EMS 1720A does not have access to. Therefore, if an emergency occurred in the jurisdiction of one of those ESPs (ESPs 1730A-1730C) and the first EMS 1720A had access to emergency data from one of those electronic devices (electronic devices 1710A-1710C) that may be relevant to the emergency, the first EMS 1720A and the second EMS 1720B may desire to work together in order to transmit the potentially relevant emergency data to the appropriate ESP 1730.

For example, in some embodiments, when the first EMS 1720A receives an emergency alert or emergency data including an emergency location from one of the emergency data sources 1762A coupled to the first EMS 1720A (e.g., if a person in an emergency dials 911 from a mobile phone 1710A communicatively coupled to the first EMS 1720A, which prompts the mobile phone 1710A to transmit an emergency alert to the first EMS 1720A), the first EMS 1720A can access one or more geofences associated with one or more ESPs 1730 and determine if the emergency location falls within any of the one or more geofences, as described above. In this example, the first EMS 1720A determines that the emergency location falls within the geofence associated with ESP 1730B. The first EMS 1720A then tags the emergency alert or the emergency data associated with or included in the emergency alert (e.g., the emergency location, a user or device identifier, a timestamp, etc.) with an identifier of ESP 1730B and stores the emergency alert or emergency data tagged with the identifier of ESP 1730B in one or more databases within or accessible by the first EMS 1720A. In some embodiments, if the first EMS 1720A is aware that the second EMS 1720B is communicatively coupled to ESP 1730B, the first EMS 1720A can autonomously and automatically transmit the emergency alert or emergency data tagged with the identifier of ESP 1730B to the second EMS 1720B for transmission to ESP 1730B (i.e., the emergency alert or emergency data is "pushed" to the second EMS). In some embodiments, whether or not the first EMS 1720A is aware that the second EMS 1720B is communicatively coupled to ESP 1730B, the first EMS 1720A does not transmit the emergency alert or emergency data tagged with the identifier of ESP 1730B to the second EMS 1720B unless and until the first EMS 1720A receives an emergency data request including the identifier of ESP 1730B from the second EMS 1720B (i.e., the emergency alert or emergency data is "pulled" by the second EMS). For example, in some embodiments, the second EMS 1720B does not request emergency data regarding a particular ESP from the first EMS 1720A unless the second EMS 1720B detects an active communication link established between the second EMS 1720B and the particular ESP (e.g., through the emergency response application 1760B), as described above. In this example, an active communication link has been established between the second EMS 1720B and ESP 1730B, so the second EMS 1720B transmits an emergency data request including the identifier of ESP 1730B to the first EMS 1720A. In turn, the first EMS 1720A then retrieves and transmits the emergency alert or any or all emergency data tagged with the identifier of ESP 1730B to the second EMS 1720B for transmission to ESP 1730B. The second EMS 1720B can then transmit the emergency alert or emergency data tagged with the identifier of ESP 1730B to ESP 1730B, where the emergency alert or emergency data may then be displayed within the emergency response application 1760B, such as through a jurisdictional awareness view, as described above. In some embodiments, after an ESP 1730 establishes an active communication link with the second EMS 1720B, the second EMS 1720B periodically transmits subsequent emergency data requests including the identifier of the ESP 1730 to the first EMS 1720A to receive new or updated emergency data tagged with the identifier of the ESP 1730. For example, after an ESP 1730 establishes an active communication link with the second EMS 1720B, the second EMS 1720B transmits emergency data requests including the identifier of the ESP to the first EMS 1720A at an interval of 1 second, 2 seconds, 3 seconds, 4 seconds, 5 seconds, 10 seconds, or 15 seconds. However, the second EMS 1720B may periodically transmit emergency data requests including the identifier of the ESP to the first EMS 1720A at any interval of time. In some embodiments, the second EMS 1720B periodically transmits emergency data requests including an identifier of an ESP to the first EMS 1720A throughout the duration of the active communication link established between the ESP and the second EMS 1720B.

In some embodiments, when a second EMS (e.g., EMS 1720B) receives an emergency alert or emergency data from a first EMS (e.g., EMS 1720A), whether or not the emergency alert or emergency data is pushed to the second EMS or pulled by the second EMS (as described above), the second EMS 1720B can query one or more other emergency data sources 1762B that are communicatively coupled to the second EMS 1720B to determine if any additional emergency data associated with the emergency alert or the emergency data received from the first EMS 1720A is available, so that the second EMS 1720B may provide the appropriate emergency data recipient (e.g., an ESP 1730) with as much relevant emergency data as possible. For example, as depicted in FIG. 17, the second EMS 1720B has access to at least one type of emergency data source 1762B, wearable devices 1710D, that the first EMS 1720A does not have access to. In this example, if the first EMS 1720A receives an emergency alert including a user identifier (e.g., a phone number) and an emergency location that the first EMS 1720A determines to be within a geofence associated with ESP 1730A, the first EMS 1720A can push the emergency alert and the emergency data included in the emergency alert (e.g., the user identifier and the emergency location) to the second EMS 1720B for transmission to ESP 1730A (e.g., if the first EMS 1720A is aware that the second EMS 1720B is communicatively coupled to ESP 1730A, as described above). In this example, before or after the second EMS 1720B subsequently transmits the emergency alert or the emergency data included in the emergency alert to ESP 1730A, the second EMS 1720B can transmit a third-party query (as described above) including the user identifier (e.g., the phone number associated with the emergency alert) to the one or more emergency data sources 1762B. In this example, heartrate data from a wearable device 1710D associated with the user identifier (e.g., the phone number associated with the emergency alert) is available, so the one or more emergency data sources 1762B return the heartrate data associated with the user identifier to the second EMS 1720B. The second EMS 1720B can then transmit the heartrate data associated with the user identifier (and, by extension, the emergency alert) to the ESP 1730A, either with the emergency data included in the emergency alert or separately.

In some embodiments, a first EMS may be communicatively coupled to a plurality of other EMSs. For example, in some embodiments, as depicted by FIG. 17, a first EMS (e.g., EMS 1720A) may be communicatively coupled to a second EMS (e.g., EMS 1720B) and a third EMS (e.g., EMS 1720C), and all three EMSs may function cooperatively to manage the flow of emergency data from one or more emergency data sources to one or more emergency data recipients. As mentioned above, one EMS may have access to different emergency data sources 1762 or emergency data recipients (e.g., ESPs 1730) that one or more other EMSs may not have access to, and vice versa. For example, as depicted in FIG. 17, EMS 1720C has access to ESPs (e.g., ESPs 1730D-1730N) that EMS 1720B does not have access to. Therefore, it might benefit EMS 1720A to be communicatively coupled to both EMS 1720B and EMS 1720C, so that EMS 1720A may provide potentially lifesaving emergency data to as many ESPs 1730 as possible. In another example, as depicted in FIG. 17, EMS 1720C has access to at least one type of emergency data source 1762C, smart cameras 1710E, that neither EMS 1720A nor EMS 1720B has access to. Therefore, it might benefit EMS 1720B to be communicatively coupled to EMS 1720C, so that if EMS 1720B comes in possession of an emergency alert (or emergency data) tagged with an identifier of an ESP communicatively coupled to EMS 1720B (e.g., by pulling the emergency alert or emergency data from EMS 1720A (as described above), being pushed the emergency alert or emergency data from EMS 1720A (as described above), or by receiving an emergency alert from an emergency data source 1762B (as described above)) but not communicatively coupled to EMS 1720C (e.g., ESP 1730C), EMS 1720B may transmit an emergency data request including an identifier associated with the emergency alert (e.g., a phone number) to EMS 1720C to determine if there is any available additional emergency data associated with or relevant to the emergency alert from one or more smart cameras 1710E (e.g., a video feed from a smart camera in the vicinity of an emergency location associated with the emergency alert, or a video feed from a smart camera communicatively coupled to EMS 1720C. If EMS 1720C does find additional emergency data associated with or relevant to the emergency alert from one or more smart cameras 1710E, EMS 1720C can transmit the additional emergency data (e.g., a video feed from one of the smart cameras) to EMS 1720B to be transmitted to the ESP (e.g., ESP 1720C) in addition to the emergency alert or emergency data previously received by EMS 1720B. However, any number of EMSs may cooperate in any other way.

Digital Processing Device

In some embodiments, the platforms, media, methods and applications described herein include a digital processing device, a processor, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing dice is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX*, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In some embodiments, the non-volatile memory comprises magnetoresistive random-access memory (MRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a subject. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In some embodiments, the display is E-paper or E ink. In other embodiments, the display is a video projector. In still further embodiments, the display is a combination of devices such as those disclosed herein.

In some embodiments, the digital processing device includes an input device to receive information from a subject. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the platforms, media, methods and applications described herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, media, methods and applications described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, media, methods and applications described herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of barcode, route, parcel, subject, or network information. In various embodiments, suitable databases include, by way of non-limiting examples, relational databases, non-relational databases, object-oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Certain Terminologies

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, an "electronic device" or "computing device" is a digital processing device designed with one or more functionalities such as, for example, a communication device. In some cases, the computing device is a desktop or laptop computer associated with a public safety answering point. For example, a computing device associated with a public safety answering point is a computer that is part of a work station a computer operated by a PSAP dispatcher. In some instances, the PSAP dispatcher is working on location at the PSAP. In some embodiments, the PSAP dispatcher is working off-site from a remote location. A "producing device" refers to an electronic device with a communication component, which will allow it to send and receive information over a wireless channel, a wired channel, or any combination thereof (e.g., sending/receiving information over the Internet). Non-limiting examples of producing devices include a mobile phone (e.g., a smartphone), a laptop, a desktop, a tablet, a radio (e.g., a two-way radio), and a vehicular communication system. In some embodiments, a producing device includes a car security system (e.g., OnStar®), a home security system, or a home control system (e.g., a networked control system for providing network controlled and/or smart temperature control such as a Wi-Fi smart thermostat, lighting, entertainment, and/or door control, such as Nest( ). In some embodiments, a producing device is an Internet of Things (IoT) device. In some embodiments, the producing device is a sensor for sensing environmental or health indicators. In some embodiments, the sensor includes a sensing component and a communication component. In some embodiments, the producing device is a sensor in a sensor network or a device that controls a sensor network. In some embodiments, the producing device is a physical panic button or software "panic" button.

In some embodiments, a producing device is a wearable device (e.g., a communication device worn by a user, such as an Apple Watch). In some embodiments, a producing device (e.g., a wearable device) comprises one or more sensors. The one or more sensors optionally include, but are not limited to: a gyroscope, an accelerometer, a thermometer, a heart rate sensor, a barometer, or a hematology analyzer. As used herein, a "mobile wireless device" refers to a device that is portable and communicates wirelessly. In some embodiments, a user wears or carries the mobile wireless device on the user's person or in the user's vehicle. Non-limiting examples of mobile wireless devices include mobile or cellular phones, wearable devices (e.g., smart watch, fitness tracker, wearable sensor, smart glasses, etc.).

As used herein, a "querying device" refers to a communication device that is querying for the emergency data (e.g. by allowing a user to send an emergency data request). In some embodiments, the querying device is a computing device within an ESP computer system, PSAP computer system, or PSS computer system. For example, the querying device may be a stationary terminal at a PSAP or a PSS (e.g. a police station, a command center), a responder device (e.g. a police radio, a vehicle console in an ambulance, etc.).

As used herein, a "consuming device" refers to a communication device that is receiving the emergency data for servicing the emergency. In many cases, the consuming device is the same as the querying device (e.g. the device sending the emergency data request). In some embodiments, the consuming device may be different from the querying device. For example, an ESP administrator may obtain the emergency location via a querying device at the ESP, dispatch a private individual or entity to respond to an emergency, and provide the emergency location to the consuming device of the individual or entity.

As used herein, an "associated device" refers to a communication device that is associated with an electronic device. For example, a user is using several communication devices such as a mobile phone, a wearable, a home security system, a car computer. The user has registered these devices with his or her account(s) and linked these devices with a user name, user number(s), email address(es), home or other physical address(es). In some embodiments, associated devices include communication devices of at least one additional user who is associated with user, e.g., a husband and wife, a father and son, a patient and doctor, friends, work colleagues, etc. In some cases, the user has added the second user as an emergency contact, a primary contact, a secondary contact, or a member of a group (e.g., part of the same club, organization, or workplace). In some cases, user has agreed to share location and other data with the second user. In some embodiments, the second user is someone who is frequently contacted by the user and the communication device identifies the second user from the "Recently called" or "Frequently called" list. In some embodiments, the associated devices are devices that are proximal or near-by to the producing device such as obtained through a Wi-Fi scan. In some embodiments, an associated device is proximal to the triggering device when the location of the associated device is within 1, 5, 10, 15, 20, 25, 30, 35, 40, 45, 50, 60, 70, 80, 90, 100, 200, 300, 400, or 500 meters of the location of the producing device, including increments therein.

As used herein, the "device identifier" refers to information allowing identification of the device or a user of the device (e.g. a phone number associated with a user of a producing device). In some embodiments, the device identifier includes a phone number, email address, physical address, coordinates, IMEI number, IP address, BSSID, SSID or MAC address.

As used herein, an "emergency alert" refers to a communication relating to an emergency or non-emergency situation. In some embodiments, an emergency alert is an emergency request for assistance (e.g., the request is associated with an emergency situation). In some embodiments, an emergency alert is a phone call. In some embodiments, an emergency alert comprises an emergency indication. In further embodiments, an emergency indication is selected from one or more of the group consisting of traffic accident, police emergency, medical emergency, and fire emergency. In some embodiments, an emergency alert is a primary request for service where an agency or ESP has to claim and respond to an emergency. In some embodiments, emergency alerts are referred to as incidents within the emergency response application. In some embodiments, an emergency alert is associated with a non-emergency situation (e.g., request for a tow truck after car breaks down). In some embodiments, an emergency alert is associated with a device sending the alert. In other embodiments, an emergency alert is associated with a device not sending the alert (e.g., a proxy request on behalf of a second device and/or a member device in a group of devices). As used herein, an emergency alert is "associated" with a device or user when the emergency alert relates to an emergency or non-emergency situation involving the device or user. In some embodiments, an emergency alert comprises data associated with a device (or user thereof). In some embodiments, an emergency alert comprises data associated with an electronic device sending the alert or another device. For example, in some embodiments, an emergency alert comprises data associated with a device, wherein the data set comprises current and/or past location data. In another example, the data set comprises current and/or past health data associated with the user of an electronic device. In other embodiments, an emergency alert is sent and/or received separately from data associated with a device.

As used herein, a "first responder" or an "emergency responder" refers to any person or persons responsible for addressing an emergency situation. A first responder is optionally referred to as an "emergency responder." In some embodiments, a first responder refers to government personnel responsible for addressing an emergency situation. In some embodiments, a first responder is responsible for a particular jurisdiction (e.g., a municipality, a township, a county, etc.). In some embodiments, a first responder is assigned to an emergency by an emergency dispatch center (hereinafter, "EDC"), such as a PSAP. In some embodiments, a first responder responds to a request for emergency assistance placed by a user via a user communication device. In some embodiments, a first responder includes one or more firefighters, police officers, emergency medical personnel, community volunteers, private security, security personnel at a university, or other persons employed to protect and serve the public and/or certain subsets of the population.

As used herein, an "emergency service provider" (ESP) is a public or private organization or institution responsible for providing emergency services. For example, in some embodiments, an EDC (e.g., a public safety answering point (PSAP)), a fire department, a police department, and a hospital may all be considered emergency service providers. In some embodiments, an emergency responder is a member of an ESP. In some embodiments, an ESP personnel is a person who works at an ESP. For example, an ESP personnel may be a call-taker at a PSAP or a first responder at a fire department. In some embodiments, the ESP is a private call center. In some embodiments, the ESP is university or corporate campus police. There may be different types of ESPs (e.g., primary agencies, secondary agencies, public safety agencies, private agencies, etc.). Primary agencies may have authoritative responsibility to respond to emergencies within its geofence, while secondary agencies may be assigned to respond to emergencies by primary agencies. For example, the primary agency is a PSAP, while a secondary agency is a local medical service provider. In another example, the primary agency is a PSAP, while a secondary agency is a regional authority, where the jurisdiction of the secondary agency may overlap with the jurisdiction of the PSAP.

As used herein, a public safety service (PSS) refers to a local, state, or federal government agency or institution that is responsible for providing safety, security, or medical services to members of the public. Examples of public safety services include fire departments, police departments, and hospitals. In some embodiments, public safety services additionally include public safety answering points (PSAPs). A PSAP refers to a call center responsible for answering calls to an emergency telephone number for police, firefighting, and ambulance services. Trained telephone operators (also referred to as call-takers) are also usually responsible for dispatching these emergency services. The Federal Communications Commission (FCC) of the United States government maintains a PSAP registry. The registry lists PSAPs by an FCC assigned identification number, PSAP Name, State, County, City, and provides information on any type of record change and the reason for updating the record. The FCC updates the registry periodically as it receives additional information. In some embodiments, the ESP identifier or PSAP identifier comprises the FCC identification of the agency.

As used herein, a "emergency authority" refers entities or organizations that have been given authority by the government to service emergency alerts and calls (911, 112 or other emergency numbers) within a specific area (the "authoritative region"). Non-limiting examples of emergency authorities include PSAPs and various types of PSS such as emergency command centers.

As used herein, a "recipient" refers to one or more persons, services, or systems that receive a request for assistance (e.g., an emergency alert). The recipient varies depending on the location of the emergency and type of request. In some embodiments, a recipient is an emergency service provider (ESP). In some embodiments, a recipient is an emergency service when the request for assistance pertains to an emergency (e.g., a tier 2 emergency). In some embodiments, a recipient is an emergency management system. In some embodiments, a recipient is an emergency dispatch center (e.g., a public safety answering point or PSAP). In some embodiments, a recipient is an emergency dispatch center, wherein the request is first routed through an emergency management system (e.g., request is sent to the EMS, but ultimately is sent to an EDC). In some embodiments, a recipient is a dispatcher or call taker associated with a particular PSS such as a PSAP. In some embodiments, the recipient is located on-site at the PSS (e.g., PSAP station) or is working remotely (e.g., at home). In some embodiments, a recipient is a first responder (e.g., a communication device of a first responder). In some embodiments, a recipient is an associated device of a user or an account associated with the user. In some embodiments, a recipient is a non-emergency service or personnel, for example, a relative or friend. In such situations, a user of a communication device (or member device or second device) does not require emergency assistance but does need help.

As used herein, a "user" refers to one or more person or persons associated with a system, server, or device (e.g., electronic device, member device, second device, device of a first responder, etc.). As used herein, an "ESP user" or "ESP member" refers to a user of the emergency response application within the computer system of an agency or ESP.

In some embodiments, emergency data may designate a source (also referred to as a "data source" or "info source") from where the emergency data was received or generated. In some embodiments, the source is a public or private organization. In some embodiments, the organization provides a transportation service (e.g., taxi company, ride-sharing company, shipping company, railroad company, etc.). In some embodiments, a user utilizes a producing device to send an emergency alert or request for assistance and produce emergency data. In some embodiments, user refers to one or more persons who are paid subscribers of a network access service, for example, cellular service subscribers. In some embodiments, a user refers to anyone who gains access to a network via a router, for example, a Wi-Fi router, and is not a paid subscriber of any access service. In some embodiments, a device associated with a user is a device carried or worn on the person of the user (e.g., a phone or wearable device). In some embodiments, a device associated with a user is not carried or worn on the person of the user (e.g., a home security sensor or camera installed in the home of the user, a vehicle tracking system installed in a vehicle of the user, etc.).

As used herein, "data" refers to a collection of information about one or more entities (e.g., user of a user communication device) and/or an environment that pertains to characteristics of the one or more entities. In some embodiments, an entity is a person such as a user. In some embodiments, an entity is a thing (e.g., a house). For example, in some embodiments, data comprises sensor data from home sensors associated with a house. In this example, the data is also associated with one or more persons (e.g., the homeowner(s) and/or inhabitant(s)). In some embodiments, data refers to meta-data. In some embodiments, data comprises health information about the user of a communication device. In some embodiments, data comprises information about the surrounding environment of the user of the user communication device (e.g., surrounding temperature, location, elevation, barometric pressure, ambient noise level, ambient light level, surrounding geography, etc.). In some embodiments, data comprises information about other users that is pre-stored in a device or in a database (e.g., a database within a group of devices who are related to the user of the user communication device as predefined by the user). In some embodiments, the data set comprises information from two or more users of user communication devices, wherein each user is affected by an emergency situation. As an example, two unrelated users are involved in a vehicular collision, and each user sends a separate emergency alert (for traffic accident) using his/her communication device. In this example, the separate emergency alerts are associated (e.g., by an emergency management system and/or emergency dispatch center) with the same emergency based on the proximity of time, location, and emergency indication of the emergency requests. As a result, the data set for this accident comprises information from both user communication devices. In this example, the data set comprises location data from both devices (e.g., GPS coordinates, device-based hybrid location, "location services", etc.), biosensor data for one or both devices (e.g., biosensor data such as heart rate and blood pressure can be important in case of injury), and information about the vehicle driven by each user (e.g., make, model, and year of manufacture information stored on the device). In some embodiments, data comprises current data. In further embodiments, current data comprises information that is equal to or less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, or 60 minutes old, including increments therein. In further embodiments, current data comprises information that equal to or less than 1, 2, 3, 4, 5, 6, 7, 8, 9, 10, 11, 12, 13, 14, 15, 16, 17, 18, 19, 20, 21, 22, 23, or 24 hours old. In some embodiments, data comprises historical data. In further embodiments, historical data comprises information that is equal to or more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, or 60 minutes old, including increments therein. In further embodiments, historical data comprises information that equal to or more than 1, 2, 3, 4, 5, 6, 7, 8, 9, 10, 11, 12, 13, 14, 15, 16, 17, 18, 19, 20, 21, 22, 23, or 24 hours old. In some embodiments, the age of information is calculated from the date the information is first collected (e.g., when a sensor first detects a sensed parameter such as, for example, heart rate).

As used herein, "health data" refers to medical information associated with a user of a device. In some embodiments, health data comprises medical history such as, for example, past illnesses, surgery, food and/or drug allergies, diseases, disorders, medical diagnostic information (e.g., genetic profile screen), or any combination thereof. In some embodiments, health data comprises family medical history (e.g., family history of breast cancer). In some embodiments, health data comprises current health information such as, for example, current symptoms, current medications, and/or current illnesses or diseases. In some embodiments, health data comprises user age, height, weight, blood type, and/or other biometrics. In some embodiments, medical history comprises medical information that is equal to or more than 1, 2, 3, 4, 5, 6, 7, 8, 9, 10, 11, 12, 13, 14, 15, 16, 17, 18, 19, 20, 21, 22, 23, or 24 hours old. In some embodiments, medical history comprises medical information that is equal to or more than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days old. In some embodiments, current health information comprises information that is equal to or less than 1, 2, 3, 4, 5, 6, 7, 8, 9, 10, 11, 12, 13, 14, 15, 16, 17, 18, 19, 20, 21, 22, 23, or 24 hours old. In some embodiments, current health information comprises medical information that is equal to or less than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days old.

As used herein, "user data" refers to general information associated with a user of a device. In some embodiments, user data comprises user identity, user name, height, weight, eye color, hair color, ethnicity, national origin, religion, language(s) spoken, vision (e.g., whether user needs corrective lenses), home address, work address, occupation, family information, user contact information, emergency contact information, social security number, alien registration number, driver's license number, vehicle VIN, organ donor (e.g., whether user is an organ donor), or any combination thereof. In some embodiments, user data is obtained via user input.

As used herein, "sensor data" refers to information obtained or provided by one or more sensors. In some instances, a sensor is associated with a device (e.g., user has a communication device with a data link via Bluetooth with a wearable sensor, such as, for example, a heart rate monitor or a pedometer). Accordingly, in some embodiments, the device obtains sensor data from the sensor (e.g., heart rate from the heart rate monitor or distance traveled from the pedometer). In some instances, the sensor data is relevant to an emergency situation (e.g., heart rate during a cardiac emergency event). In some embodiments, a sensor and/or sensor device comprises an acoustic sensor, a breathalyzer, a carbon dioxide sensor, a carbon monoxide sensor, an infrared sensor, an oxygen sensor, an ozone monitor, a pH sensor, a smoke detector, a current sensor (e.g., detects electric current in a wire), a magnetometer, a metal detector, a radio direction finder, a voltage detector, an air flow meter, an anemometer, a flow sensor, a gas meter, a water meter, a Geiger counter, an altimeter, an air speed indicator, a depth gauge, a gyroscope, a compass, an odometer, a shock detector (e.g., on a football helmet to measure impact), a barometer, a pressure gauge, a thermometer, a proximity sensor, a motion detector (e.g., in a home security system), an occupancy sensor, or any combination thereof, and in some embodiments, sensor data comprises information obtained from any of the preceding sensors. In some embodiments, one or more sensors are physically separate from a user device. In further embodiments, the one or more sensors authorize the user device to obtain sensor data. In further embodiments, the one or more sensors provide or send sensor data to the user device autonomously. In some embodiments, the user device and the one or more sensors belong to the same group of devices, wherein member devices are authorized to share data. In some embodiments, a user device comprises one or more sensors (e.g., user device is a wearable device having a sensor or sensing component).

As used herein, "emergency data" refers to data pertaining to an on-going or historical emergency. The emergency data may be generated at the time of the emergency. The emergency data may be generated before the emergency occurs and may be made accessible when the emergency occurs. In some embodiments, the emergency data comprises location data, particularly the current location of the emergency (often times based on the location of the user device). Because of privacy and security concerns, emergency data must be stored, accessed, transmitted using security and privacy measures.

As used herein, "communication link" refers to a communication pathway from a device (e.g., communication device) to another device or to an intermediate device (e.g., a router) such as over a network. In some embodiments, the communication device establishes a communication link with another device or an intermediate device to transfer information (e.g., a location of the device) or to obtain information from a recipient such as, for example, location of a first responder assigned to a request for assistance associated with the communication device (e.g., device of first responder). In some embodiments, a communication link refers to the point-to-point communication channels, point-to-point and end-to-end data sessions, and/or the physical hardware facilitating the communication channel(s) (e.g., antennas used to communicate/transmit information). In some embodiments, a data session comprises session parameters and the network route taken from one device to another device.

As used herein, a "data session" refers to a communication session between two devices wherein data packets are exchanged between the devices. In some embodiments, a data session is setup using exchange of certain data packets, also called as "handshake signals," which are able to define the capabilities of the data session. For example, in some embodiments, the data session "handshake" provides for the ability to transfer multi-media data, voice data, and other data via the data session. In some embodiments, the data session is setup without the use of handshake signals, wherein the two devices involved share data packets according to a predefined protocol (e.g., a previously agreed upon protocol). In some embodiments, the data session is routed through an EMS, which stores the multi-media, voice, and/or other data from any of the devices that are part of the data session. In further embodiments, the EMS shares the data from the data session with the other device (e.g., device of a first responder). In some embodiments, the EMS manages the data session.

Modern communication devices, for example, smart phones, tablet computers, wearable communication devices, smart sensor devices and/or systems are often equipped with a variety of features for determining location information of the communication device using, for example, GPS, or triangulation with cellular phone towers. Modern communication devices also often include functionality to store data regarding a user of the communication device, for example, health information about the user.

In some embodiments, the communication device (or communication module of the device) communicates with a recipient through one or more data channels. In some embodiments, the recipient is an emergency management system. In some embodiments, the EMS routes communications to an EDC. In further embodiments, the EMS establishes a first data channel with the communication device and a second data channel between the EMS and the EDC, wherein the EMS bridges the first and second data channels to enable the communication device and the EDC to communicate. In some embodiments, the EMS converts data (e.g., data set) from the communication device into a format suitable for the EDC (e.g., analog or digital, audio, SMS, data, etc.) before sending or routing the formatted data to the EDC. In some embodiments, the EMS routes communications to a device associated with a first responder. In some embodiments, the communication device relays additional communications, information, and/or data sent or shared between member devices in the group of devices to the EMS or EDC after a request for assistance has been sent. In further embodiments, the additional information is relayed to the EMS or EDC after the request for assistance has been sent in order to provide current information that is relevant to the request. For example, in some instances, communications between member devices contain information relevant to the emergency (e.g., information that the user of member device who is experiencing a medical emergency suffers from diabetes). Accordingly, in some embodiments, the information is sent autonomously, at request of a user of the communication device, or at request of the recipient (e.g., EMS, EDC, first responder, etc.).

Examples

The following illustrative example is representative of embodiments of the invention described herein and is not meant to be limiting in any way.

Example

Just In Time, an emergency response company, aids emergency service providers (ESPs; such as public safety answering points, or "PSAPs") by gathering emergency data from a variety of sources and delivering the data directly to the emergency service providers. Traditionally, PSAPs are only technologically capable of receiving telephone calls (e.g., 9-1-1 emergency calls) with no additional data. Thus, when an emergency call is made to a PSAP from a mobile phone (with a dynamic and uncertain location), PSAP operators or call-takers must speak directly to the caller to determine the person's location. Unfortunately, many people involved in emergency situations are unable to articulate their location or may not even know it—and even if they do, the time spent articulating their location to the PSAP operator can often be the difference between life and death. Similarly, PSAP operators are forced to respond to emergencies with little or no information about the persons involved (e.g., health data or medical histories) or context of the emergencies (e.g., type of emergency, audio/video of the surroundings, etc.). Just In Time knows just how critical it is to quickly and accurately provide locations and situational/contextual information during emergencies to emergency service providers.

To aid PSAPs, Just In Time maintains and provides an Emergency Clearinghouse (hereinafter, "clearinghouse") that receives and stores data and information from a plurality of sources, such as mobile phones and mobile applications, internet of things (IoT) devices, intelligent vehicles systems, and other electronic devices. During an emergency, the clearinghouse can gather information stored within or otherwise accessible by the clearinghouse regarding the emergency and deliver the information to PSAPs. In order to provide access to the information stored within the clearinghouse to PSAPs as quickly and easily as possible, Just In Time develops and provides an emergency response application that can be integrated into their existing systems or accessed through a standard web browser.

The administrator of a PSAP in Georgia, Joe, learns of the helpful and potentially life-saving information stored within Just In Time's clearinghouse—such as accurate emergency locations and medical histories (hereinafter, "emergency data")—and that can be automatically pushed to registered PSAPs. Accordingly, Joe registers his PSAP with Just In Time, including submitting a GIS file providing a geofence of the jurisdiction of his PSAP.

Once registered, Joe then creates Nick Of Time accounts for any number of other members of his PSAP to use to access Nick Of Time. For example, Joe creates an account for one of the Georgia PSAP call-takers, Jane. Just In Time then sends Jane an email including a temporary password for her to use to access Nick Of Time. When Jane attempts to log into Nick Of Time, Nick Of Time checks the IP address that Jane's login attempt was received from, and determines that the IP address is different from the IP address Joe used to register the PSAP (e.g., Jane attempted to log in from a different computer within the PSAP). In response, Jane's login attempt is blocked, and her account is disabled. Nick Of Time presents Jane with two options for requesting an access code to reactivate her account: a phone call to the PSAP's non-emergency telephone number that will audibly relay the access code; or an email sent to Joe. This security method ensures that Jane is legitimately associated with the Georgia PSAP, as she must either be physically present at the PSAP, receive the access code from someone who is physically present at the PSAP, or receive the access code from Joe, who has been previously vetted.

Since Jane is physically present at the PSAP, she chooses to receive the phone call and records the access code that is dictated by the call. She submits the access code into Nick Of Time, which reactivates her account and adds her IP address to a list of authorized IP addresses. Nick Of Time then presents an jurisdictional awareness view on a computer display to Jane through the Nick Of Time graphical user interface (GUI), where Jane can view a master list and/or an interactive map showing one or more ongoing and recent incidents within the jurisdiction. Now that Jane has successfully logged into Nick Of Time, a persistent communication link associated with her PSAP is established between Jane's computer and the Just In Time clearinghouse through the Nick Of Time application. Jane soon receives an emergency call from a man named Eric, whose phone number is (555) 444-6666. Upon making the emergency call, Eric's smartphone automatically sends a current location (determined using the phone's GPS rather than cell tower triangulation) associated with Eric's phone number to a third-party server. The third-party server accesses a geofence associated with Jane's PSAP (i.e., the Georgia PSAP) and determines that Eric's location falls within the geofence, so the third-party server tags the location with an identifier of the Georgia PSAP.

Because there is a persistent communication link associated with Jane's PSAP (i.e., the Georgia PSAP) established between Jane's computer and the Just In Time clearinghouse through the Nick Of Time application, Just In Time periodically transmits a third-party query including an identifier of the Georgia PSAP to the third-party server every five seconds. Just as Jane received Eric's call, Just In Time transmits a third-party query including the identifier of the Georgia PSAP to the third-party server, and, because Eric's location has already been tagged with the identifier of the Georgia PSAP, the third-party server returns Eric's location to the Just In Time clearinghouse. The Just In Time clearinghouse in turn automatically transmits Eric's location, now tagged with the identifier of the Georgia PSAP, to Jane's computer, and displays Eric's location within the interactive map of the Nick Of Time emergency response application. The Nick Of Time application also generates a new incident for Eric's emergency call and displays Eric's phone number as an incident within the list of incidents for the Georgia PSAP. Just like that, Eric's location appears on Jane's computer before she even asks Eric for his location. Jane can simply ask Eric to confirm the location she has already received and immediately begin the process of dispatching emergency responders to provide care for Eric. In addition, the clearinghouse uses Eric's phone number to search its records for additional information including Eric's home and work addresses, Eric's medical history, and a phone number for Eric's mother, who is listed as Eric's emergency contact. The clearinghouse automatically transmits all of this additional emergency data to Jane's computer and displays the additional data within the Nick Of Time application as well, to increase the efficiency of Eric's emergency care.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An emergency management system (EMS) configured for providing emergency data to one or more of a plurality of emergency service providers (ESPs), the EMS comprising a memory, a network component, and at least one processor operatively coupled to the network component, the at least one processor operative to:
    a) detect an active communication link established between the EMS and a first ESP of the plurality of ESPs through an emergency response application executed on a computing device at the first ESP;
    b) transmit a third-party query comprising an identifier of the first ESP to a third-party server;
    c) receive emergency data tagged with the identifier of the first ESP from the third-party server, wherein the emergency data comprises device identifiers and emergency locations associated with the device identifiers corresponding to a plurality of emergency alerts;
    d) in response to detecting the active communication link between the EMS and the first ESP and receiving the emergency data tagged with the identifier of the first ESP, transmit the emergency data comprising the device identifiers and the emergency locations corresponding to the plurality of emergency alerts to the first ESP for display within the emergency response application.

2. The system of claim 1, wherein the emergency response application comprises a graphical user interface (GUI) displaying an interactive map and wherein the emergency location associated with one or more of the multiple emergency alerts is displayed within the interactive map.

3. The system of claim 1, wherein the emergency data tagged with the identifier of the first ESP further comprises medical data.

4. The system of claim 1, wherein the emergency data tagged with the identifier of the first ESP further comprises sensor data.

5. The system of claim 1, wherein the at least one processor is operative to transmit the third-party query comprising the identifier of the first ESP to the third-party server in response to detecting the active communication link established between the EMS and the emergency response application.

6. The system of claim 1, wherein the at least one processor is further operative to periodically transmit subsequent third-party queries comprising the identifier of the first ESP to the third-party server.

7. The system of claim 6, wherein the at least one processor is further operative to periodically transmit the subsequent third-party queries to the third-party server for the duration of the active communication link established between the EMS and the first ESP through the emergency response application.

8. The system of claim 1, wherein the computing device comprises a memory, a user interface, a network component, a display, and at least one processor operatively coupled to the network component, the at least one processor operative to:
    a) provide the emergency response application, the emergency response application comprising a graphical user interface (GUI) displaying an interactive map;
    b) receive the emergency data comprising the emergency locations tagged with the identifier of the first ESP; and
    c) display the emergency locations within the interactive map of the emergency response application.

9. The system of claim 8, wherein the emergency response application is a web application accessed through a web browser installed on the computing device at the first ESP.

10. The system of claim 9, wherein the emergency response application is a software application installed on the computing device at the first ESP.

11. The system of claim 1, wherein the at least one processor is further operative to:
    a) detect a second active communication link established between the EMS and a second ESP of the plurality of ESPs through an emergency response application executed on a computing device at the second ESP;
    b) transmit a third-party query comprising an identifier of the second ESP to a third-party server;
    c) receive emergency data tagged with the identifier of the second ESP from the third-party server, wherein the emergency data comprises device identifiers and emergency locations associated with the device identifiers corresponding to a second plurality of emergency alerts;

d) in response to detecting the second active communication link between the EMS and the second ESP and receiving the emergency data tagged with the identifier of the second ESP, transmit the emergency data comprising the device identifiers and the emergency locations corresponding to the second plurality of emergency alerts to the second ESP for display within the emergency response application executed on the computing device at the second ESP.

12. A computer-implemented method comprising:
   a) receiving a plurality of emergency alerts comprising device identifiers and emergency locations associated with the device identifiers from electronic devices;
   b) accessing one or more geofences associated with one or more emergency service providers (ESPs) from a plurality of geofences, the one or more geofences comprising a first geofence associated with a first ESP;
   c) determining that the emergency locations for the plurality of emergency alerts are within the first geofence associated with the first ESP;
   d) tagging emergency data comprising the device identifiers and emergency locations for the plurality of emergency alerts with an identifier of the first ESP;
   e) receiving an emergency data request comprising the identifier of the first ESP from a third-party emergency management system (EMS), wherein the third party EMS is communicatively coupled to the first ESP; and
   f) transmitting the emergency data comprising the device identifiers and the emergency locations tagged with the identifier of the first ESP to the third party EMS for transmission to the first ESP.

13. The system of claim 12, wherein the method further comprises:
   a) receiving a second emergency data request comprising the identifier of the first ESP from the third party EMS;
   b) retrieving updated emergency data tagged with the identifier of the first ESP; and
   c) transmitting the updated emergency data tagged with the identifier of the first ESP to the third party EMS for transmission to the first ESP.

14. The system of claim 12, wherein the method further comprises:
   a) receiving a second plurality of emergency alerts comprising second device identifiers and second emergency locations associated with the second device identifiers from second electronic devices;
   b) accessing the one or more geofences associated with one or more emergency service providers (ESPs) from the plurality of geofences, the one or more geofences comprising a second geofence associated with a second ESP;
   c) determining that the second emergency locations are within the second geofence associated with the second ESP;
   d) tagging emergency data comprising the second device identifiers and second emergency locations with an identifier of the second ESP;
   e) receiving a second emergency data request comprising the second identifier of the second ESP from the third-party emergency management system (EMS), wherein the third-party EMS is communicatively coupled to the second ESP; and
   f) transmitting the emergency data comprising the second device identifiers and the second emergency locations tagged with the identifier of the second ESP to the third-party EMS for transmission to the second ESP.

15. An emergency management system (EMS) comprising a memory, a network component, and at least one processor operatively coupled to the network component, the at least one processor operative to:
   a) determine an active communication link is established with a computing device providing an emergency response application at a first emergency service provider of a plurality of emergency service providers (ESP);
   b) query a database comprising a plurality of identifiers associated with the plurality of ESP to obtain an identifier associated with the first ESP;
   c) transmit a third-party query comprising the identifier associated with the first ESP to a third-party server;
   d) receive emergency data tagged with the identifier of the first ESP from the third-party server, wherein the emergency data comprises device identifiers and emergency locations associated with the device identifiers corresponding to a plurality of emergency alerts; and
   e) transmit the emergency data comprising the device identifiers and the emergency locations corresponding to the plurality of emergency alerts to the first ESP through the active communication link with the computing device providing the emergency response application at the first ESP.

16. The system of claim 15, wherein the at least one processor is further operative to periodically transmit subsequent third-party queries comprising the identifier of the first ESP to the third-party server.

17. The system of claim 16, wherein the at least one processor is further operative to periodically transmit the subsequent third-party queries to the third-party server for the duration of the active communication link established between the EMS and the first ESP through the emergency response application.

18. The system of claim 15, wherein the at least one processor is further operative to:
   a) detect an active communication link established with a second ESP through an emergency response application executed on a computing device at the second ESP;
   b) transmit a third-party query comprising an identifier of the second ESP to a third-party server;
   c) receive emergency data tagged with the identifier of the second ESP from the third-party server, wherein the emergency data comprises device identifiers and emergency locations associated with the device identifier corresponding to a second plurality of emergency alerts;
   d) in response to detecting the active communication link between the EMS and the second ESP and receiving the emergency data tagged with the identifier of the second ESP, transmit the emergency data comprising the device identifiers and the emergency locations corresponding to the second plurality of emergency alerts to the second ESP for display within the emergency response application executed on the computing device at the second ESP.

19. The system of claim 1, wherein the active communication link is a persistent communication link between the EMS and the first ESP that is maintained until the persistent communication link is terminated by the EMS or the first ESP.

20. The system of claim 1, wherein the at least one processor is operative to automatically transmit the emergency data comprising the device identifiers and the emergency locations corresponding to the plurality of emergency alerts to the first ESP for display within the emergency response application without receiving an emergency data request from the first ESP.

\* \* \* \* \*